(12) United States Patent
Oikawa et al.

(10) Patent No.: US 7,256,243 B2
(45) Date of Patent: Aug. 14, 2007

(54) SILICON COMPOUND

(75) Inventors: Hisao Oikawa, Chiba (JP); Mikio Yamahiro, Chiba (JP); Kazuhiro Yoshida, Chiba (JP); Nobumasa Ootake, Chiba (JP); Kenichi Watanabe, Chiba (JP); Kohji Ohno, Kyoto (JP); Yoshinobu Tsujii, Kyoto (JP); Takeshi Fukuda, Kyoto (JP)

(73) Assignee: Chisso Corporation, Osaka (JP)

( * ) Notice: Subject to any disclaimer, the term of this patent is extended or adjusted under 35 U.S.C. 154(b) by 266 days.

(21) Appl. No.: 11/121,120

(22) Filed: May 4, 2005

(65) Prior Publication Data

US 2005/0250925 A1 Nov. 10, 2005

(30) Foreign Application Priority Data

May 7, 2004 (JP) .............................. 2004-138513

(51) Int. Cl.
*C08F 4/16* (2006.01)
*C08G 77/442* (2006.01)

(52) U.S. Cl. .......................... 526/126; 528/31; 528/34; 525/100; 525/102; 525/106; 526/128; 526/129

(58) Field of Classification Search ................ 526/126, 526/128, 129
See application file for complete search history.

(56) References Cited

U.S. PATENT DOCUMENTS

| | | | |
|---|---|---|---|
| 2002/0106513 A1* | 8/2002 | Matyjaszewski et al. ... | 428/404 |
| 2005/0049381 A1* | 3/2005 | Yamahiro et al. ............. | 528/10 |
| 2005/0288468 A1* | 12/2005 | Ohno et al. ............... | 526/317.1 |
| 2006/0052623 A1 | 3/2006 | Yoshida et al. | |
| 2006/0094849 A1* | 5/2006 | Toyoda ......................... | 528/34 |
| 2006/0175684 A1* | 8/2006 | Oikawa et al. ............. | 257/632 |
| 2006/0287454 A1* | 12/2006 | Yamahiro et al. ........... | 526/279 |

FOREIGN PATENT DOCUMENTS

EP 1 428 795 6/2004

OTHER PUBLICATIONS

"Novel Inorganic-Organic Hybrid Block Copolymers as Pore Generators for Nanoporous Ultralow Dielectric Constant Films" authored by Yoon et al. and published in Macromolecules 2005, 38, 1031-1034.*

"Living Radical Polymerization by Polyhedral Oligomeric Silsesquioxane-Holding Initiators: Precision Synthesis of Tadpole-Shaped Organic/Inorganic Hybrid Polymers" authored by Fukuda et al and published in Macromolecules 2004, 37, 8517-8522.*

Abstract for "Modified Cubic Spherosilicates as Macroinitiators for the Synthesis of Inorganic-Organic Starlike Polymers" authored by Holzinger et al. and published in the Journal of Polymer Science, Part A: Polymer Chemistry 2002, 40(21) 3858-3872.*

"Organic/Inorganic Nanocomposite star Polymers via Atom Transfer Radical Polymerization of Methyl Methacrylate Using Octafunctional Silsesquioxane Cores" authored by Laine et al. and published in Macromolecules 2001, 34, 5398-5407.*

Chunxin Zhang et al., "Hydrosilylation of Allyl Alcohol with $[HSiMe_2OSiO_{1.5}]_8$: Octa(3-hydroxypropyldimethylsiloxy)octasilsesquioxane and Its Octamethacrylate Derivative as Potential Precursors to Hybrid Nanocomposites", J. Am. Chem. Soc., 122, 6979-6988, 2000.

Alan Sellinger et al., "Silsesquioxanes as Synthetic Platforms. 3. Photocurable, Liquid Epoxies as Inorganic/Organic Hybrid Precursors", Chem. Mater., vol. 8, No. 8, pp. 1592-1593, 1996.

Alan Sellinger et al., "Silsesquioxanes as Synthetic Platforms. Thermally Curable and Photocurable Inorganic/Organic Hybrids", Macromolecules, 29, pp. 2327-2330, 1996.

Krzysztof Matyjaszewski et al., "Atom Transfer Radical Polymerization", Chem. Rev., 101, 2921-2990, 2001.

* cited by examiner

*Primary Examiner*—Marc S. Zimmer
(74) *Attorney, Agent, or Firm*—Wenderoth, Lind & Ponack, L.L.P.

(57) ABSTRACT

The present invention provides a novel silicon compound represented by Formula (1) having a living radical polymerization initiating ability for addition-polymerizable monomers and a polymer obtained using the same. The above polymer can provide an organic-inorganic composite material having a distinct structure.

(1)

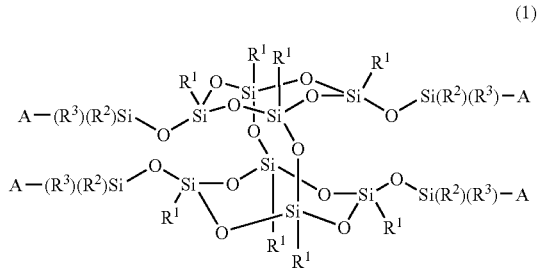

wherein $R^1$ is hydrogen, alkyl, aryl or arylalkyl; $R^2$ and $R^3$ are alkyl, phenyl or cyclohexyl; and A is a group having an ability to initiate polymerization of a monomer.

54 Claims, No Drawings

SILICON COMPOUND

FIELD OF THE INVENTION

The present invention relates to a novel silicon compound characterized by having a polymerization initiating ability for addition-polymerizable monomers, a production process for the same and a polymer obtained using the same.

BACKGROUND OF THE INVENTION

Polymers have come to be used in various fields not only as a general purpose structure-forming material but also as a value-added type material having functions and performances of a high degree. This is followed by an increase in the importance of producing high molecular materials under precise design. Attentions are paid on silsesquioxane derivatives of a cage type having a dimethylsiloxy group as an organic-inorganic composite material containing silsesquioxane as an inorganic component. This is because they are expected to be applied to precursors of organic/inorganic hybrid materials, low dielectric materials, optical crystals and materials forming liquid crystal display elements, and the reason therefor resides in that the above silsesquioxane derivatives have a structure close to those of silica and zeolite. Cage type silsesquioxanes in which a hydroxyl group (J. Am. Chem. Soc., 122 (200), 6979-), an epoxy group (Chemistry of Materials, 8 (1996), 1592-) or a methacryloyloxy group (Macromolecules, 29 (1996), 2327-) is bonded to a dimethylsiloxy group are reported. So-called organic-inorganic composite materials of organic polymers and silsesquioxanes are prepared by making use of the above functional groups. The organic-inorganic composite materials can be obtained by radically polymerizing cage type silsesquioxanes having a methacryloyloxy group alone or under the coexistence of other acryl base monomers.

In order to optimize the functions of high molecular materials according to purposes, the molecular properties of a polymer and the properties thereof as a molecular aggregate have to be precisely analyzed, and this makes it necessary to use a polymer having a distinct structure. However, conventional organic-inorganic composite materials do not contain polymers in which a structure is controlled as an organic component including the composite materials described above. A large part of them is obtained by mechanically blending silsesquioxanes with organic polymers, and therefore it used to be very difficult to control a structure thereof as a molecular aggregate of a composite matter. Then, it has come to be tried to control a structure of a polymer by using a polymerization initiator. It is disclosed in Chem. Rev., 101 (2001), 2921- that an α-haloester group is a good polymerization initiator for styrene base monomers and methacrylic acid base monomers in living polymerization, but silsesquioxane derivatives having an α-haloester group have not been known to date.

DISCLOSURE OF THE INVENTION

An object of the present invention is to provide a novel silicon compound having a living radical polymerization initiating ability for addition-polymerizable monomers of a wide range and a polymer obtained using the same to thereby solve the problems described above regarding conventional organic-inorganic composite materials.

The present inventors have found a silicon compound which has a functional group having a living radical polymerization initiating ability for addition-polymerizable monomers of a wide range and which has a silsesquioxane skeleton of a double decker (a structure in which two corners in a cage type structure of an octasilsesquioxane are broken) structure. Then, they have found that the above silicon compound is effective for solving the problem described above, and they have completed the present invention based on the above knowledge. That is, the present invention comprises the following structures.

[1] A silicon compound represented by Formula (1):

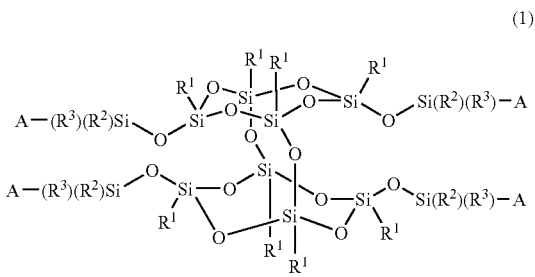

(1)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and A is a group having a polymerization initiating ability for a monomer.

[2] The silicon compound as described in the item [1], wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and A is a group having a living radical polymerization initiating ability for a monomer.

[3] The silicon compound as described in the item [1], wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalky lene; R² and R³ are groups independently selected from alkyl having a carbon atom number of 1 to 8, phenyl and cyclohexyl; and A is a group represented by any of Formula (2-1), Formula (2-2), Formula (2-3) and Formula (2-4);

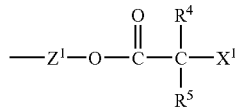
(2-1)

wherein $Z^1$ is alkylene having a carbon atom number of 2 to 20 or alkenylene having a carbon atom number of 3 to 8, and optional —CH₂— in these alkylene and alkenylene may be substituted with —O—; R⁴ is hydrogen, alkyl having a carbon atom number of 1 to 20, aryl having a carbon atom number of 6 to 20 or arylalkyl having a carbon atom number of 7 to 20; R⁵ is alkyl having a carbon atom number of 1 to 20, aryl having a carbon atom number of 6 to 20 or arylalkyl having a carbon atom number of 7 to 20; and X¹ is halogen;

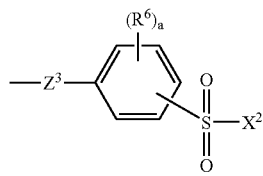
(2-2)

wherein $Z^3$ is alkylene having a carbon atom number of 2 to 10, and optional —CH₂— in this alkylene may be substituted with —O— or —COO—; R⁶ is alkyl having a carbon atom number of 1 to 3; a is an integer of 0 to 2; X² is halogen; and a bonding position of —SO₂X² on the benzene ring is an ortho position, a meta position or a para position to a bonding position of Z³, and a bonding position of R⁶ is an optional position excluding the respective bonding positions of Z³ and —SO₂X²;

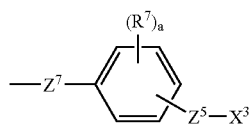
(2-3)

wherein $Z^5$ is alkylene which has a carbon atom number of 1 to 3 and in which optional —CH₂— may be substituted with —O—; Z⁷ is alkylene which has a carbon atom number of 2 to 10 and in which optional —CH₂— may be substituted with —O—, —COO— or —OCO—; R⁷ is alkyl having a carbon atom number of 1 to 3; a is an integer of 0 to 2; X³ is halogen; and a bonding position of Z⁵ on the benzene ring is a meta position or a para position to a bonding position of Z⁷, and a bonding position of R⁷ is an optional position excluding the respective bonding positions of Z⁵ and Z⁷;

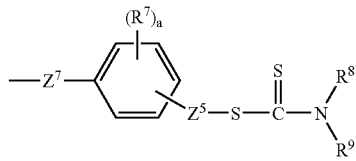
(2-4)

wherein R⁸ and R⁹ are independently alkyl having a carbon atom number of 1 to 12, cycloalkyl having a carbon atom number of 5 to 10 or aryl having a carbon atom number of 6 to 10, and R⁸ and R⁹ may be combined with each other to form a ring together with N; Z⁵ is alkylene which has a carbon atom number of 1 to 3 and in which optional —CH₂— may be substituted with —O—; Z⁷ is alkylene which has a carbon atom number of 2 to 10 and in which optional —CH₂— may be substituted with —O—, —COO— or —OCO—; R⁷ is alkyl having a carbon atom number of 1 to 3; a is an integer of 0 to 2; and a bonding position of Z⁵ on the benzene ring is a meta position or a para position to a bonding position of Z⁷, and a bonding position of R⁷ is an optional position excluding the respective bonding positions of Z⁵ and Z⁷.

[4] The silicon compound as described in the item [3], wherein respective R¹'s are groups independently selected from hydrogen and alkyl having a carbon atom number of 1 to 30 in which optional hydrogen may be substituted with fluorine and in which optional —CH₂— may be substituted with —O— or cycloalkylene.

[5] The silicon compound as described in the item [3], wherein respective R¹'s are groups independently selected from alkenyl having a carbon atom number of 2 to 20 in which optional hydrogen may be substituted with fluorine and in which optional —CH₂— may be substituted with —O— or cycloalkylene and alkyl having a carbon atom number of 1 to 20 in which optional hydrogen may be substituted with fluorine and in which at least one —CH₂— is substituted with cycloalkenylene.

[6] The silicon compound as described in the item [3], wherein respective R¹'s are groups independently selected from phenyl in which optional hydrogen may be substituted with halogen or alkyl having a carbon atom number of 1 to 10 and non-substituted naphthyl; in alkyl which is a substituent of the phenyl, optional hydrogen may be substituted with fluorine, and optional —CH₂— may be substituted with —O—, —CH=CH—, cycloalkylene or phenylene; and when the phenyl has plural substituents, the substituents may be the same group or different groups.

[7] The silicon compound as described in the item [3], wherein respective R¹'s are groups independently selected from phenylalkyl constituted from a phenyl group in which optional hydrogen may be substituted with halogen or alkyl having a carbon atom number of 1 to 12 and an alkylene group having a carbon atom number of 1 to 12 in which optional hydrogen may be substituted with fluorine and in which optional —CH₂— may be substituted with —O—, —CH=CH— or cycloalkylene; in alkyl which is a substituent of the phenyl group, optional hydrogen may be substituted with fluorine, and optional —CH$_2$— may be substituted with —O—, —CH=CH—, cycloalkylene or phenylene; and when the phenyl group has plural substituents, the substituents may be the same group or different groups.

[8] The silicon compound as described in the item [3], wherein respective R$^1$'s are groups independently selected from alkyl having a carbon atom number of 1 to 8 in which optional hydrogen may be substituted with fluorine and in which optional —CH$_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —CH$_2$— may be substituted with —O—, —CH=CH— or cycloalkylene; and when the phenyl or a phenyl group in the phenylalkyl has plural substituents, the substituents may be the same group or different groups.

[9] The silicon compound as described in the item [3], wherein all R$^1$'s are the same group selected from alkyl having a carbon atom number of 1 to 8 in which optional hydrogen may be substituted with fluorine and in which optional —CH$_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —CH$_2$— may be substituted with —O—, —CH=CH— or cycloalkylene; and when the phenyl or a phenyl group in the phenylalkyl has plural substituents, the substituents may be the same group or different groups.

[10] The silicon compound as described in the item [3], wherein all R$^1$'s are phenyl.

[11] The silicon compound as described in the item [3], wherein all R$^1$'s are phenyl, and R$^2$ and R$^3$ are methyl.

[12] The silicon compound as described in the item [3], wherein all R$^1$'s are the same group selected from alkyl having a carbon atom number of 1 to 8 in which optional hydrogen may be substituted with fluorine and in which optional —CH$_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —CH$_2$— may be substituted with —O—, —CH=CH— or cycloalkylene; when the phenyl or a phenyl group in the phenylalkyl has plural substituents, the substituents may be the same group or different groups; and A is the group represented by Formula (2-1):

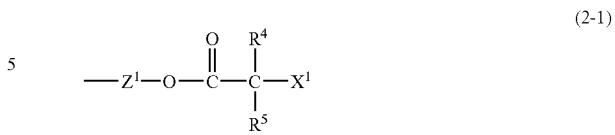

(2-1)

wherein Z$^1$ is alkylene having a carbon atom number of 2 to 20 or alkenylene having a carbon atom number of 3 to 8, and optional —CH$_2$— in these alkylene and alkenylene may be substituted with —O—; R$^4$ is hydrogen, alkyl having a carbon atom number of 1 to 20, aryl having a carbon atom number of 6 to 20 or arylalkyl having a carbon atom number of 7 to 20; R$^5$ is alkyl having a carbon atom number of 1 to 20, aryl having a carbon atom number of 6 to 20 or arylalkyl having a carbon atom number of 7 to 20; and X$^1$ is halogen.

[13] The silicon compound as described in the item [3], wherein all R$^1$'s are phenyl; A is the group represented by Formula (2-1); and Z$^1$ in Formula (2-1) is alkylene which has a carbon atom number of 2 to 10 and in which optional —CH$_2$— may be substituted with —O—.

[14] The silicon compound as described in the item [3], wherein all R$^1$'s are phenyl; R$^2$ and R$^3$ are methyl; A is the group represented by Formula (2-1); in Formula (2-1), Z$^1$ is —C$_2$H$_4$—, —C$_3$H$_6$— or —C$_2$H$_4$—O—C$_3$H$_6$—; R$^4$ and R$^5$ are methyl; and X$^1$ is bromine.

[15] The silicon compound as described in the item [3], wherein all R$^1$'s are the same group selected from alkyl having a carbon atom number of 1 to 8 in which optional hydrogen may be substituted with fluorine and in which optional —CH$_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —CH$_2$— may be substituted with —O—, —CH=CH— or cycloalkylene; when the phenyl or a phenyl group in the phenylalkyl has plural substituents, the substituents may be the same group or different groups; and A is the group represented by Formula (2-2):

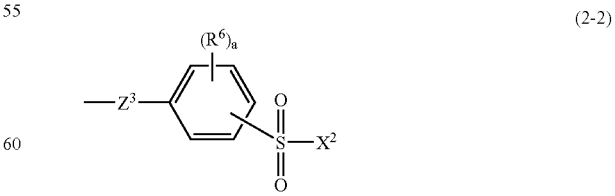

(2-2)

wherein Z$^3$ is alkylene having a carbon atom number of 2 to 10, and optional —CH$_2$— in this alkylene may be substituted with —O— or —COO—; R$^6$ is alkyl having a carbon atom number of 1 to 3; a is an integer of 0 to 2; $X^2$ is halogen; and a bonding position of —$SO_2X^2$ on the benzene ring is an ortho position, a meta position or a para position to a bonding position of $Z^3$, and a bonding position of $R^6$ is an optional position excluding the respective bonding positions of $Z^3$ and —$SO_2X^2$.

[16] The silicon compound as described in the item [3], wherein all $R^1$'s are phenyl; A is the group represented by Formula (2-2); $Z^3$ in Formula (2-2) is —$C_2H_4$—$Z^9$; and $Z^9$ is a single bond or alkylene which has a carbon atom number of 1 to 8 and in which optional —$CH_2$— may be substituted with —O— or —COO—.

[17] The silicon compound as described in the item [3], wherein all $R^1$'s are phenyl; $R^2$ and $R^3$ are methyl; A is the group represented by Formula (2-2); in Formula (2-2), $Z^3$ is —$C_2RH_4$—; $X^2$ is chlorine or bromine; and a is 0.

[18] The silicon compound as described in the item [3], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and A is the group represented by Formula (2-3):

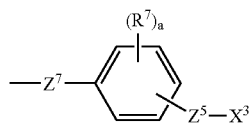

(2-3)

wherein $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; $X^3$ is halogen; and a bonding position of $Z^5$ on the benzene ring is a meta position or a para position to a bonding position of $Z^7$, and a bonding position of $R^7$ is an optional position excluding the respective bonding positions of $Z^5$ and $Z^7$.

[19] The silicon compound as described in the item [3], wherein all $R^1$'s are phenyl; A is the group represented by Formula (2-3); $Z^7$ in Formula (2-3) is —$C_2H_4$—$Z^{10}$; and $Z^{10}$ is a single bond or alkylene which has a carbon atom number of 1 to 8 and in which optional —$CH_2$— may be substituted with —O—, —COO— or —OCO—.

[20] The silicon compound as described in the item [3], wherein all $R^1$'s are phenyl; $R^2$ and $R^3$ are methyl; A is the group represented by Formula (2-3); in Formula (2-3), $Z^5$ is —$CH_2$—; $Z^7$ is —$C_2H_4$—; $X^3$ is chlorine or bromine; and a is 0.

[21] The silicon compound as described in the item [3], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and A is the group represented by Formula (2-4):

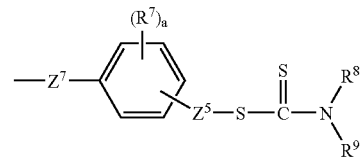

(2-4)

wherein $R^8$ and $R^9$ are independently hydrogen, alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; and a bonding position of $Z^5$ on the benzene ring is a meta position or a para position to a bonding position of $Z^7$, and a bonding position of $R^7$ is an optional position excluding the respective bonding positions of $Z^5$ and $Z^7$.

[22] The silicon compound as described in the item [3], wherein all $R^1$'s are phenyl; A is the group represented by Formula (2-4); and in Formula (2-4), $Z^7$ is —$C_2H_4$—$Z^{10}$, and $Z^{10}$ is a single bond or alkylene which has a carbon atom number of 1 to 8 and in which optional —$CH_2$— may be substituted with —O—, —COO— or —OCO—.

[23] The silicon compound as described in the item [3], wherein all $R^1$'s are phenyl; $R^2$ and $R^3$ are methyl; A is the group represented by Formula (2-4); in Formula (2-4), $R^8$ and $R^8$ are ethyl; $Z^5$ is —$CH_2$—; $Z^7$ is —$C_2H_4$—; and a is 0.

[24] A production process for a silicon compound represented by Formula (1-1) characterized by obtaining a compound represented by Formula (5) by a step (a) and carrying out a step (b) and then a step (c):

(1-1)

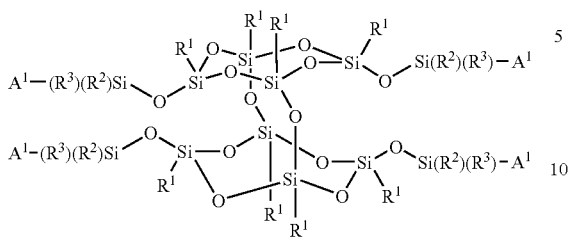

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^1$ is a group represented by Formula (2-1-1):

(2-1-1)

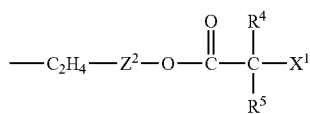

wherein $Z^2$ is a single bond or alkylene having a carbon atom number of 1 to 18 or alkenylene having a carbon atom number of 2 to 6, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; and $X^1$ is halogen;

<Step (a)> a step in which a compound represented by Formula (3-1) is reacted with a compound represented by Formula (4) to thereby obtain a compound represented by Formula (5):

(3-1)

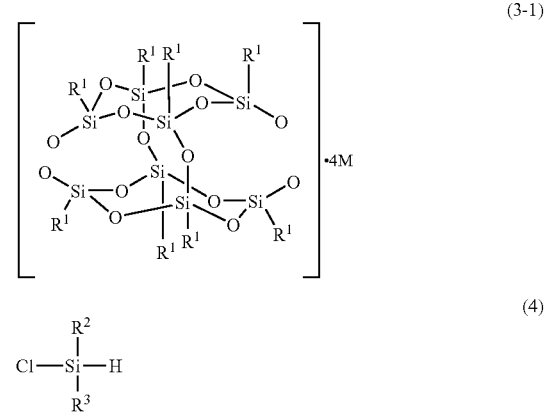

(4)

$$Cl-\underset{\underset{R^3}{|}}{\overset{\overset{R^2}{|}}{Si}}-H$$

(5)

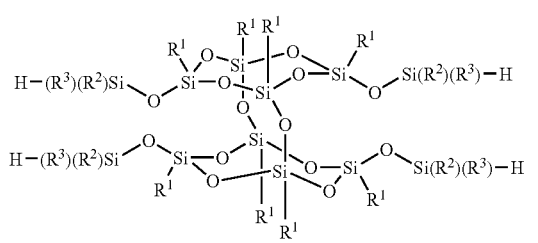

wherein in the above formulas, $R^1$, $R^2$ and $R^3$ have the same meanings as those of these codes in Formula (1-1), and M is a monovalent alkali metal atom;

<Step (b)> a step in which the compound represented by Formula (5) is reacted with a compound represented by Formula (6) in the presence of a transition metal catalyst to obtain a silicon compound represented by Formula (7):

(6)

(7)

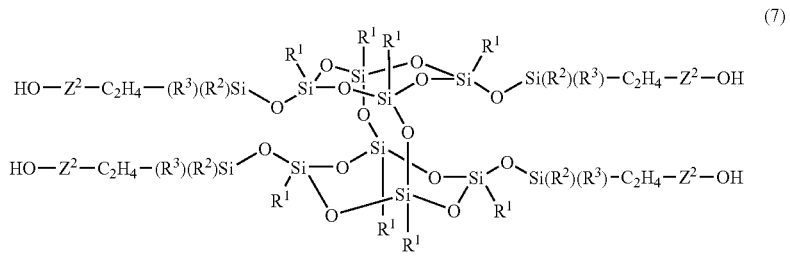

wherein $Z^2$ in the above formulas has the same meaning as that of $Z^2$ in Formula (2-1-1), and $R^1$, $R^2$ and $R^3$ in Formula (7) have the same meanings as those of these codes in Formula (1-1);

<Step (c)> a step in which the compound represented by Formula (7) is reacted with a compound represented by Formula (8) to obtain the silicon compound represented by Formula (1-1):

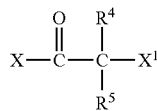

(8)

wherein $R^4$, $R^5$ and $X^1$ have the same meanings as those of these codes in Formula (2-1-1); and X is halogen.

[25] The production process as described in the item [24], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

[26] The production process as described in the item [24], wherein all $R^1$'s are phenyl, and $R^2$ and $R^3$ are methyl.

[27] A production process for a silicon compound represented by Formula (1-1) characterized by obtaining a compound represented by Formula (5) by a step (d) and carrying out a step (b) and then a step (c):

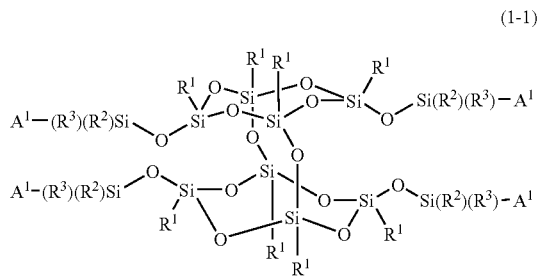

(1-1)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^1$ is a group represented by Formula (2-1-1):

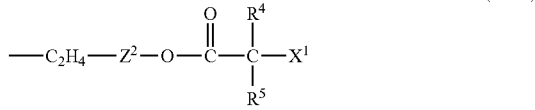

(2-1-1)

wherein $Z^2$ is a single bond or alkylene having a carbon atom number of 1 to 18 or alkenylene having a carbon atom number of 2 to 6, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; and $X^1$ is halogen;

<Step (d)> a step in which a compound represented by Formula (3-2) is reacted with a compound represented by Formula (4) to thereby obtain a compound represented by Formula (5):

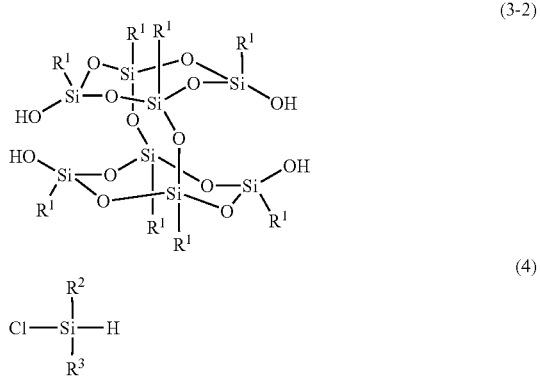

(3-2)

(4)

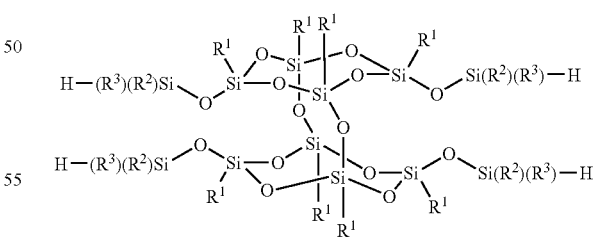

(5)

wherein $R^1$, $R^2$ and $R^3$ in the above formulas have the same meanings as those of these codes in Formula (1-1);

<Step (b)> a step in which the compound represented by Formula (5) is reacted with a compound represented by Formula (6) in the presence of a transition metal catalyst to obtain a silicon compound represented by Formula (7):

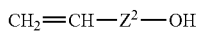

(6)

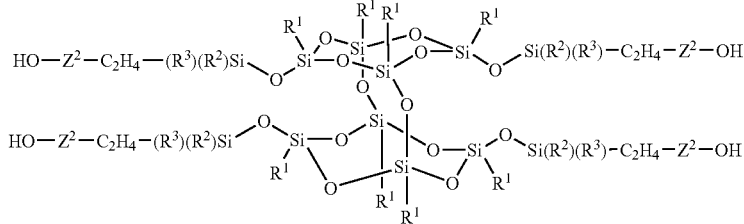

(7)

wherein $Z^2$ in the above formulas has the same meaning as that of $Z^2$ in Formula (2-1-1), and $R^1$, $R^2$ and $R^3$ in Formula (7) have the same meanings as those of these codes in Formula (1-1);

<Step (c)> a step in which the compound represented by Formula (7) is reacted with a compound represented by Formula (8) to obtain the silicon compound represented by Formula (1-1):

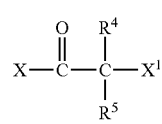

(8)

wherein $R^4$, $R^5$ and $X^1$ have the same meanings as those of these codes in Formula (2-1-1); and X is halogen.

[28] The production process as described in the item [27], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

[29] The production process as described in the item [27], wherein all $R^1$'s are phenyl, and $R^2$ and $R^3$ are methyl.

[30] A production process for a silicon compound represented by Formula (1-3) characterized by carrying out a step (e) and then a step (f):

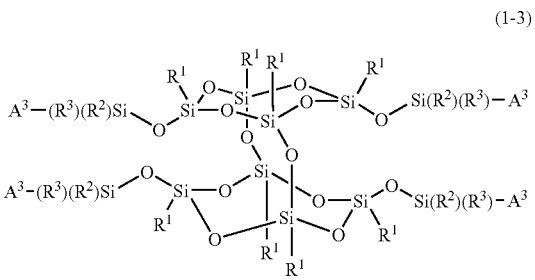

(1-3)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^3$ is a group represented by Formula (2-3-1):

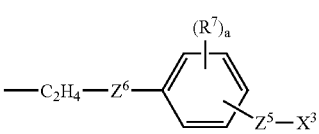

(2-3-1)

wherein $Z^5$ is alkylene which has a carbon atom number of 1 to 3 and in which optional —$CH_2$— may be substituted with —O—; $Z^6$ is a single bond or alkylene which has a carbon atom number of 1 to 8 and in which optional —$CH_2$— may be substituted with —O—, —COO— or —OCO—; $R^7$ is alkyl having a carbon atom number of 1 to 3; a is an integer of 0 to 2; $X^3$ is halogen; and a bonding position of $Z^5$ on the benzene ring is a meta position or a para position to a bonding position of $Z^6$, and a bonding position of $R^7$ is an optional position excluding the respective bonding positions of $Z^5$ and $Z^6$;

<Step (e)>
a step in which a compound represented by Formula (4) is reacted with a compound represented by Formula (3-1) or a compound represented by Formula (3-2) to obtain a silicon compound represented by Formula (5):

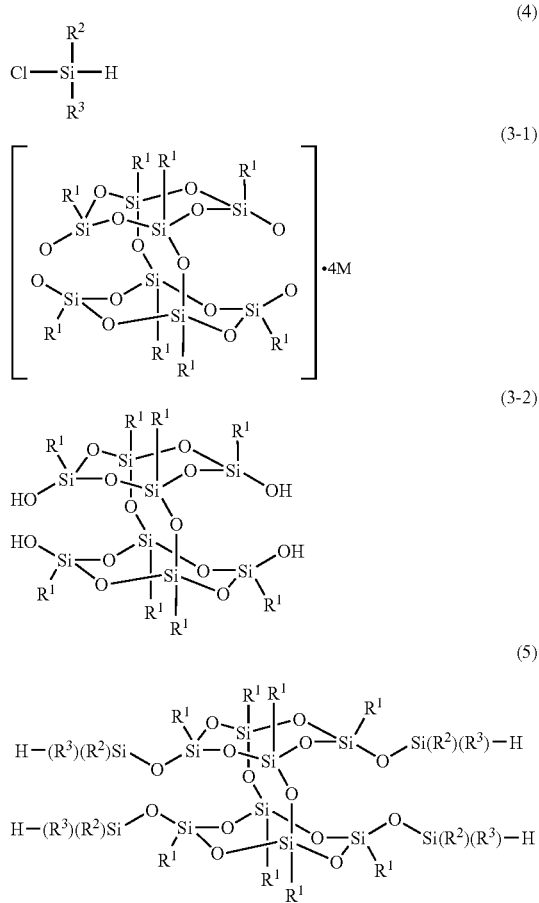

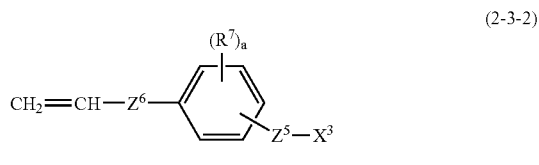

wherein $R^1$, $R^2$ and $R^3$ in the above formulas have the same meanings as those of these codes in Formula (1-3), and M is a monovalent alkali metal atom;

<Step (f)>
a step in which the compound represented by Formula (5) is reacted with a compound represented by Formula (2-3-2) to obtain the silicon compound represented by Formula (1-3):

wherein $Z^5$, $Z^6$, $R^7$, a and $X^3$ have the same meanings as those of these codes in Formula (2-3-1); and the bonding positions of $Z^5$ and $R^7$ on the benzene ring are the same as the bonding positions thereof in Formula (2-3-1).

[31] The production process as described in the item [30], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

[32] The production process as described in the item [30], wherein all $R^1$'s are phenyl, and $R^2$ and $R^3$ are methyl.

[33] A production process for a silicon compound represented by Formula (1-4) characterized by reacting a silicon compound represented by Formula (1-3) with a compound represented by Formula (9):

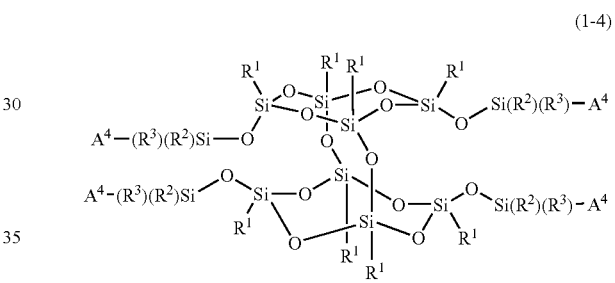

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^4$ is a group represented by Formula (2-4-1):

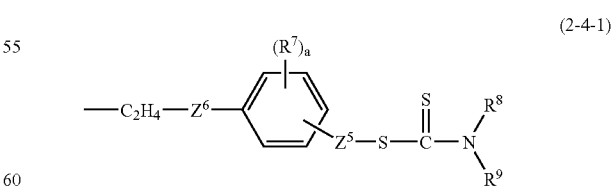

wherein $Z^5$ is alkylene which has a carbon atom number of 1 to 3 and in which optional —$CH_2$— may be substituted with —O—; $Z^6$ is a single bond or alkylene which has a carbon atom number of 1 to 8 and in which optional —$CH_2$— may be substituted with —O—, —COO— or —OCO—; $R^8$ and $R^9$ are independently hydrogen, alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $R^7$ is alkyl having a carbon atom number of 1 to 3; a is an integer of 0 to 2; and a bonding position of $Z^5$ on the benzene ring is a meta position or a para position to a bonding position of $Z^6$, and a bonding position of $R^7$ is an optional position excluding the respective bonding positions of $Z^5$ and $Z^6$;

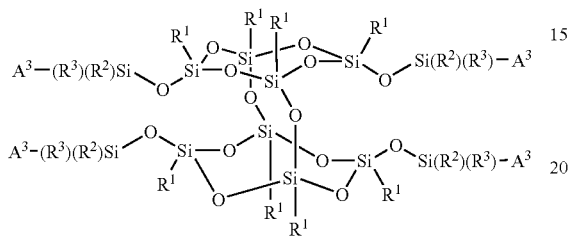

(1-3)

wherein $R^1$, $R^2$ and $R^3$ have the same meanings as those of these codes in Formula (1-4), and $A^3$ is a group represented by Formula (2-3-1):

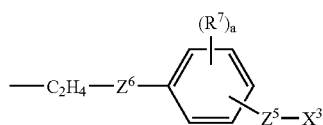

(2-3-1)

wherein $Z^5$, $Z^6$, $R^7$ and a have the same meanings as those of these codes in Formula (2-4-1); $X^3$ is halogen; and the bonding positions of $Z^5$ and $R^7$ on the benzene ring are the same as the bonding positions thereof in Formula (2-4-1);

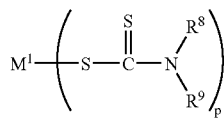

(9)

wherein $R^8$ and $R^9$ have the same meanings as those of these codes in Formula (2-4-1); $M^1$ is a metal element of the first group or the second group in the periodic table; and p is the same value as a valence of $M^1$.

[34] The production process as described in the item [33], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

[35] The production process as described in the item [33], wherein all $R^1$'s are phenyl, and $R^2$ and $R^3$ are methyl.

[36] A production process for a silicon compound represented by Formula (1-1) characterized by carrying out a step (g) and then a step (h):

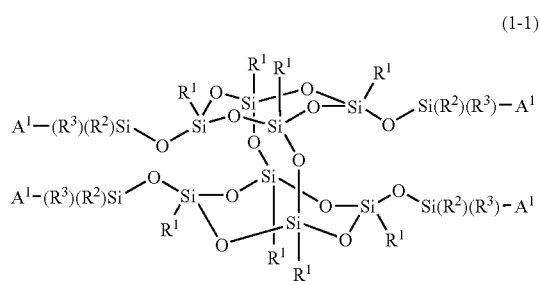

(1-1)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^1$ is a group represented by Formula (2-1-1):

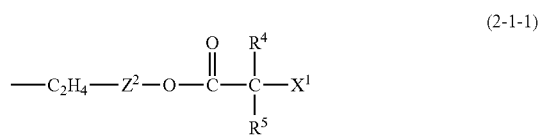

(2-1-1)

wherein $Z^2$ is a single bond or alkylene having a carbon atom number of 1 to 18 or alkenylene having a carbon atom number of 2 to 6, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; and $X^1$ is halogen;

<Step (g)> a step in which a compound represented by Formula (4) is reacted with a compound represented by Formula (2-1-2) in the presence of a transition metal catalyst to obtain a silicon compound represented by Formula (2-1-3):

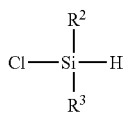

(4)

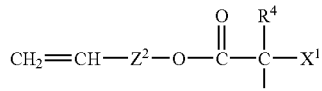

(2-1-2)

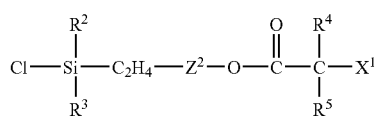

(2-1-3)

wherein $R^2$ and $R^3$ in the above formulas have the same meanings as those of these codes in Formula (1-1), and $Z^2$, $R^4$, $R^5$ and $X^1$ have the same meanings as those of these codes in Formula (2-1-1);

<Step (h)> a step in which the compound represented by Formula (2-1-3) is reacted with a compound represented by Formula (3-1) or a compound represented by Formula (3-2) to thereby obtain the compound represented by Formula (1-1):

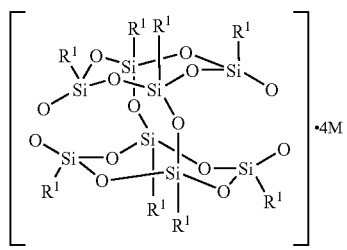

(3-1)

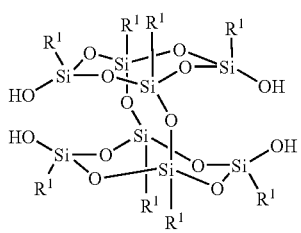

(3-2)

wherein $R^1$ in the above formulas has the same meaning as that of $R^1$ in Formula (1-1), and M is a monovalent alkali metal atom.

[37] The production process as described in the item [36], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

[38] The production process as described in the item [36], wherein all $R^1$'s are phenyl, and $R^2$ and $R^3$ are methyl.

[39] A production process for a silicon compound represented by Formula (1-2) characterized by carrying out a step (i) and then a step (j):

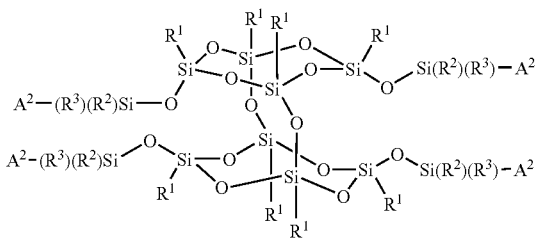

(1-2)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^2$ is a group represented by Formula (2-2-1):

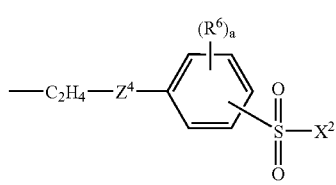

(2-2-1)

wherein $Z^4$ is a single bond or alkylene having a carbon atom number of 1 to 8, and optional —$CH_2$— in the above alkylene may be substituted with —O— or —COO—; $R^6$ is alkyl having a carbon atom number of 1 to 3; a is an integer of 0 to 2; $X^2$ is halogen; and a bonding position of —$SO_2X^2$ on the benzene ring is an ortho position, a meta position or a para position to a bonding position of $Z^4$, and a bonding position of $R^6$ is an optional position excluding the respective bonding positions of $Z^4$ and —$SO_2X^2$;

<Step (i)> a step in which a compound represented by Formula (4) is reacted with a compound represented by Formula (2-2-2) in the presence of a transition metal catalyst to obtain a compound represented by Formula (2-2-3):

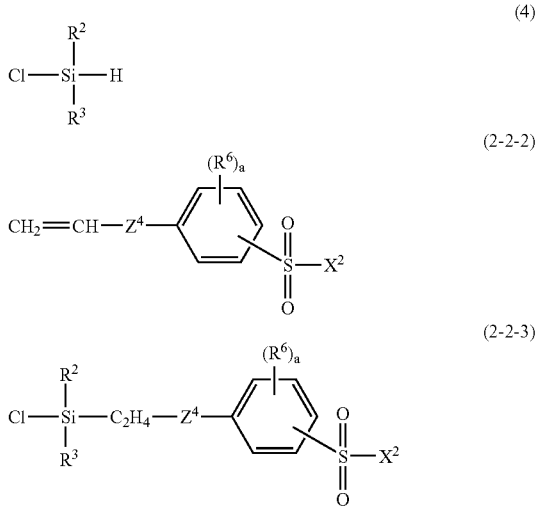

(4)

(2-2-2)

(2-2-3)

wherein $R^2$ and $R^3$ in the above formulas have the same meanings as those of these codes in Formula (1-2); $Z^4$, $R^6$, a and $X^2$ have the same meanings as those of these codes in Formula (2-2-1); and the bonding positions of —$SO_2X^2$ and $R^6$ on the benzene ring are the same as the bonding positions thereof in Formula (2-2-1);

<Step (j)> a step in which the compound represented by Formula (2-2-3) is reacted with a compound represented by Formula (3-1) or a compound represented by Formula (3-2) to obtain the silicon compound represented by Formula (1-2):

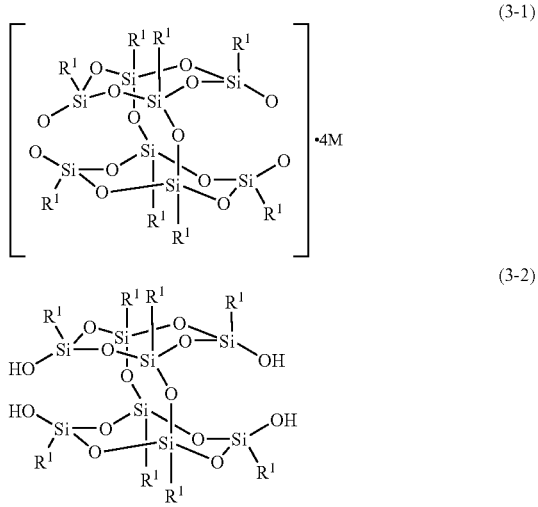

(3-1)

(3-2)

wherein $R^1$ in the above formulas has the same meaning as that of $R^1$ in Formula (1-1); and M is a monovalent alkali metal atom.

[40] The production process as described in the item [39], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

[41] The production process as described in the item [39], wherein all $R^1$'s are phenyl, and $R^2$ and $R^3$ are methyl.

[42] A production process for a silicon compound represented by Formula (1-3) characterized by carrying out a step (k) and then a step (l):

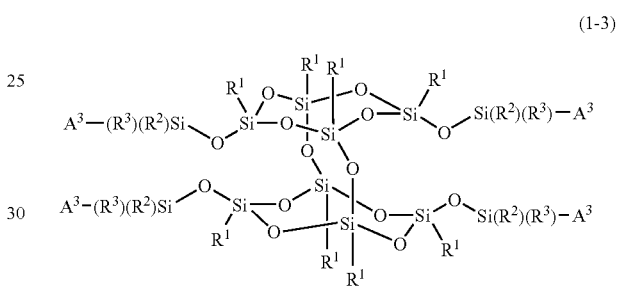

(1-3)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^3$ is a group represented by Formula (2-3-1):

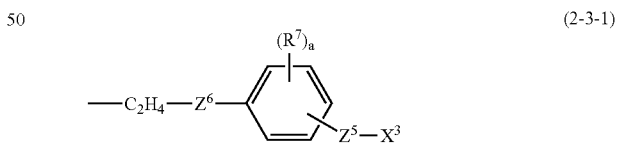

(2-3-1)

wherein $Z^5$ is alkylene which has a carbon atom number of 1 to 3 and in which optional —$CH_2$— may be substituted with —O—; $Z^6$ is a single bond or alkylene which has a carbon atom number of 1 to 8 and in which optional —$CH_2$— may be substituted with —O—, —COO— or —OCO—; $R^7$ is alkyl having a carbon atom number of 1 to 3; a is an integer of 0 to 2; $X^3$ is halogen; and a bonding position of $Z^5$ on the benzene ring is a meta position or a para position to a bonding position of $Z^6$, and a bonding position of $R^7$ is an optional position excluding the respective bonding positions of $Z^5$ and $Z^6$;

<Step (k)> a step in which a compound represented by Formula (4) is reacted with a compound represented by Formula (2-3-2) in the presence of a transition metal catalyst to obtain a compound represented by Formula (2-3-3):

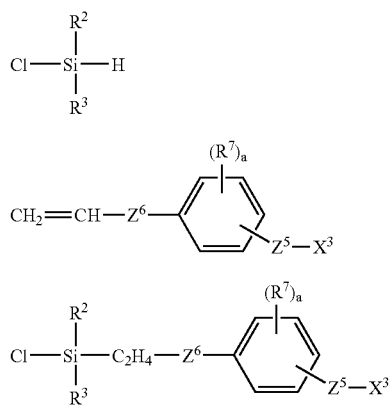

wherein $R^2$ and $R^3$ in the above formulas have the same meanings as those of these codes in Formula (1-3); $Z^5$, $Z^6$, $R^7$, a and $X^3$ have the same meanings as those of these codes in Formula (2-3-1); and the bonding positions of $Z^5$ and $R^7$ on the benzene ring are the same as the bonding positions thereof in Formula (2-3-1);

<Step (l)> a step in which the compound represented by Formula (2-3-3) is reacted with a compound represented by Formula (3-1) or a compound represented by Formula (3-2) to thereby obtain the silicon compound represented by Formula (1-3):

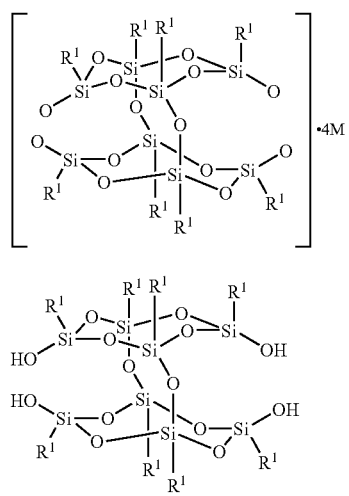

wherein $R^1$ in the above formulas has the same meaning as that of $R^1$ in Formula (1-3); and M is a monovalent alkali metal atom.

[43] The production process as described in the item [42], wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

[44] The production process as described in the item [42], wherein all $R^1$'s are phenyl, and $R^2$ and $R^3$ are methyl.

[45] A polymer obtained by polymerizing an addition-polymerizable monomer using the silicon compound as described in the item [1] as an initiator and using a transition metal complex as a catalyst.

[46] A polymer obtained by polymerizing an addition-polymerizable monomer using the silicon compound as described in the item [3] as an initiator and using a transition metal complex as a catalyst.

[47] A polymer represented by Formula (P-1):

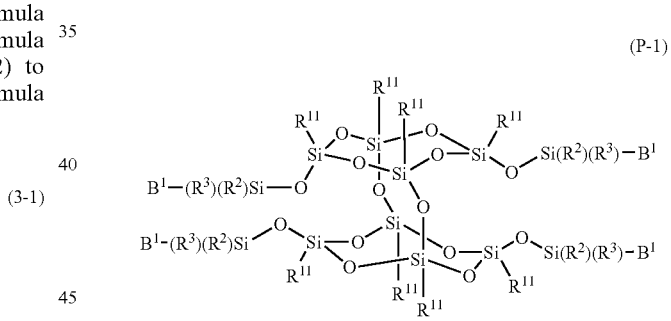

wherein all $R^{11}$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; $R^2$ and $R^3$ are groups independently selected from alkyl having a carbon atom number of 1 to 8, phenyl and cyclohexyl; and $B^1$ is a group represented by Formula (2-1-P):

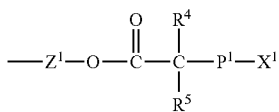

(2-1-P)

wherein $Z^1$ is alkylene having a carbon atom number of 2 to 20 or alkenylene having a carbon atom number of 3 to 8, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; $X^1$ is halogen; and $P^1$ is a chain of a structural unit obtained by polymerizing an addition-polymerizable monomer.

[48] A polymer represented by Formula (P-2):

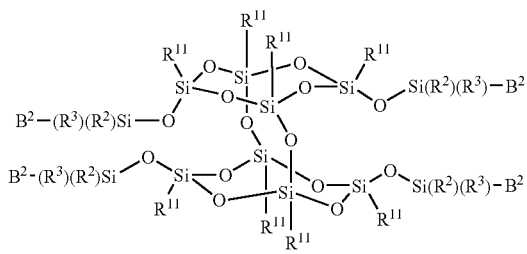

(P-2)

wherein all $R^{11}$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; $R^2$ and $R^3$ are groups independently selected from alkyl having a carbon atom number of 1 to 8, phenyl and cyclohexyl; and $B^2$ is a group represented by Formula (2-2-P):

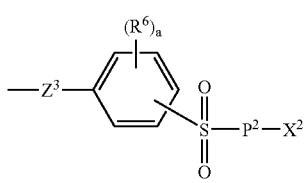

(2-2-P)

wherein $Z^3$ is alkylene having a carbon atom number of 2 to 10, and optional —$CH_2$— in the above alkylene may be substituted with —O— or —COO—; $R^6$ is alkyl having a carbon atom number of 1 to 3; a is an integer of 0 to 2; $X^2$ is halogen; a bonding position of —$SO_2$— on the benzene ring is an ortho position, a meta position or a para position to a bonding position of $Z^3$, and a bonding position of $R^6$ is an optional position excluding the respective bonding positions of $Z^3$ and —$SO_2$—; and $P^2$ is a chain of a structural unit obtained by polymerizing an addition-polymerizable monomer.

[49] A polymer represented by Formula (P-3):

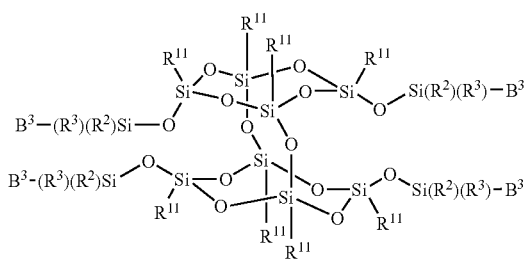

(P-3)

wherein all $R^{11}$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; $R^2$ and $R^3$ are groups independently selected from alkyl having a carbon atom number of 1 to 8, phenyl and cyclohexyl; and $B^3$ is a group represented by Formula (2-3-P):

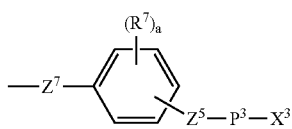

(2-3-P)

wherein $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; $X^3$ is halogen; a bonding position of $Z^5$ on the benzene ring is a meta position or a para position to a bonding position of $Z^7$, and a bonding position of $R^7$ is an optional position excluding the respective bonding positions of $Z^5$ and $Z^7$; and $P^3$ is a chain of a structural unit obtained by polymerizing an addition-polymerizable monomer.

[50] A polymer represented by Formula (P-4):

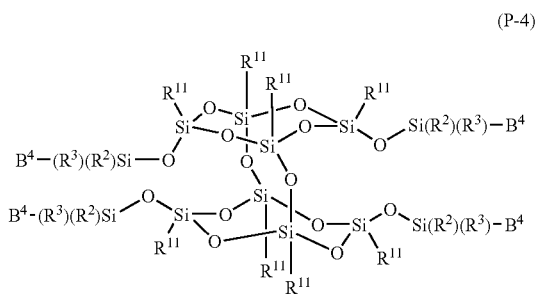

(P-4)

wherein all $R^{11}$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; $R^2$ and $R^3$ are groups independently selected from alkyl having a carbon atom number of 1 to 8, phenyl and cyclohexyl; and $B^4$ is a group represented by Formula (2-4-P):

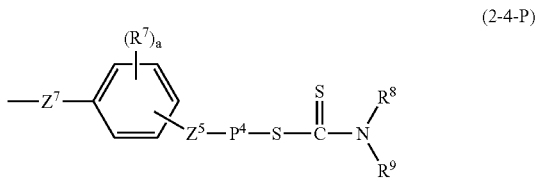

(2-4-P)

wherein $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^8$ and $R^9$ are independently hydrogen, alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $R^7$ is alkyl having a carbon atom number of 1 to 3; a is an integer of 0 to 2; a bonding position of $Z^5$ on the benzene ring is a meta position or a para position to a bonding position of $Z^7$, and a bonding position of $R^7$ is an optional position excluding the respective bonding positions of $Z^5$ and $Z^7$; and $P^4$ is a chain of a structural unit obtained by polymerizing an addition-polymerizable monomer.

[51] The polymer as described in the item [47], wherein the addition-polymerizable monomer is at least one selected from the group of (meth)acrylic acid derivatives and the group of styrene derivatives.

[52] The polymer as described in the item [48], wherein the addition-polymerizable monomer is at least one selected from the group of (meth)acrylic acid derivatives and the group of styrene derivatives.

[53] The polymer as described in the item [49], wherein the addition-polymerizable monomer is at least one selected from the group of (meth)acrylic acid derivatives and the group of styrene derivatives.

[54] The polymer as described in the item [50], wherein the addition-polymerizable monomer is at least one selected from the group of (meth)acrylic acid derivatives and the group of styrene derivatives.

The silicon compound provided by the present invention is a silsesquioxane derivative and has an excellent living-polymerizable radical polymerization initiating function. The silicon compound of the present invention shows an excellent living radical polymerization accelerating function particularly to (meth)acrylic acid derivatives and styrene derivatives. For example, it is possible to initiate polymerization of a (meth)acryl base monomer by the silicon compound of the present invention to form a (meth)acryl base polymer with 4 points in the silsesquioxane structure of the present invention being utilized as starting points. In the polymer thus obtained having an organic group of a silsesquioxane structure in a central part, it is possible as well to positively make use of interaction between the organic groups of the silsesquioxane structure thereof. This makes it possible not only to obtain an organic-inorganic composite material having a distinct structure but also to control the structure thereof as the molecular assemblies of the above polymer. Further, the silicon compound of the present invention has characteristics other than the function of a polymerization initiator. For example, α-haloester has a strong electrophilicity, and therefore reaction of the silicon compound of the present invention with nucleophilic reagents makes it possible to synthesize various silsesquioxane derivatives corresponding to the nucleophilic reagents. Accordingly, the silicon compound of the present invention is also useful as an intermediate in organic synthesis.

BEST MODE FOR CARRYING OUT THE INVENTION

First, terms used in the present invention shall be explained. "Optional" means that not only the position but also the number can optionally be selected, but it does not include the case where the number is 0. When it is described that "optional —$CH_2$— may be substituted with —O—", a case where plural continuous —$CH_2$— are substituted with —O— is not included therein. For example, alkyl in which optional —$CH_2$— may be substituted with —O— or —CH=CH— includes alkyl, alkoxy, alkoxyalkyl, alkenyl, alkyloxyalkenyl and alkenyloxyalkyl. Both of alkyl and alkylene may be either a linear group or a branched group. This shall be applied to a case where optional —$CH_2$— is substituted with other divalent group. For example, any of alkyl, alkenylene, alkenyl and alkylene in alkyloxyalkenyl and alkenyloxyalkyl each described above may be either a linear group or a branched group. Both of cycloalkyl and cycloalkenyl may be or may not be a cross-linked ring structure. A (meth)acrylic acid derivative is used as a general term for an acrylic acid derivative and a methacrylic acid derivative. (Meth)acrylate is used as a general term for acrylate and methacrylate. (Meth)acryloyloxy is used as a general term for acryloyloxy and methacryloyloxy.

The silicon compound of the present invention is represented by Formula (1). In the following explanations, the silicon compound represented by Formula (1) shall be described as the compound (1). Compounds represented by the other formulas shall be shown as well by the same abbreviation.

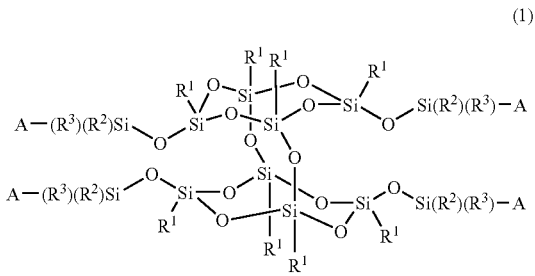

Respective $R^1$'s in Formula (1) are groups independently selected from hydrogen, alkyl having a carbon atom number of 1 to 45, substituted or non-substituted aryl and substituted or non-substituted arylalkyl. All $R^1$'s are preferably the same one group but may be constituted from two or more different groups. The examples of a case where eight $R^1$'s are constituted from different groups are a case where they are constituted from two or more alkyls, a case where they are constituted from two or more aryls, a case where they are constituted from two or more arylalkyls, a case where they are constituted from hydrogen and at least one aryl, a case where they are constituted from at least one alkyl and at least one aryl, a case where they are constituted from at least one alkyl and at least one arylalkyl and a case where they are constituted from at least one aryl and at least one arylalkyl. They ma be combinations other than the above examples. The compound (1) having at least two different $R^1$'s can be obtained by using two or more raw materials in producing it. The raw materials shall be described later.

When $R^1$ is alkyl, it has a carbon atom number of 1 to 45. The preferred carbon atom number is 1 to 30. The more preferred carbon atom number is 1 to 8. Optional hydrogen thereof may be substituted with fluorine, and optional —$CH_2$— may be substituted with —O—, —CH=CH—, cycloalkylene or cycloalkenylene. The preferred examples of the alkyl are non-substituted alkyl having a carbon atom number of 1 to 30, alkoxyalkyl having a carbon atom number of 2 to 29, alkyl which has a carbon atom number of 1 to 8 and in which one —$CH_2$— is substituted with cycloalkylene, alkenyl having a carbon atom number of 2 to 20, alkenyloxyalkyl having a carbon atom number of 3 to 20, alkyloxyalkenyl having a carbon atom number of 3 to 20, alkyl which has a carbon atom number of 1 to 8 and in which one —$CH_2$— is substituted with cycloalkenylene and groups in which optional hydrogen in the groups given above are substituted with fluorine. Cycloalkylene and cycloalkenylene have a preferred carbon atom number of 3 to 8.

The examples of non-substituted alkyl having a carbon atom number of 1 to 30 are methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethylpentyl, nonyl, decyl, undecyl, dodecyl, tetradecyl, hexadecyl, octadecyl, eicosyl, docosyl and triacontyl.

The examples of fluorinated alkyl having a carbon atom number of 1 to 30 are 2-fluoroethyl, 2,2-difluoroethyl, 3,3,3-trifluoropropyl, hexafluoropropyl, nonafluoro-1,1,2,2-tetrahydrohexyl, tridecafluoro-1,1,2,2-tetrahydrooctyl, heptadecafluoro-1,1,2,2-tetrahydrodecyl, perfluoro-1H,1H,2H,2H-dodecyl and perfluoro-1H,1H,2H,2H-tetradecyl.

The examples of alkoxyalkyl and fluorinated alkoxyalkyl each having a carbon atom number of 2 to 29 are 3-methoxypropyl, methoxyethoxyundecyl, 2-fluoroethyloxypropyl, 2,2,2-trifluoroethyloxypropyl, 2-fluoro-1-fluoromethylethyloxypropyl, 2,2,3,3-tetrafluoropropyloxypropyl, 2,2,3,3,3-pentafluoropropyloxypropyl, hexafluoroisopropyloxypropyl, heptafluoroisopropyloxypropyl, hexafluorobutyloxypropyl, heptafluorobutyloxypropyl, octafluoroisobutyloxypropyl, octafluoropentyloxypropyl, 2-fluoroethyloxybutyl, 2,2,2-trifluoroethyloxybutyl, 2-fluoro-1-fluoromethylethyloxybutyl, 2,2,3,3-tetrafluoropropyloxybutyl, 2,2,3,3,3-pentafluoropropyloxybutyl, hexafluoroisopropyloxybutyl, hexafluorobutyloxybutyl, heptafluorobutyloxybutyl, octafluoroisobutyloxybutyl, octafluoropentyloxybutyl, 2-fluoroethyloxyisobutyl, 2,2,2-trifluoroethyloxyisobutyl, 2-fluoro-1-fluoromethylethyloxyisobutyl, 2,2,3,3-tetrafluoropropyloxyisobutyl, 2,2,3,3,3-pentafluoropropyloxyisobutyl, hexafluoroisopropyloxyisobutyl, hexafluorobutyloxyisobutyl, heptafluorobutyloxyisobutyl, octafluoroisobutyloxyisobutyl and octafluoropentyloxyisobutyl.

The examples of alkyl which has a carbon atom number of 1 to 8 and in which one —$CH_2$— is substituted with cycloalkylene are cyclohexylmethyl, adamantaneethyl, cyclopentyl, cyclohexyl, 2-bicycloheptyl and cyclooctyl. Cyclohexyl is an example in which —$CH_2$— in methyl is substituted with cyclohexylene. Cyclohexylmethyl is an example in which —$CH_2$— of a 3 position in ethyl is substituted with cyclohexylene.

The examples of alkenyl having a carbon atom number of 2 to 20 are vinyl, 2-propenyl, 3-butenyl, 5-hexenyl, 7-octenyl, 10-undecenyl and 21-docosenyl. The example of alkenyloxyalkyl having a carbon atom number of 3 to 20 is allyloxyundecyl. The examples of alkyl which has a carbon atom number of 1 to 8 and in which one —$CH_2$— is substituted with cycloalkenylene are 2-(3-cyclohexenyl)ethyl, 5-(bicycloheptenyl)ethyl, 2-cyclopentenyl, 3-cyclohexenyl, 5-norbornene-2-yl and 4-cyclooctenyl.

The examples of a case where $R^1$ in Formula (1) is substituted or non-substituted aryl are phenyl in which optional hydrogen may be substituted with halogen or alkyl having a carbon atom number of 1 to 10 and non-substituted naphthyl. The preferred examples of halogen are fluorine, chlorine and bromine. In alkyl which is a substituent of phenyl, optional hydrogen may be substituted with fluorine, and optional —$CH_2$— may be substituted with —O—, —CH=CH— or phenylene. That is, the specific examples of the preferred aryl are phenyl, non-substituted naphthyl, alkylphenyl, alkyloxyphenyl, alkenylphenyl, phenyl having as a substituent, alkyl in which at least one —$CH_2$— is substituted with phenylene and groups in which optional hydrogen is substituted with halogen in the above groups. In the present invention, phenyl means non-substituted phenyl unless otherwise described.

The examples of halogenated phenyl are pentafluorophenyl, 4-chlorophenyl and 4-bromophenyl.

The examples of the alkylphenyl are 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl and 2,4,6-tris(1-methylethyl)phenyl.

The examples of alkyloxyphenyl are (4-methoxy)phenyl, (4-ethoxy)phenyl, (4-propoxy)phenyl, (4-butoxy)phenyl, (4-pentyloxy)phenyl, (4-heptyloxy)phenyl, (4-decyloxy)phenyl, (4-octadecyloxy)phenyl, 4-(1-methylethoxy)phenyl, 4-(2-methylpropoxy)phenyl and 4-(1,1-dimethylethoxy)phenyl. The examples of alkenylphenyl are 4-vinylphenyl, 4-(1-methylvinyl)phenyl and 4-(3-butenyl)phenyl.

The examples of phenyl having as a substituent, alkyl in which at least one —CH$_2$— is substituted with phenylene are 4-(2-phenylvinyl)phenyl, 4-phenoxyphenyl, 3-(phenylmethyl)phenyl, biphenyl and terphenyl. 4-(2-Phenylvinyl)phenyl is an example in which one —CH$_2$— in ethyl of ethylphenyl is substituted with phenylene and in which the other —CH$_2$— is substituted with —CH=CH—.

The examples of phenyl in which a part of hydrogens on a benzene ring is substituted with halogen and in which the other hydrogens are substituted with alkyl, alkyloxy or alkenyl are 3-chloro-4-methylphenyl, 2,5-dichloro-4-methylphenyl, 3,5-dichloro-4-methylphenyl, 2,3,5-trichloro-4-methylphenyl, 2,3,6-trichloro-4-methylphenyl, 3-bromo-4-methylphenyl, 2,5-dibromo-4-methylphenyl, 3,5-dibromo-4-methylphenyl, 2,3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, 2,3-difluoro-4-propoxyphenyl and 4-vinyl-2,3,5,6-tetrafluorophenyl.

Next, the examples of a case where R$^1$ in Formula (1) is substituted or non-substituted arylalkyl shall be given. In an alkylene group of the arylalkyl, optional hydrogen may be substituted with fluorine, and optional —CH$_2$— may be substituted with —O—, —CH=CH— or cycloalkylene. The preferred example of the arylalkyl is phenylalkyl. In this case, optional hydrogen of the phenyl group may be substituted with halogen or alkyl having a carbon atom number of 1 to 12. In the above alkyl, optional hydrogen may be substituted with fluorine, and optional —CH$_2$— may be substituted with —O—, —CH=CH—, cycloalkylene or phenylene. The preferred carbon number of the alkylene group is 1 to 12, and the more preferred carbon number is 1 to 8.

The examples of non-substituted phenylalkyl are phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl and 1-phenylhexyl.

The examples of phenylalkyl in which at least one hydrogen on a phenyl group is substituted with fluorine are 4-fluorophenylmethyl, 2,3,4,5,6-pentafluorophenylmethyl, 2-(2,3,4,5,6-pentafluorophenyl)ethyl, 3-(2,3,4,5,6-pentafluorophenyl)propyl, 2-(2-fluorophenyl)propyl and 2-(4-fluorophenyl)propyl.

The examples of phenylalkyl in which at least one hydrogen on a phenyl group is substituted with chlorine are 4-chlorophenylmethyl, 2-chlorophenylmethyl, 2,6-dichlorophenylmethyl, 2,4-dichlorophenylmethyl, 2,3,6-trichlorophenylmethyl, 2,4,6-trichlorophenylmethyl, 2,4,5-trichlorophenylmethyl, 2,3,4,6-tetrachlorophenylmethyl, 2,3,4,5,6-pentachlorophenylmethyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl, 4-(2,4,5-trichlorophenyl)butyl, 1-(3-chlorophenyl)ethyl, 1-(4-chlorophenyl)ethyl, 2-(4-chlorophenyl)propyl, 2-(2-chlorophenyl)propyl and 1-(4-chlorophenyl)butyl.

The examples of phenylalkyl in which at least one hydrogen on a phenyl group is substituted with bromine are 2-bromophenylmethyl, 4-bromophenylmethyl, 2,4-dibromophenylmethyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl and 2-(4-bromophenyl)propyl.

The examples of phenylalkyl in which at least one hydrogen on a phenyl group is substituted with alkyl having a carbon atom number of 1 to 12 are 2-methylphenylmethyl, 3-methylphenylmethyl, 4-methylphenylmethyl, 4-dodecylphenylmethyl, 3,5-dimethylphenylmethyl, 2-(4-methylphenyl)ethyl, 2-(3-methylphenyl)ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethylphenyl)propyl, 2-(2,4-dimethylphenyl)propyl, 2-(3,4-dimethylphenyl)propyl, 2-(2,5-dimethylphenyl)butyl, (4-(1-methylethyl)phenyl)methyl, 2-(4-(1,1-dimethylethyl)phenyl)ethyl, 2-(4-(1-methylethyl)phenyl)propyl and 2-(3-(1-methylethyl)phenyl)propyl.

The examples of phenylalkyl having as a substituent for a phenyl group, alkyl which has a carbon atom number of 1 to 12 and in which at least one hydrogen is substituted with fluorine are 3-(trifluoromethyl)phenylmethyl, 2-(4-trifluoromethylphenyl)ethyl, 2-(4-nonafluorobutyl-phenyl)ethyl, 2-(4-tridecafluorohexylphenyl)ethyl, 2-(4-heptadecafluorooctylphenyl)ethyl, 1-(3-trifluoromethylphenyl)ethyl, 1-(4-trifluoromethyl-phenyl)ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl)propyl, 1-methyl-1-(4-nonafluorobutylphenyl)ethyl, 2-(4-tridecafluorohexylphenyl)propyl, 1-methyl-1-(4-tridecafluorohexyl-phenyl)ethyl, 2-(4-heptadecafluorooctylphenyl)propyl and 1-methyl-1-(4-heptadecafluorooctylphenyl)ethyl.

The examples of phenylalkyl having as a substituent for a phenyl group, alkyl which has a carbon atom number of 1 to 12 and in which one —CH$_2$— is substituted with —CH=CH— are 2-(4-vinylphenyl)ethyl, 1-(4-vinylphenyl)ethyl and 1-(2-(2-propenyl)phenyl)ethyl.

The examples of phenylalkyl having as a substituent for a phenyl group, alkyl which has a carbon atom number of 1 to 12 and in which one —CH$_2$— is substituted with —O— are 4-methoxyphenylmethyl, 3-methoxyphenylmethyl, 4-ethoxyphenylmethyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, 2-(3-methoxymethyl)phenyl)ethyl and 3-(2-nonadecafluorodecenyloxyphenyl)propyl.

The examples of phenylalkyl having as a substituent for a phenyl group, alkyl having a carbon atom number of 1 to 12 in which one —CH$_2$— is substituted with cycloalkylene and in which another —CH$_2$— may be substituted with —O— are cyclopentylphenylmethyl, cyclopentyloxyphenylmethyl, cyclohexylphenylmethyl, cyclohexylphenylethyl, cyclohexylphenylpropyl and cyclohexyloxyphenylmethyl.

The examples of phenylalkyl having as a substituent for a phenyl group, alkyl having a carbon atom number of 1 to 12 in which one —CH$_2$— is substituted with phenylene and in which another —CH$_2$— may be substituted with —O— are 2-(4-phenoxyphenyl)ethyl, 2-(4-phenoxyphenyl)propyl, 2-(2-phenoxyphenyl)propyl, 4-biphenylylmethyl, 3-biphenylylethyl, 4-biphenylylethyl, 4-biphenylylpropyl, 2-(2-biphenylyl)propyl and 2-(4-biphenylyl)propyl.

The examples of phenylalkyl in which at least two hydrogens on a phenyl group are substituted with different groups are 3-(2,5-dimethoxy-3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmethyl, 2,3-dichloro-4-methylphenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenylmethyl, (2,3,4,6-tetrachloro-5-methylphenyl)methyl, 2,3,4,5-tetrachloro-6-methylphenylmethyl, 4-chloro-3,5-dimethylphenylmethyl, 2-chloro-3,5-dimethylphenylmethyl, 2,4-dichloro-3,5-dimethylphenylmethyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenylmethyl, 6-bromo-2-methylphenylmethyl, 3-bromo-4-methylphenylmethyl, 2,3-dibromo-4-methylphenylmethyl, 2,3,5-tribromo-4-methylphenylmethyl, 2,3,5,6-tetrabromo-4-methylphenylmethyl and 11-(3-chloro-4-methoxyphenyl)undecyl.

The most preferred examples of a phenyl group in the phenylalkyl are a non-substituted phenyl group and a phenyl group having at least one of fluorine, alkyl having a carbon atom number of 1 to 4, vinyl and methoxy as a substituent.

The examples of phenylalkyl in which at least one —CH$_2$— in an alkylene group constituting the phenylalkyl is substituted with —O—, —CH=CH— or cycloalkylene are 3-phenoxypropyl, 1-phenylvinyl, 2-phenylvinyl, 3-phenyl-2-propenyl, 4-phenyl-4-pentenyl, 13-phenyl-12-tridecenyl, phenylcyclohexyl and phenoxycyclohexyl.

The examples of phenylalkenyl in which hydrogen on a phenyl group is substituted with fluorine or methyl are 4-fluorophenylvinyl, 2,3-difluorophenylvinyl, 2,3,4,5,6-pentafluorophenylvinyl and 4-methylphenylvinyl.

The more preferred specific examples of R$^1$ are ethyl, 2-fluoroethyl, 2,2-difluoroethyl, propyl, 3,3,3-trifluoropropyl, hexafluoropropyl, 2-methylpropyl, 2,4,4-trimethylpentyl, tridecafluoro-1,1,2,2-tetrahydrooctyl, cyclopentyl, cyclohexyl, phenyl, phenyl halide, methylphenyl, dimethylphenyl, methoxyphenyl, non-substituted naphthyl, phenylmethyl, phenylethyl, phenylbutyl, 2-phenylpropyl, 1-methyl-2-phenylethyl, pentafluorophenylpropyl, 4-ethylphenylethyl, 3-ylphenylethyl, 4-(1,1-dimethylethyl)phenylethyl, 4-vinylphenylethyl, 1-(4-vinylphenyl)ethyl, 4-methoxyphenylpropyl and phenoxypropyl.

The further preferred example of R$^1$ is phenyl.

In the present invention, R$^1$ may be a group used for controlling assignment of liquid crystal. The examples thereof are shown below.

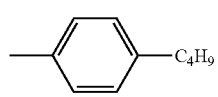

1

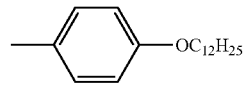

2

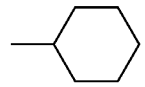

3

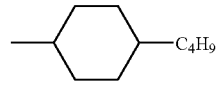

4

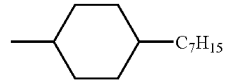

5

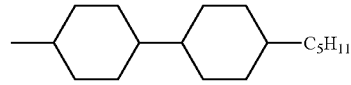

6

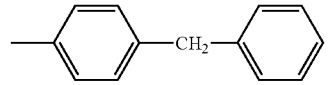

7

8

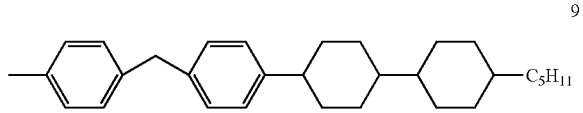

9

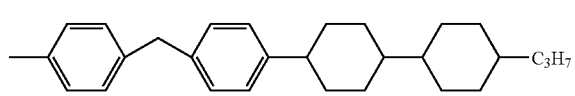

10

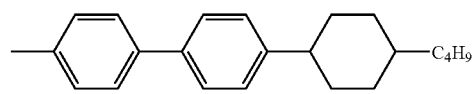

11

A group having a steroid skeleton may be present in a group used for controlling the assignment. Capable of being given as such group having a steroid skeleton are cholesteryl, androsteryl, β-cholesteryl, epiandrosteryl, ergosteryl, estryl, 11-α-hydroxymethylsteryl, 11-α-progesteryl, thenosteryl, melatranyl, methyltestosteryl, noretisteryl, pregnenonyl, β-sitosteryl, stigmasteryl, testostery and cholesterol acetate. These groups may be bonded to silicon via phenyl and may be groups bonded directly to silicon.

R$^2$ and R$^3$ in Formula (1) are independently alkyl having a carbon atom number of 1 to 8, phenyl or cyclohexyl. The examples of the alkyl are methyl, ethyl, propyl, isopropyl, butyl, isobutyl, pentyl, 2-methylbutyl, hexyl, 2-methylpentyl, heptyl, 2-methylhexyl, octyl, 2-methylheptyl and 2-ethylhexyl. And the preferred example of alkyl is methyl.

A in Formula (1) is a group having a polymerization initiating ability for a monomer, preferably a living radical polymerization initiating ability. The examples of such A are a group having an α-haloester group, a group having a halogenated sulfonyl group, a group having a haloalkylphenyl group, a group having an MgBr group, a group having a dithiocarbamate group and a group having a nitroxyl group. The group having a haloalkylphenyl group generates a radical in the presence of a copper chloride/amine complex, and it is an initiator for cationic polymerization in the coexistence of silver perchlorate. The examples of the haloalkylphenyl group are chloromethylphenyl, bromomethylphenyl and iodomethylphenyl.

The MgBr group can be introduced in the following manner. First, a silsesquioxane derivative having a double bond such as a styryl group and a vinyl group is synthesized. Next, a borane-dimethyl sulfide complex is used to carry out hydroboration of a double bond part in the above derivative to prepare a silsesquioxane derivative having boron. Then, this silsesquioxane derivative having boron is reacted with pentane-1,5-diyl-di(magnesium bromide), whereby an MgBr group can be introduced. The silsesquioxane derivative of a Grignard type thus obtained can be used as an anionic polymerization initiator for styrene and methyl (meth)acrylate.

A nitroxyl group can be introduced in the following manner. First, a silsesquioxane derivative having a styryl group is synthesized. Added thereto is a nitroxide compound producing a stable radical which does not take part in polymerization, for example, di-t-butyl nitroxide, 2,2,6,6-tetramethylpiperidinyl-1-oxy or N-t-butyl-1-diethylphosphone-2,2-dimethylpropyl nitroxide, and further introduced thereinto is (N,N'-bis(3,5-di-t-butylsalicylidene)-1,2-cyclohexanediaminate)manganese (III) chloride (Jacobsen catalyst). Next, di-t-butyl peroxide and sodium boron hydride are allowed to be coexistent as a radical-generating agent, whereby a styryl radical is generated, and the intended nitroxyl group can be introduced. The silsesquioxane derivative thus obtained can be used as a polymerization initiating agent for styrene and (meth)acrylate.

Included as well in A in Formula (1) is an exchange chain transfer radical polymerization initiating group represented by reversible addition-fragmentation chain transfer (RAFT). The example of such A is a group having a dithioester group.

A dithioester group can be introduced in the following manner. Benzyl bromide is reacted with metal magnesium to thereby produce phenylmagnesium bromide, and carbon disulfide is added thereto to thereby produce dithiophenyl-magnesium bromide. Then, the above compound is reacted with a silsesquioxane derivative having a haloalkylphenyl group or an α-haloester group, whereby the intended dithioester group can be introduced. The silsesquioxane derivative thus obtained can be used as an exchange chain transfer radical polymerization initiator for styrene, acrylate, methyl (meth)acrylate, acrylic acid, styrenesulfonic acid, methyl(meth)acrylamide and N-isopropylacrylamide.

The preferred examples of A are a group having an α-haloester group, a group having a halogenated sulfonyl group, a group having a haloalkylphenyl group and a group having a dithiocarbamate group.

The group having an α-haloester group means a group having α-halocarbonyloxy at an end. An atom transfer radical polymerization method is known as a polymerization method using the above α-halocarbonyloxy as a group for initiating radical polymerization. A polymerization catalyst used in the above method is a metal complex comprising an 8th group, 9th group, 10th group or 11th group element in the periodic table as a central metal atom. In this atom transfer radical polymerization, it is known that a group having α-halocarbonyloxy has an excellent polymerization initiating ability. It is well known as well that the above polymerization is similar to living polymerization. That is, the silicon compound of the present invention having an α-haloester group has an excellent polymerization initiating ability in the presence of a transition metal complex and can continue to maintain a living polymerizability. It can initiate polymerization for all radically polymerizable monomers. In particular, it can reveal an excellent living polymerizability to (meth)acrylic acid derivatives or styrene base derivatives.

The silicon compound of the present invention having an α-haloester group has an α-halocarbonyloxy group at an end, and therefore it can be derived into a lot of derivatives by applying various organic reactions. For example, it can be derived into a silsesquioxane derivative having an organic metal functional group by reacting the above silicon compound with lithium, magnesium or zinc. To be specific, the silicon compound of the present invention having an α-haloester group is reacted with zinc to be derived into a silsesquioxane derivative having an organic zinc functional group, and then aldehyde and ketone are added thereto, whereby it can be converted into alcohols. Accordingly, the silsesquioxane derivative having an organic zinc functional group is useful as an intermediate raw material used for a so-called Lifomackey reaction.

An α-halocarbonyloxy group has a strong electrophilicity, and therefore it can be converted into an amino group and a mercapto group using various nucleophilic reagents. Further, an α-halocarbonyloxy group is treated with enamine to be converted into an imine salt, and this imine salt is hydrolyzed, whereby it can be converted into ketone. That is, the silicon compound of the present invention having an α-halocarbonyloxy group is also useful as an intermediate raw material used for a stoke-enamine reaction. Silsesquioxane derivatives having various organic functional groups and polymerizable functional groups can be prepared as well by reacting the above silicone compound with aliphatic or aromatic Grignard reagents. Accordingly, the silicon compound of the present invention having an α-halocarbonyloxy group can be used not only as a polymerization initiator but also as an intermediate useful for various organic syntheses.

The preferred example of the silicon compound of the present invention having an α-haloester group is a compound represented by Formula (1-1):

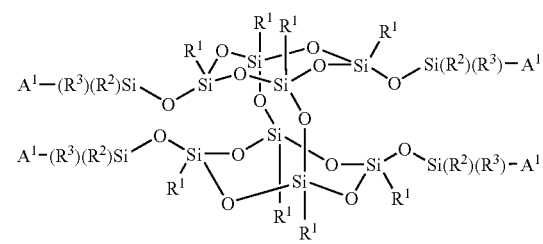

(1-1)

$R^1$, $R^2$ and $R^3$ in Formula (1-1) have the same meanings as those of these codes in Formula (1), and $A^1$ is a group represented by Formula (2-1):

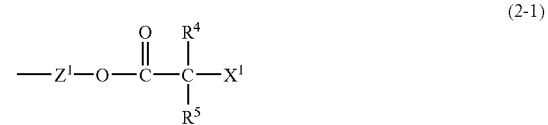

(2-1)

In Formula (2-1), $X^1$ is halogen, and the examples thereof are chlorine, bromine and iodine. Chlorine and bromine are most preferred as an initiating group for atom transfer radical polymerization. $R^4$ is hydrogen, alkyl having a carbon atom number of 1 to 20, aryl having a carbon atom number of 6 to 20 or arylalkyl having a carbon atom number of 7 to 20. The preferred examples of $R^4$ are hydrogen, alkyl having a carbon atom number of 1 to 20, phenyl in which optional hydrogen may be substituted with alkyl having a carbon atom number of 1 to 14 and phenylalkyl constituted from a phenyl group in which optional hydrogen may be substituted with alkyl having a carbon atom number of 1 to 14 and an alkylene group having a carbon atom number of 1 to 14, wherein the total number of carbon atoms in the above groups is 7 to 20. The more preferred examples of $R^4$ are hydrogen and alkyl having a carbon atom number of 1 to 20. The further preferred examples of $R^4$ are hydrogen, methyl and ethyl, and the most preferred example is methyl. $R^5$ is alkyl having a carbon atom number of 1 to 20, aryl having a carbon atom number of 6 to 20 or arylalkyl having a carbon atom number of 7 to 20. The preferred examples of $R^5$ are alkyl having a carbon atom number of 1 to 20, phenyl in which optional hydrogen may be substituted with alkyl having a carbon atom number of 1 to 14 and phenylalkyl constituted from a phenyl group in which optional hydrogen may be substituted with alkyl having a carbon atom number of 1 to 14 and an alkylene group having a carbon atom number of 1 to 14, wherein the total number of carbon atoms in the above groups is 7 to 20. The more preferred example of $R^5$ is alkyl having a carbon atom number of 1 to 20. The further preferred examples of $R^5$ are methyl and ethyl, and the most preferred example is methyl. $Z^1$ is alkylene having a carbon atom number of 2 to 20 or alkenylene having a carbon atom number of 3 to 8. Optional —$CH_2$— in these alkylene and alkenylene may be substituted with —O—.

In bonding an organic group to an Si atom, representative methods for obtaining the derivative which is not hydrolyzed are a method in which a Grignard reagent is reacted with Si-halogen and a method in which a compound having an aliphatic unsaturated bond is reacted with Si—H. The latter is usually called a hydrosilylation reaction method. In the present invention, the hydrosilylation reaction method is rather liable to be applied in terms of an easiness in obtaining the raw materials. That is, a preferred method for introducing a functional group into a silsesquioxane derivative is a method in which an Si—H functional silsesquioxane derivative is combined with a compound having an unsaturated bond at a terminal by the hydrosilylation reaction. Accordingly, the preferred example of $Z^1$ in Formula (2-1) is a group represented by —$C_2H_4$—$Z^8$. That is, the preferred example of Formula (2-1) is Formula (2-1-4):

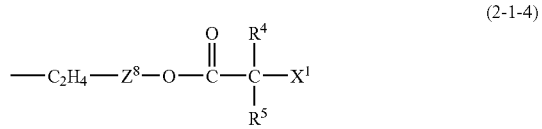

(2-1-4)

In Formula (2-1-4), $Z^8$ is a single bond or alkylene having a carbon atom number of 1 to 8, and optional —$CH_2$— in this alkylene may be substituted with —O—.

That is, the preferred example of $Z^1$ is alkylene which has a carbon atom number of 2 to 10 and in which optional —$CH_2$— may be substituted with —O—. The examples of such alkylene are —$C_2H_4$—, —$C_3H_6$—, —$C_4H_8$—, —$C_5H_{10}$—, —$C_2H_4$—O—$C_3H_6$— and —$C_3H_6$—O— $C_3H_6$—. The more preferred examples of $Z^1$ are —$C_3H_6$—, —$C_4H_8$—, —$C_5H_{10}$— and —$C_2H_4$—O—$C_3H_6$—. However, the selected range of $Z^1$ shall not be restricted to them. The codes other than $Z^8$ have the same meanings as those of these codes in Formula (2-1).

An atom transfer radical polymerization method is known as a polymerization method using a halogenated sulfonyl group as a group for initiating radical polymerization. In this method, a metal complex comprising an 8th group, 9th group, 10th group or 11th group element in the periodic table as a central metal is used as a catalyst. In this atom transfer radical polymerization, it is known that halogenated sulfonyl has an excellent polymerization initiating ability. Further, it is well known as well that this polymerization is similar to living polymerization. That is, the silicon compound of the present invention having halogenated sulfonyl has an excellent polymerization initiating ability in the presence of a transition metal catalyst and can continue to maintain a living polymerizability. It can initiate polymerization for all radically polymerizable monomers. In particular, it can reveal an excellent living polymerizability to (meth)acrylic acid derivatives.

A halogenated sulfonyl group has a strong electrophilicity, and therefore various derivatives can be synthesized by making use of various electrophilic reagents for the silicon compound of the present invention having a halogenated sulfonyl group. Possible are, for example, conversion to sulfonic aid by hydrolysis under an acid condition, conversion to sulfonic aid by hydrolysis and then conversion to a sulfonic aid salt by treatment with sodium hydroxide, conversion to sulfonic aid esters by treatment with various alcohols under a basic condition and conversion to sulfonic aid amides by treatment with ammonia or amines. The above characteristics make it possible to make use of the silicon compound of the present invention as a protective group and make it possible to make use of a part of sulfonic aid amide derivatives as a sulfa agent, for example, a fungicide. Further, it can be converted to a mercapto group using various reducing agents, for example, aluminum lithium hydride, and it can be derived into aromatic sulfone by various aromatic Grignard reagents. That is, the above silicon compound can efficiently be used not only as an attribute for a polymerization initiator but also as an intermediate useful for organic synthesis.

The preferred examples of the silicon compound of the present invention having halogenated sulfonyl is a compound represented by Formula (1-2):

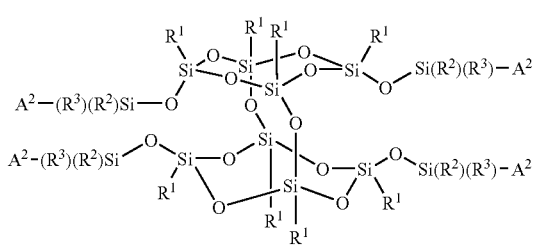

(1-2)

$R^1$, $R^2$ and $R^3$ in Formula (1-2) have the same meanings as those of these codes in Formula (1), and $A^2$ is a group represented by Formula (2-2):

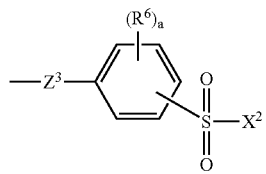

(2-2)

In Formula (2-2), $X^2$ is halogen, and the examples thereof are chlorine, bromine and iodine. Chlorine and bromine are most preferred as an initiating group for atom transfer radical polymerization. $Z^3$ is alkylene having a carbon atom number of 2 to 10, and optional —$CH_2$— in this alkylene may be substituted with —O— or —COO—. A bonding position of —$SO_2X^2$ on the benzene ring is an ortho position, a meta position or a para position to a bonding position of $Z^3$. $R^6$ is alkyl having a carbon atom number of 1 to 3. The code of a showing the number of $R^6$ is 0, 1 or 2, and zero is most preferred. A bonding position of $R^6$ is an optional position excluding the respective bonding positions of $Z^3$ and —$SO_2X^2$.

$Z^2$ in Formula (2-2) is preferably a group represented by —$C_2H_4$—$Z^9$ as is the case with Formula (2-1). That is, the preferred example of Formula (2-2) is Formula (2-2-4):

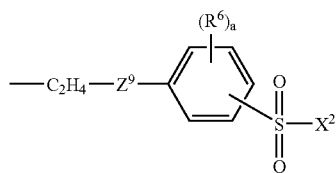

(2-2-4)

In Formula (2-2-4), $Z^9$ is a single bond or alkylene having a carbon atom number of 1 to 3.

That is, the preferred example of $Z^3$ is alkylene having a carbon atom number of 2 to 5. The examples of such alkylene are —$C_2H_4$—, —$C_3H_6$—, —$C_4H_8$— and —$C_5H_{10}$—. The most preferred example of $Z^3$ is —$C_2H_4$—. However, the selected range of $Z^3$ shall not be restricted to them. In Formula (2-2-4), the codes other than $Z^9$ have the same meanings as those of the codes in Formula (2-2), and the bonding positions of the halogenated sulfonyl group and $R^6$ to $Z^9$ on the benzene ring are the same as these bonding positions to $Z^3$ in Formula (2-2).

An atom transfer radical polymerization method is known as a polymerization method using haloalkylpheny as a group for initiating radical polymerization. In this method, a metal complex comprising an 8th group, 9th group, 10th group or 11th group element in the periodic table as a central metal is used as a catalyst. In this atom transfer radical polymerization, it is known that haloalkylphenyl has an excellent polymerization initiating ability. Further, it is well known as well that this polymerization is similar to living polymerization. That is, the silicon compound of the present invention having haloalkylphenyl has an excellent polymerization initiating ability in the presence of a transition metal catalyst and can continue to maintain a living polymerizability. It can initiate polymerization for all radically polymerizable monomers. In particular, it can reveal an excellent living polymerizability to styrene base derivatives.

A haloalkylphenyl has a strong electrophilicity, and therefore an amino group, a hydroxyl group and a mercapto group can be introduced into the silicon compound of the present invention having haloalkylphenyl by making use of various electrophilic reagents. That is, this silicon compound can efficiently be used as a useful intermediate.

The preferred examples of the silicon compound of the present invention having haloalkylphenyl is a compound represented by Formula (1-3):

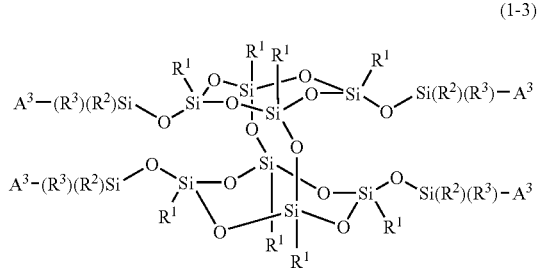

(1-3)

$R^1$, $R^2$ and $R^3$ in Formula (1-3) have the same meanings as those of these codes in Formula (1), and $A^3$ is a group represented by

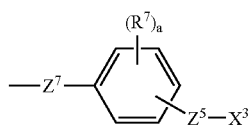

(2-3)

$X^3$ in Formula (2-3) is halogen such as chlorine, bromine and iodine. Chlorine and bromine are more preferred as an initiating group in atom transfer radical polymerization. $Z^5$ is alkylene having a carbon atom number of 1 to 3. The examples of $Z^5$ are methylene, 1,2-ethylene, 1,1-ethylene, 1,3-trimethylene, ethylmethylene, 1-methyl-1,2-ethylene and 2-methyl-1,2-ethylene. The preferred example of $Z^5$ is methylene.

$Z^7$ is alkylene having a carbon atom number of 2 to 10. In this alkylene, one —$CH_2$— may be substituted with —O—. A bonding position of $Z^5$ on the benzene ring is a meta position or a para position to a bonding position of $Z^7$. $R^7$ is alkyl having a carbon atom number of 1 to 3. The examples of $R^7$ are methyl, ethyl, propyl and isopropyl. Preferred $R^7$ is methyl. The term a showing the number of $R^7$ is 0, 1 or 2, and a is preferably 0. A bonding position of $R^7$ on the benzene ring is an optional position excluding the bonding positions of $Z^5$ and $Z^7$.

$Z^7$ in Formula (2-3) is preferably a group represented by —$C_2H_4$—$Z^{10}$ as is the case with Formula (2-1). That is, the preferred example of Formula (2-3) is Formula (2-3-4):

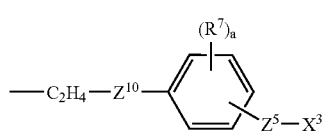

(2-3-4)

$Z^{10}$ in Formula (2-3-4). is a single bond or alkylene which has a carbon atom number of 1 to 8 and in which one —CH$_2$— may be substituted with —O—.

That is, the preferred example of $Z^7$ in Formula (2-1) is alkylene which has a carbon atom number of 2 to 10 and in which one —CH$_2$— may be substituted with —O—. The examples of such $Z^7$ are —C$_2$H$_4$—, —C$_3$H$_6$—, —OC$_2$H$_4$—, —OC$_3$H$_6$—, —CH$_2$OC$_2$H$_4$—, —CH$_2$OC$_3$H$_6$—, —C$_2$H$_4$OC$_2$H$_4$— and —C$_2$H$_4$OC$_3$H$_6$—. However, the selected range of $Z^7$ shall not be restricted to them. In Formula (2-3-4), the codes other than $Z^{10}$ have the same meanings as those of the codes in Formula (2-3), and the bonding positions of $Z^5$ and $R^7$ to $Z^{10}$ on the benzene ring are the same as these bonding positions to $Z^7$ in Formula (2-3).

A photo initiator-transfer agent-terminator polymerization method is known as a photopolymerization method using a dithiocarbamate group as a polymerization initiating group. In this photo initiator-transfer agent-terminator polymerization, it is well known that a dithiocarbamate group is radically dissociated by virtue of light and that it has an excellent polymerization initiating ability and sensitizing ability. It is well known as well that this photopolymerization is similar to living polymerization. Accordingly, the silicon compound of the present invention having a dithiocarbamate group can continue to maintain a living polymerizability as long as it is irradiated with light, and it has a photopolymerization initiating ability for all radically polymerizable monomers. In particular, it can reveal an excellent living polymerizability to (meth)acrylic acid derivatives. A dithiocarbamate group has a radiation resistance, a pharmacological activity such as a weeding effect, a complex-forming ability and a hydrophilicity in addition to the characteristics as a photopolymerization initiating group, and therefore it is possible to efficiently use these characteristics.

The preferred example of the silicon compound of the present invention having a dithiocarbamate group is a compound represented by Formula (1-4):

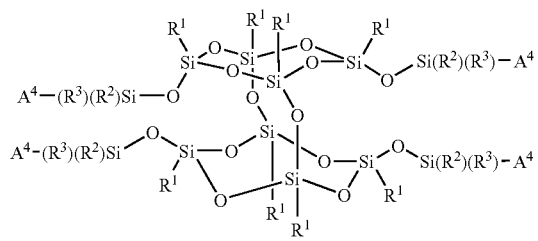

(1-4)

$R^1$, $R^2$ and $R^3$ in Formula (1-4) have the same meanings as those of these codes in Formula (1), and $A^4$ is a group represented by Formula (2-4):

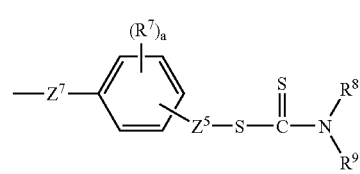

(2-4)

$Z^5$, $Z^7$, $R^7$ and a in Formula (2-4) have the same meanings as those of these codes in Formula (2-3), and the bonding positions of $Z^5$ and $R^7$ on the benzene ring are the same positions in Formula (2-3). $R^8$ and $R^9$ are independently hydrogen, alkyl having a carbon atom number of 1 to 12, cycloalkyl having a carbon atom number of 5 to 10 or aryl having a carbon atom number of 6 to 10. The examples of $R^8$ or $R^9$ other than hydrogen are methyl, ethyl, propyl, isopropyl, butyl, isobutyl, pentyl, 2-methylbutyl, hexyl, 2-methylpentyl, heptyl, 2-methylhexyl, octyl, 2-methylheptyl, 2-ethylhexyl, decyl, phenyl, cyclopentyl and cyclohexyl. Both of $R^8$ and $R^9$ may be one of these groups or one may be one of these groups, and the other may be hydrogen.

$R^8$ and $R^9$ may be combined with each other to form a ring together with N. In this case, the examples of a dithiocarbamate group are N-cyclotrimethylenedithiocarbamate, N-cyclotetramethylenedithiocarbamate, N-cyclopentamethylenedithiocarbamate, N-cyclohexamethylenedithiocarbamate, N-cycloheptamethylenedithiocarbamate and N-cyclooctamethylenedithiocarbamate. The preferred dithiocarbamate groups are N,N-dimethyldithiocarbamate, N,N-diethyldithiocarbamate, N-methyldithiocarbamate and N-ethyldithiocarbamate. N,N-diethyldithiocarbamate is most preferred.

$Z^7$ in Formula (2-4) is preferably a group represented by —C$_2$H$_4$—Z$^{10}$ as is the case with Formula (2-1). That is, the preferred example of Formula (2-4) is Formula (2-4-3):

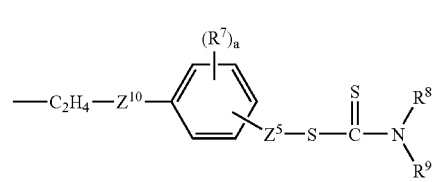

(2-4-3)

In Formula (2-4-3), $Z^{10}$ has the same meaning as that of $Z^{10}$ in Formula (2-3-4), and the codes other than $Z^{10}$ have the same meanings as those of the codes in Formula (2-4). The bonding positions of $Z^5$ and $R^7$ to that of $Z^{10}$ on the benzene ring are the same as the bond positions thereof to $Z^7$ in Formula (2-4).

Next, a part of the specific examples of the compound (1-1), the compound (1-2), the compound (1-3) and the compound (1-4) among the silicon compounds of the present invention shall be shown in Tables 2 to 4 using codes shown in Table 1. These examples are the examples of cases where in the following Formula (1-1-1), Formula (1-2-1), Formula (1-3-1) and Formula (1-4-1), $R^1$ is phenyl; $Z^1$ is —C$_3$H$_6$—, —C$_4$H$_8$—, —C$_5$H$_{10}$— or —C$_2$H$_4$—O—C$_3$H$_6$—; $Z^4$ is a single bond, —CH$_2$—, —C$_2$H$_4$— or —C$_3$H$_6$—; and $Z^6$ is a single bond, —CH$_2$—, —C$_2$H$_4$— or a group in which one —CH$_2$— in the above alkylenes is substituted with —COO—. The above examples are the preferred examples of the silicon compound of the present invention.

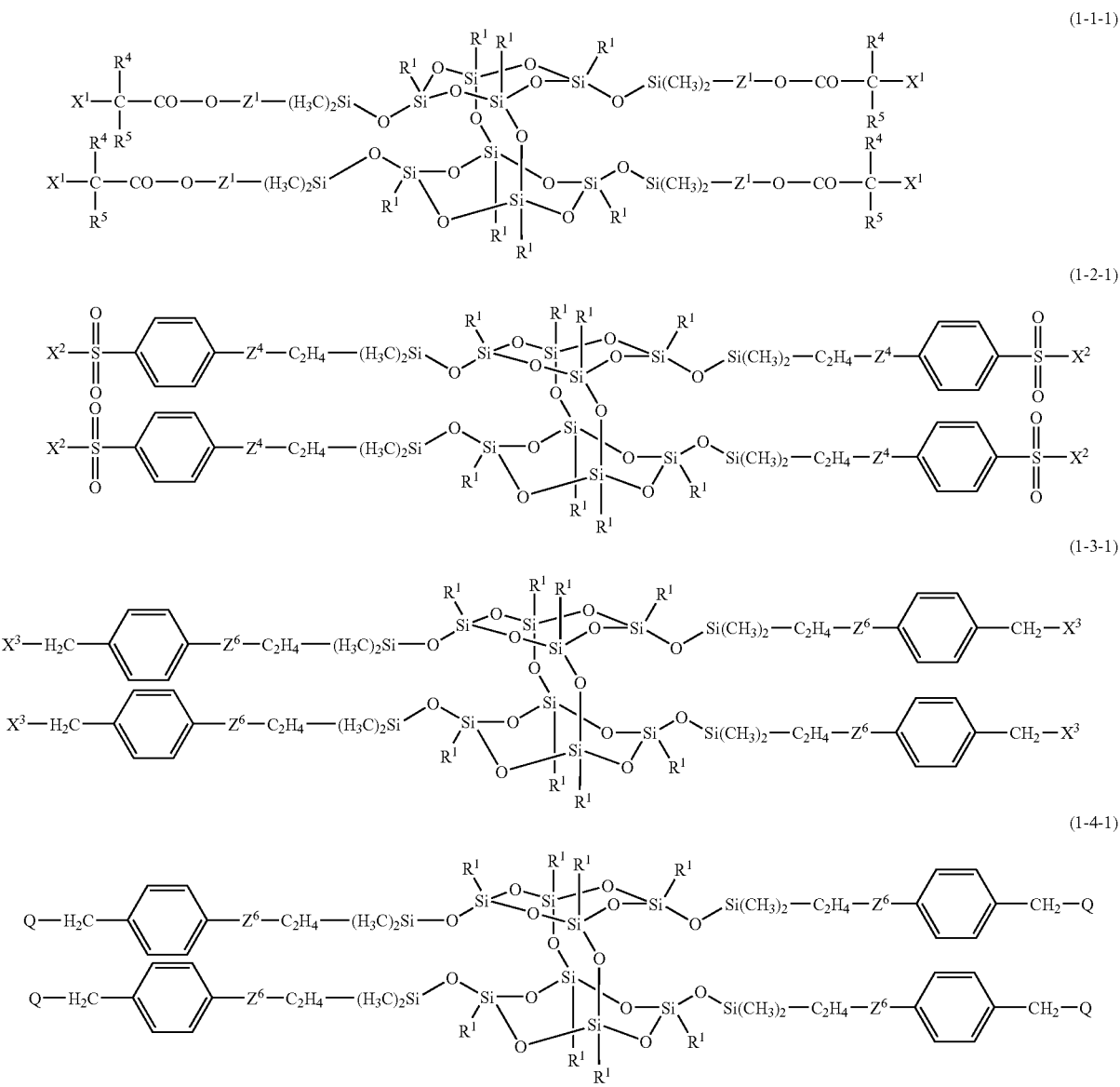
| TABLE 1 | |
|---|---|
| Code | Chemical formula |
| Me | —CH$_3$ |
| Et | —C$_2$H$_5$ |
| B | (phenyl, mono-substituted) |
| Ph | (phenylene, para) |
| — | Single bond |
| C1 | —CH$_2$— |
| C2 | —C$_2$H$_4$— |
| C3 | —C$_3$H$_6$— |
| C4 | —C$_4$H$_8$— |
| C5 | —C$_5$H$_{10}$— |
| C2OC3 | —C$_2$H$_4$—O—C$_3$H$_6$— |
| CL | —Cl |
| BR | —Br |
| DM | —Si(CH$_3$)$_2$— |

TABLE 1-continued

| Code | Chemical formula |
|---|---|
| Q | $(C_2H_5)_2N-C(=S)-S-$ |

TABLE 2

| No. | R1 | Z1 | R4 | R5 | X1 | Formula (1-1-1) |
|---|---|---|---|---|---|---|
| 1 | B | C3 | H | Me | CL | $(B-)_8(CL-CHMe-COO-C3-DM-)_4Si_8O_{14}$ |
| 2 | B | C4 | H | Me | CL | $(B-)_8(CL-CHMe-COO-C4-DM-)_4Si_8O_{14}$ |
| 3 | B | C5 | H | Me | CL | $(B-)_8(CL-CHMe-COO-C5-DM-)_4Si_8O_{14}$ |
| 4 | B | C2OC3 | H | Me | CL | $(B-)_8(CL-CHMe-COO-C2OC3-DM-)_4Si_8O_{14}$ |
| 5 | B | C3 | Me | Me | CL | $(B-)_8(CL-CMe_2-COO-C3-DM-)_4Si_8O_{14}$ |
| 6 | B | C4 | Me | Me | CL | $(B-)_8(CL-CMe_2-COO-C4-DM-)_4Si_8O_{14}$ |
| 7 | B | C5 | Me | Me | CL | $(B-)_8(CL-CMe_2-COO-C5-DM-)_4Si_8O_{14}$ |
| 8 | B | C2OC3 | Me | Me | CL | $(B-)_8(CL-CMe_2-COO-C2OC3-DM-)_4Si_8O_{14}$ |
| 9 | B | C3 | Et | Et | CL | $(B-)_8(CL-CEt_2-COO-C3-DM-)_4Si_8O_{14}$ |
| 10 | B | C4 | Et | Et | CL | $(B-)_8(CL-CEt_2-COO-C4-DM-)_4Si_8O_{14}$ |
| 11 | B | C5 | Et | Et | CL | $(B-)_8(CL-CEt_2-COO-C5-DM-)_4Si_8O_{14}$ |
| 12 | B | C2OC3 | Et | Et | CL | $(B-)_8(CL-CEt_2-COO-C2OC3-DM-)_4Si_8O_{14}$ |
| 13 | B | C3 | H | Me | BR | $(B-)_8(BR-CHMe-COO-C3-DM-)_4Si_8O_{14}$ |
| 14 | B | C4 | H | Me | BR | $(B-)_8(BR-CHMe-COO-C4-DM-)_4Si_8O_{14}$ |
| 15 | B | C5 | H | Me | BR | $(B-)_8(BR-CHMe-COO-C5-DM-)_4Si_8O_{14}$ |
| 16 | B | C2OC3 | H | Me | BR | $(B-)_8(BR-CHMe-COO-C2OC3-DM-)_4Si_8O_{14}$ |
| 17 | B | C3 | Me | Me | BR | $(B-)_8(BR-CMe_2-COO-C3-DM-)_4Si_8O_{14}$ |
| 18 | B | C4 | Me | Me | BR | $(B-)_8(BR-CMe_2-COO-C4-DM-)_4Si_8O_{14}$ |
| 19 | B | C5 | Me | Me | BR | $(B-)_8(BR-CMe_2-COO-C5-DM-)_4Si_8O_{14}$ |
| 20 | B | C2OC3 | Me | Me | BR | $(B-)_8(BR-CMe_2-COO-C2OC3-DM-)_4Si_8O_{14}$ |
| 21 | B | C3 | Et | Et | BR | $(B-)_8(BR-CEt_2-COO-C3-DM-)_4Si_8O_{14}$ |
| 22 | B | C4 | Et | Et | BR | $(B-)_8(BR-CEt_2-COO-C4-DM-)_4Si_8O_{14}$ |
| 23 | B | C5 | Et | Et | BR | $(B-)_8(BR-CEt_2-COO-C5-DM-)_4Si_8O_{14}$ |
| 24 | B | C2OC3 | Et | Et | BR | $(B-)_8(BR-CEt_2-COO-C2OC3-DM-)_4Si_8O_{14}$ |

TABLE 3

| No. | $R^1$ | $Z^4$ | $X^2$ | Formula (1-2-1) |
|---|---|---|---|---|
| 1 | B | — | CL | $(B-)_8(CL-SO_2-Ph-C2-DM-)_4Si_8O_{14}$ |
| 2 | B | C1 | CL | $(B-)_8(CL-SO_2-Ph-C3-DM-)_4Si_8O_{14}$ |
| 3 | B | C2 | CL | $(B-)_8(CL-SO_2-Ph-C4-DM-)_4Si_8O_{14}$ |
| 4 | B | C3 | CL | $(B-)_8(CL-SO_2-Ph-C5-DM-)_4Si_8O_{14}$ |
| 5 | B | — | BR | $(B-)_8(BR-SO_2-Ph-C2-DM-)_4Si_8O_{14}$ |
| 6 | B | C1 | BR | $(B-)_8(BR-SO_2-Ph-C3-DM-)_4Si_8O_{14}$ |
| 7 | B | C2 | BR | $(B-)_8(BR-SO_2-Ph-C4-DM-)_4Si_8O_{14}$ |
| 8 | B | C3 | BR | $(B-)_8(BR-SO_2-Ph-C5-DM-)_4Si_8O_{14}$ |

TABLE 4

| No. | $R^1$ | $Z^6$ | $X^3$ | Formula (1-3-1) |
|---|---|---|---|---|
| 1 | B | — | CL | $(B-)_8(CL-C1-Ph-C2-DM-)_4Si_8O_{14}$ |
| 2 | B | C1 | CL | $(B-)_8(CL-C1-Ph-C3-DM-)_4Si_8O_{14}$ |
| 3 | B | C2 | CL | $(B-)_8(CL-C1-Ph-C4-DM-)_4Si_8O_{14}$ |
| 4 | B | COO | CL | $(B-)_8(CL-C1-Ph-COO-C2-DM-)_4Si_8O_{14}$ |
| 5 | B | COO—C1 | CL | $(B-)_8(CL-C1-Ph-COO-C3-DM-)_4Si_8O_{14}$ |
| 6 | B | — | BR | $(B-)_8(BR-C1-Ph-C2-DM-)_4Si_8O_{14}$ |
| 7 | B | C1 | BR | $(B-)_8(BR-C1-Ph-C3-DM-)_4Si_8O_{14}$ |
| 8 | B | C2 | BR | $(B-)_8(BR-C1-Ph-C4-DM-)_4Si_8O_{14}$ |
| 9 | B | COO | BR | $(B-)_8(BR-C1-Ph-COO-C2-DM-)_4Si_8O_{14}$ |
| 10 | B | COO—C1 | BR | $(B-)_8(BR-C1-Ph-COO-C3-DM-)_4Si_8O_{14}$ |

TABLE 5

| No. | $R^1$ | $Z^6$ | Formula (1-4-1) |
|---|---|---|---|
| 1 | B | — | $(B-)_8(Q-C1-Ph-C2-DM-)_4Si_8O_{14}$ |
| 2 | B | C1 | $(B-)_8(Q-C1-Ph-C3-DM-)_4Si_8O_{14}$ |
| 3 | B | C2 | $(B-)_8(Q-C1-Ph-C4-DM-)_4Si_8O_{14}$ |
| 4 | B | COO | $(B-)_8(Q-C1-Ph-COO-C2-DM-)_4Si_8O_{14}$ |
| 5 | B | COO—C1 | $(B-)_8(Q-C1-Ph-COO-C3-DM-)_4Si_8O_{14}$ |

The compound (1-1), the compound (1-2), the compound (1-3) and the compound (1-4) shall not be restricted by the examples described in Tables 2 to 5.

Next, the production process of the compound (1-1) out of the silicon compounds of the present invention shall be explained:

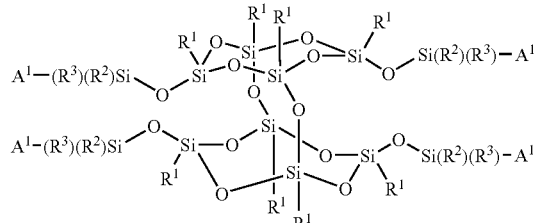

(1-1)

$R^1$, $R^2$ and $R^3$ in Formula (1-1) have the same meanings as those of these codes in Formula (1), and $A^1$ is a group represented by Formula (2-1):

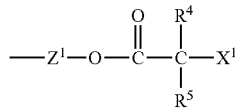
(2-1)

In Formula (2-1), $Z^1$ is alkylene having a carbon atom number of 2 to 20 or alkenylene having a carbon atom number of 3 to 8, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; and $X^1$ is halogen.

The preferred raw material used in the present invention is a compound (3-1):

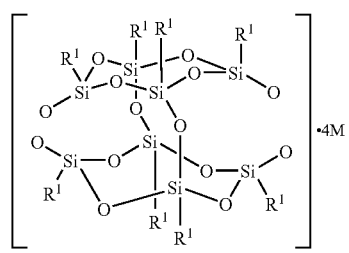
(3-1)

In Formula (3-1), $R^1$ has the same meaning as that of $R^1$ in Formula (1), and M is a monovalent alkali metal atom. The preferred examples of the alkali metal are sodium and potassium. The most preferred example is sodium.

The compound (3-1) can be obtained by hydrolyzing and condensing a silane compound having a trifunctional hydrolyzable group in the presence of an organic solvent, water and alkali metal hydroxide. The compound (3-1) can be produced for short time at a high yield by the above method (refer to, for example, WO03/024870 pamphlet). In producing the compound (3-1), the compound (3-1) in which eight $R^1$'s are constituted from at least two different groups can be obtained by using at least two silane compounds having a trifunctional hydrolyzable group. Since the compound (3-1) shows a high reactivity, use of this compound as a raw material makes it possible to readily synthesize the derivative thereof at a high yield. For example, an Si—H functional silsesquioxane derivative can be produced by reacting the compound (3-1) with Si—H functional diorganochlorosilane.

The Si—H functional diorganochlorosilane is represented by Formula (4). The preferred example of Formula (4) is dimethylchlorosilane. A compound (5) is obtained by reacting the compound (3-1) with the compound (4):

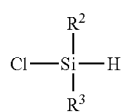
(4)

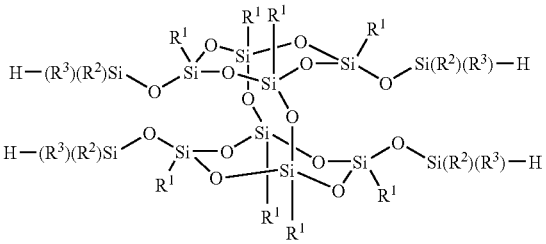
(5)

$R^1$, $R^2$ and $R^3$ in these formulas have the same meanings as those of these codes in Formula (1).

A method making use of nucleophilic displacement can be adopted in order to react the compound (3-1) with the compound (4) to synthesize the compound (5). This method is described in, for example, J. Am. Chem. Soc., 112 (1990), 1931-. Conditions for selecting a solvent used for this nucleophilic displacement reaction are that it is not reacted with the compound (3-1) and the compound (4) and that it is sufficiently dehydrated. The examples of the solvent are tetrahydrofuran, toluene and dimethylforamide. The most preferred solvent is well dehydrated tetrahydrofuran. A preferred use amount of the compound (4) is 3 to 15 times in terms of an equivalent ratio based on the compound (3-1). In this reaction, triethylamine may be used as a catalytic role for allowing the reaction to quickly proceed. When using triethylamine, an amount thereof is preferably 3 to 15 times in terms of an equivalent ratio based on the compound (3-1).

The reaction temperature shall not specifically be restricted as long as side reactions do not take place at the same time and a quantitative nucleophilic reaction goes on. In charging the raw materials, however, the reaction may be carried out under a low temperature condition, for example, in an ice bath. The subsequent reaction may be carried out under a room temperature condition or a heating condition. To be specific, the reaction temperature falls in a range of 0 to 150° C., more preferably in a range of 0 to 50° C. The reaction time shall not specifically be restricted as long as it is time enough for a quantitative nucleophilic reaction to go on. Usually, the intended silicon compound can be obtained in 1 to 15 hours.

Further, the compound (3-1) has —ONa as a reactive group, and therefore hydrogen chloride is not produced when chlorosilanes are used for synthetic reaction of the derivatives. Accordingly, the reaction operation can be facilitated, and the reaction can completely carried out.

Another preferred raw material used in the present invention is a compound (3-2):

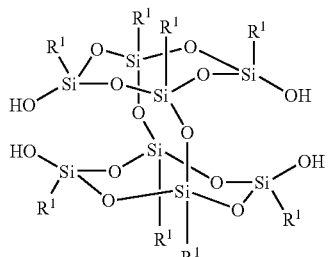
(3-2)

R¹ in Formula (3-2) has the same meaning as that of R¹ in Formula (1). Such compound is readily obtained by reacting the compound (3-1) with an acid. In this case, an organic solvent can be used, if necessary, in reacting with the acid. Capable of being used is a method in which the compound (3-1) is mixed with the organic solvent and in which the acid is dropwise added to this mixture to thereby allow the reaction to proceed.

The organic solvent shall not specifically be restricted as long as it does not hinder the progress of the reaction. It includes, for example, aliphatic hydrocarbons such as hexane and heptane, aromatic hydrocarbons such as benzene, toluene and xylene, ethers such as diethyl ether, tetrahydrofuran and dioxane, halogenated hydrocarbons such as methylene chloride and carbon tetrachloride and acetates such as methyl acetate, ethyl acetate and butyl acetate, and tetrahydrofuran and ethyl acetate are preferred.

A preferred proportion of the compound (3-1) mixed with the organic solvent is 0.05 to 50% by weight based on the weight of the solvent. If it is less than 50% by weight, a concentration of the by-produced salts can be reduced, and it is advantageous for allowing the reaction to proceed. On the other hand, if it is 0.05% by weight or more, the volume efficiency is good, and it is preferred in terms of the cost. The more preferred proportion is 1 to 10% by weight.

The acid used in the above reaction shall not specifically be restricted as long as it is a proton donor (Brinsted acid) and is a compound which can be reacted with the compound (3-1) to obtain the compound (3-2). Capable of being given as the examples thereof are, for example, cyanic acid, isocyanic acid, thiocyanic acid, isothiocyanic acid, nitric acid, nitrous acid, sulfuric acid, sulfurous acid, carbonic acid, hydrochloric acid, hydrobromic acid, phosphoric acid, boric acid, formic acid, acetic acid, propionic acid, butyric acid, stearic acid, oxalic acid, malonic acid, succinic acid, adipic acid, acrylic acid, methacrylic acid, oleic acid, maleic acid, chloroformic acid, chloroacetic acid, trifluoroacetic acid, cyclohexanecarboxylic acid, pivalic acid, benzoic acid, toluic acid, naphthoic acid, phthalic acid, cinnamic acid, nicotinic acid, thiophenecarboxylic acid, S-thioacetic acid, dithioacetic acid, S-thiobenzoic acid, dithiobenzoic acid, thiocarbonic acid, trithiocarbonic acid, xanthic acid, methanesulfonic acid, benzenesulfonic acid, p-toluenesulfonic acid, phenylphosphonic acid and diphenylphosphinic acid. It is preferably an organic acid, more preferably a carboxylic acid and most preferably acetic acid.

In respect to a use proportion when using the above acids, use of 4 times mole or more based on the compound (3-1) makes it possible to complete the reaction. If the above use proportion falls in the above range, undesirable side reactions are less likely to be brought about, and an amount of a neutralizing agent used at an after-treating step is small, so that it is efficient. The above use proportion is preferably 4 times mole or more and 10 times mole or less, more preferably 4 times mole or more and 5 times mole or less based on the compound.

The reaction temperature may be room temperature, and heating may be carried out, if necessary, in order to accelerate the reaction. Or, cooling may be carried out, if necessary, in order to control heat generated by the reaction or undesirable reactions.

The reaction time is 0.5 to 8 hours. In general, however, the reaction time is influenced by, in addition to the reactivity of the raw material, the raw material concentration, the reaction temperature, the shape (stirring efficiency) of the apparatus and the form of the product or the by-products, and therefore the range of the above reaction time does not mean to restrict the present invention.

The compound (5) can be synthesized by reacting the compound (3-2) with the compound (4) making use of nucleophilic displacement as is the case with the compound (3-1). A preferred use amount of the compound (4) is 3 to 15 times in terms of an equivalent ratio based on the compound (3-2) when it is reacted with the whole Si—OH (silanol) groups of the compound (3-2). In this reaction, hydrogen of silanol is reacted with chlorine of chlorosilane to thereby generate hydrogen chloride, and therefore this hydrogen chloride has to be removed from the reaction system. A method for removing hydrogen chloride shall not be restricted, and triethylamine is most preferably used. A preferred use amount of triethylamine is 3 to 15 times in terms of an equivalent ratio based on the compound (3-2). A preferred solvent used in the reaction is the same as those in the reaction using the compound (3-1). The preferred reaction temperature is temperature at which side reactions do not take place at the same time and a quantitative nucleophilic reaction can be allowed to go on. In charging the raw materials, the reaction is most preferably carried out under a low temperature condition, for example, in an ice bath, and then it may be carried out at room temperature. The reaction time shall not specifically be restricted as long as it is time enough for allowing a quantitative nucleophilic reaction to go on. Usually, the intended silicon compound can be obtained in 1 to 15 hours.

In synthesizing the silicon compound of the present invention, a hydrosilylation reaction method using the compound (5) described above is preferably used. That is, it is the reaction of the compound (5) with a compound (6) in the presence of a transition metal catalyst:

$$CH_2=CH-Z^2-OH \qquad (6)$$

$Z^2$ in Formula (6) is a single bond or alkylene having a carbon atom number of 1 to 18 or alkenylene having a carbon atom number of 2 to 6, and optional —$CH_2$— in these alkylene and alkenylene may be substituted with —O—.

The examples of the transition metal catalyst used are platinum, rhodium, iridium, ruthenium, palladium, molybdenum, iron, cobalt, nickel and manganese. Among them, a platinum catalyst is more preferred. The above catalysts can be used in the form of a homogeneous catalyst in which they are dissolved in a solvent or a solid catalyst in which they are carried on carbon or silica. They may be used in a form in which phosphine, amine and potassium acetate are allowed to be coexistent. A preferred use amount of the transition metal catalyst is $1\times10^{-6}$ to $1\times10^{-2}$ mole per mole of an Si—H group in the compound (5) in terms of a transition metal catalyst atom.

A use amount of the compound (6) is preferably 1 to 5 times in terms of an equivalent ratio based on an Si—H group in the compound (5). Hydrosilylation reaction is reaction which almost quantitatively proceeds, and therefore it is not meaningful so much to increase the above equivalent ratio. However, the effect of shortening the reaction time can be expected, and therefore an adverse effect brought about by using the compound (6) in a large amount is only the cost efficiency. On the other hand, when intending to allow a part of the Si—H group to remain as it remains unreacted, it is enough to make the equivalent ratio described above lower than 1. Thus, a compound represented by Formula (7) is obtained:

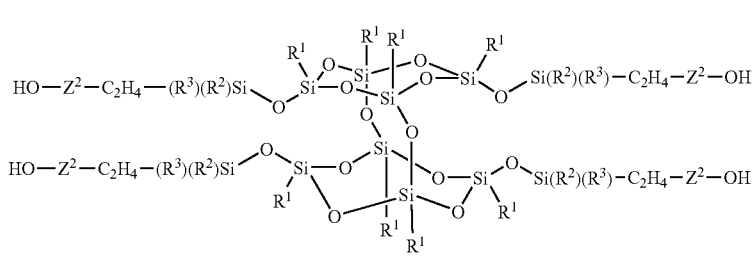
(7)

$R^1$, $R^2$ and $R^3$ in Formula (7) have the same meanings as those of the respective codes in Formula (1), and $Z^2$ has the same meaning as that of $Z^2$ in Formula (6).

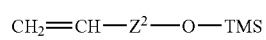
(6-T)

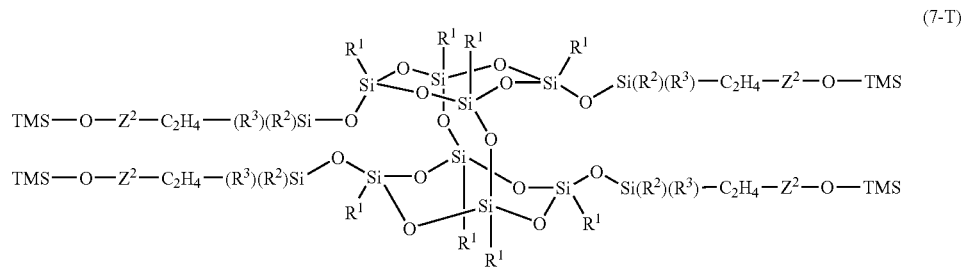
(7-T)

A preferred reaction temperature in the hydrosilylation reaction is not higher than a boiling point of the solvent used. The compound (6) is a compound having a polymerizable unsaturated bond. The preferred reaction temperature for preventing this compound from being spontaneously polymerized during the hydrosilylation reaction is 20 to 80° C. A polymerization inhibitor such as phenol derivatives, phenothiazine derivatives or N-nitrosophenylamine salt derivatives may be used for the purpose of inhibiting the above polymerization reaction. The most preferred polymerization inhibitor is 4-tert-butylpyrocatechol. A preferred use amount thereof is 1 to 100,000 ppm based the whole weight of the reaction liquid. The more preferred range of the use amount thereof is 100 to 20,000 ppm.

An organic solvent used for the above hydrosilylation reaction shall not specifically be restricted as long as it readily dissolves the raw materials without reacting with them.

The preferred examples of the organic solvent are aliphatic hydrocarbons (examples: hexane and heptane), aromatic hydrocarbons (examples: toluene and xylene) and cyclic ethers (examples: tetrahydrofuran and dioxane). Considering a solubility of the compound (5), toluene is most preferred. Alcohols such as 2-propanol may be added for the purpose of controlling the activity of the catalyst.

The compound (7) can be produced as well by the following method. First, the compound (5) and a compound (6-T) having an alkenyl group protected by a trimethylsilyl group are subjected to hydrosilylation reaction in toluene in the presence of a platinum-divinyltetramethylsiloxane complex to thereby produce a compound (7-T). Then, it is derived into the compound (7) having a hydroxyl group at room temperature or under a slightly heating (40° C.) condition by alcoholysis using large excess methanol.

$Z^2$ in the above formulas has the same meaning as that of $Z^2$ in Formula (6); $Z^2$, $R^1$, $R^2$ and $R^3$ have the same meanings as those of these codes in Formula (7); and TMS represents a trimethylsilyl group.

Then, the compound (7) is reacted with a compound (8) in which halogen is bonded to carbon of an a position, whereby the compound (1-1) is obtained:

(8)

$R^4$, $R^5$ and $X^1$ in Formula (8) have the same meanings as those of these codes in Formula (2-1), and X is halogen. The examples of this halogen are chlorine, bromine and iodine, and chlorine and bromine are preferred. $X^1$ may be the same as or different from X.

Hydrogen chloride by-produced in the above reaction induces side reactions such as dehydration and addition to a double bond part, and therefore the reaction is carried out in the coexistence of an organic base in order to remove it. The examples of the organic base are pyridine, dimethylaniline, triethylamine and tetramethylurea. Other organic bases may be used as long as they can inhibit the side reactions and allow the reaction to quickly proceed. The most preferred example of the organic base is triethylamine. This reaction is a nucleophilic displacement reaction which proceeds quantitatively, and a use amount of the compound (8) is preferably 1 to 10 times in terms of an equivalent ratio based on the compound (7). An increase in a use amount of the compound (8) makes it possible to react the whole compound (7) and makes it possible to shorten the reaction time.

Usually, the above reaction is carried out in the environment of inert gas such as argon gas and nitrogen gas in the presence of a dried organic solvent which is inert to the raw materials. The examples of the organic solvent are cyclic ethers (THF, dioxane and the like), aromatic hydrocarbons (toluene, xylene and the like), halogenated hydrocarbons (methylene chloride, chloroform and the like) and carbon tetrachloride. The preferred example of the organic solvent is methylene chloride. The reaction temperature shall not specifically be restricted. However, the above reaction quickly goes on while generating heat, and therefore usually it is carried out preferably under a low temperature condition. The preferred reaction temperature is 100° C. or lower, and the most preferred reaction temperature is 35° C. or lower. As a matter of fact, the reaction may be carried out while irregularly controlling the reaction temperature. For example, the reaction may be carried out while cooling the reaction system using a dry ice-methanol bath or an ice bath in an initial stage, and then the temperature may be elevated to the vicinity of room temperature to continue the reaction. The reaction time shall not specifically be restricted, and usually the intended silicon compound can be obtained in 1 to 10 hours.

The compound (1-1) can be produced as well by a method in which a reaction step of the compound (6) and the compound (8) is carried out in advance. First, the compound (6) is reacted with the compound (8) to synthesize a compound represented by Formula (2-1-2):

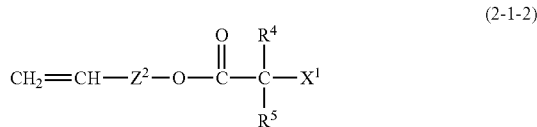

(2-1-2)

$Z^2$ in Formula (2-1-2) has the same meaning as that of Z in Formula (6), and $X^1$, $R^4$ and $R^5$ have the same meanings as those of these codes in Formula (2-1).

Then, the compound (2-1-2) and the compound (4) are subjected to hydrosilylation reaction to synthesize a compound represented by Formula (2-1-3), and it is further reacted with the compound (3-1) or the compound (3-2) to synthesize the compound (1-1). A method for synthesizing the compound (2-1-3) is described in, for example, Macromol. Rapid Commu., 23 (2002), 612-.

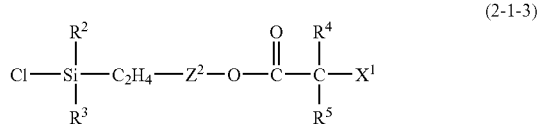

(2-1-3)

$Z^2$ in Formula (2-1-3) has the same meaning as that of $Z^2$ in Formula (6); $R^2$ and $R^3$ have the same meanings as those in Formula (1-1); and $X^1$, $R^4$ and $R^5$ have the same meanings as those of these codes in Formula (2-1).

The reaction of the compound (6) with the compound (8) can be carried out in the same manner as that of the reaction of the compound (7) with the compound (8). The hydrosilylation reaction of the compound (2-1-2) with the compound (4) can be carried out in the same manner as that of the reaction of the compound (6) with the compound (5). The reaction of the compound (2-1-3) with the compound (3-1) or the compound (3-2) can be carried out in the same manner as that of the reaction of the compound (4) with the compound (3-1) or the compound (3-2).

In the following explanations, a general term of "impurities" shall be given to the unreacted raw material compounds and the solvent. If a distillation method is applied in order to remove the impurities, the liquid is maintained under a high temperature condition for long time, and therefore the intended compound is likely to be decomposed. Accordingly, refining is preferably carried out by reprecipitation operation in order to efficiently remove the impurities without damaging a purity of the compound (1-1). This refining method is carried out in the following manner. First, the reaction liquid is dissolved in a solvent dissolving both of the compound (1-1) and the impurities. In this case, a preferred concentration of the compound (1-1) is, roughly speaking, 1 to 15% by weight. Next, a solvent which does not dissolve the compound (1-1) but dissolve the impurities, a so-called precipitant is added to the above solution to precipitate only the compound (1-1). A preferred use amount of the precipitant is 20 to 50 times based on the weight of the solvent used for dissolving both of the compound (1-1) and the impurities. The above use range is a rough standard, and as is the case with the foregoing concentration rage of the compound (1-1), it does not necessarily have to fall in the above range.

The preferred solvent used for dissolving the compound (1-1) is a solvent having a large dissolving power and a relatively low boiling point. The preferred precipitant is a solvent which is compatible with the solvent for dissolving the compound (1-1) and does not dissolve the compound (1-1) at all and which dissolves only the impurities and has a relatively low boiling point. The example of the preferred precipitant is lower alcohols. The particularly preferred precipitant is methanol. A repeating frequency of the reprecipitation operation is advisably raised in order to further elevate the refining degree.

A column chromatographic method is preferably applied in order to further refine the compound (1-1) after removing the polymerizable unreacted products. An adsorbent used in this case is silica gel and the like. A preferred developing solvent is hexane, cyclohexane, toluene, chloroform, ethyl acetate and acetone. More preferred developing solvent is a mixed solvent of hexane and ethyl acetate. A mixing proportion of the solvents shall not specifically be restricted, and it is controlled so that a migration rate (Rf value) of the intended compound to the developing solvent falls in a range of 0.1 to 0.7.

Next, a production process of the compound (1-2) out of the silicon compounds of the present invention shall be explained:

(1-2)

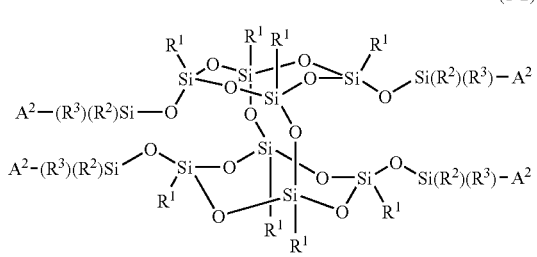

$R^1$, $R^2$ and $R^3$ in Formula (1-2) have the same meanings as those of these codes in Formula (1), and $A^2$ is a group represented by Formula (2-2):

(2-2)

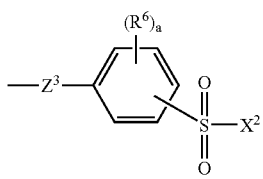

In Formula (2-2), $Z^3$ is alkylene having a carbon atom number of 2 to 10, and optional —CH$_2$— in this alkylene may be substituted 15 with —O— or —COO—; $R^6$ is alkyl having a carbon atom number of 1 to 3; a is an integer of 0 to 2; $X^2$ is halogen; and a bonding position of —SO$_2$X$^2$— on the benzene ring is an ortho position, a meta position or a para position to a bonding position of $Z^3$, and a bonding position of $R^6$ is an optional position excluding the respective bonding positions of $Z^3$ and —SO$_2$X$^2$—.

First, a compound represented by Formula (4) and a compound represented by Formula (2-2-2) are subjected to hydrosilylation reaction to synthesize a compound represented by Formula (2-2-3):

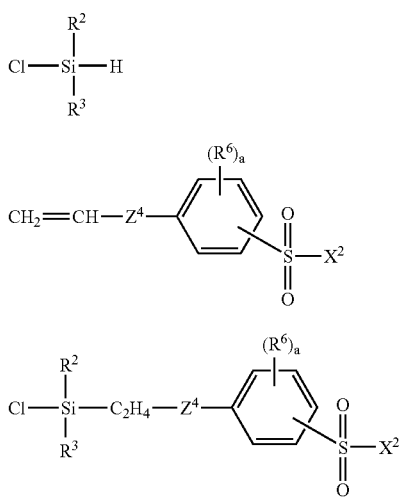

In the above formulas, $Z^4$ is a single bond or alkylene having a carbon atom number of 1 to 8, and optional —CH$_2$— in this alkylene may be substituted with —O— or —COO—; $R^6$, $X^2$ and a have the same meanings as those of these codes in Formula (2-2); a bonding position of —SO$_2$X$^2$— on the benzene ring is an ortho position, a meta position or a para position to a bonding position of halogenated $Z^4$, and a bonding position of $R^6$ is an optional position excluding the respective bonding positions of $Z^4$ and —SO$_2$X$^2$—; and $R^2$ and $R^3$ have the same meanings as those of these codes in Formula (1-2).

Then, the compound (2-2-3) is reacted with the compound (3-1) or the compound (3-2) each described above to synthesize the silicon compound represented by Formula (1-2).

The hydrosilylation reaction of the compound represented by Formula (4) with the compound represented by Formula (2-2-2) can be carried out in the same manner as that of the reaction of the compound (5) with the compound (6). The reaction of the compound (2-2-3) with the compound (3-1) or the compound (3-2) can be carried out in the same manner as that of the reaction of the compound (4) with the compound (3-1) or the compound (3-2).

The refining method by reprecipitation operation and/or the column chromatographic method each described above can be used for refining the compound (1-2) contained in the reaction mixture.

Next, the production processes of the compound (1-3) and the compound (1-4) out of the silicon compounds of the present invention shall be explained:

(1-3)

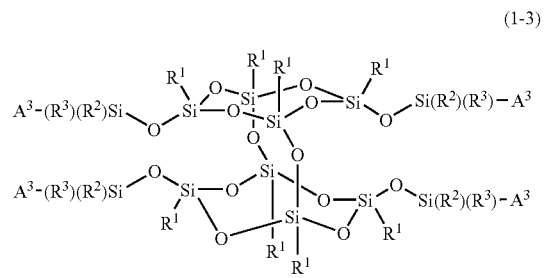

(1-4)

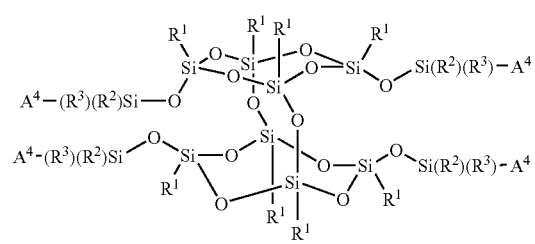

$R^1$, $R^2$ and $R^3$ in the above formulas have the same meanings as those of these codes in Formula (1); and $A^3$ is a group represented by Formula (2-3); and $A^4$ is a group represented by Formula (2-4):

(2-3)

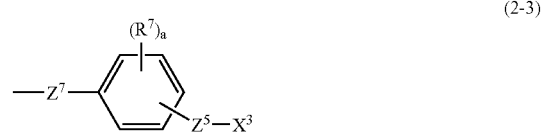

In Formula (2-3), $Z^5$ is alkylene which has a carbon atom number of 1 to 3 and in which optional —CH$_2$— may be substituted with —O—; $Z^7$ is alkylene which has a carbon atom number of 2 to 10 and in which optional —CH$_2$— may be substituted with —O—, —COO— or —OCO—; $R^7$ is alkyl having a carbon atom number of 1 to 3; a is an integer of 0 to 2; $X^3$ is halogen; and a bonding position of $Z^5$ on the benzene ring is a meta position or a para position to a bonding position of $Z^7$, and a bonding position of $R^7$ is an optional position excluding the respective bonding positions of $Z^5$ and $Z^7$;

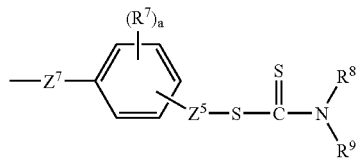

(2-4)

In Formula (2-4), $R^8$ and $R^9$ are independently alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $Z^5$ is alkylene which has a carbon atom number of 1 to 3 and in which optional —CH$_2$— may be substituted with —O—; $Z^7$ is alkylene which has a carbon atom number of 2 to 10 and in which optional —CH$_2$— may be substituted with —O—, —COO— or —OCO—; $R^7$ is alkyl having a carbon atom number of 1 to 3; a is an integer of 0 to 2; and a bonding position of $Z^5$ on the benzene ring is a meta position or a para position to a bonding position of $Z^7$, and a bonding position of $R^7$ is an optional position excluding the respective bonding positions of $Z^5$ and $Z^7$.

A preferred production process for the compound (1-3) is the hydrosilylation reaction of a compound represented by Formula (2-3-2) with the compound (5) obtained by the reaction of the compound (3-1) or the compound (3-2) with the compound (4):

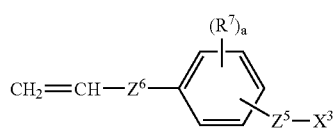

(2-3-2)

In Formula (2-3-2), $Z^6$ is a single bond or alkylene which has a carbon atom number of 1 to 8 and in which optional —CH$_2$— may be substituted with —O—, —COO— or —OCO—; $Z^5$, $R^7$, $X^3$ and a have the same meanings as those of these codes in Formula (2-3); and a bonding position of $Z^5$ on the benzene ring is a meta position or a para position to a bonding position of $Z^6$, and a bonding position of $R^7$ is an optional position excluding the respective bonding positions of $Z^5$ and $Z^6$.

The hydrosilylation reaction of the compound (5) with the compound (2-3-2) can be carried out in the same manner as that of the reaction of the compound (5) with the compound (6).

The refining method by reprecipitation operation and/or the column chromatographic method each described above can be used for refining the compound (1-3) contained in the reaction mixture.

The silicon compound represented by Formula (1-4) can be obtained by reacting the compound (1-3) obtained at the hydrosilylation reaction step described above with a dithiocarbamic acid metal salt represented by Formula (9):

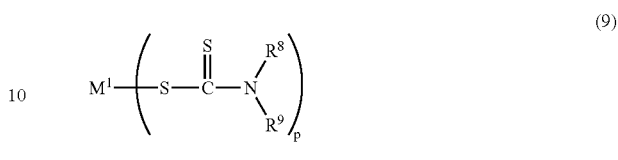

(9)

$R^8$ and $R^9$ in Formula (9) have the same meanings as those of these codes in Formula (2-4); $M^1$ is a metal element of the 1st or the 2nd group in the periodic table; and p is the same value as a valence of $M^1$. The examples of $M^1$ are Li, Na, K, Cu, Mg, Ca and Zn, and the preferred examples of $M^1$ are Na and K.

The reaction of the compound (1-3) with the compound (9) is a quantitative nucleophilic displacement reaction, and side reactions do not take place. However, a preferred use amount of dithiocarbamate is 1 to 5 times in terms of an equivalent ratio based on a halogen content in the compound (1-3). Use of a large amount of this salt makes it possible to shorten the reaction time. The reaction is usually carried out in an inert gas atmosphere such as nitrogen in a dried organic solvent which is inert to the raw materials. The examples of the organic solvent are lower alcohols (example: methanol), cyclic ethers (examples: tetrahydrofuran and dioxane) and aromatic hydrocarbons (examples: toluene and xylene). The preferred examples of the organic solvent are tetrahydrofuran and methanol. The preferred reaction temperature is 120° C. or lower considering the possibility that dithiocarbamate is thermally decomposed. The more preferred temperature is 100° C. or lower. The reaction time shall not specifically be restricted, and the intended silicon compound can be obtained usually in 1 to 10 hours. Capable of being used, if necessary, for the reaction is a phase transfer catalyst such as benzyltrimethylammonium chloride, tetramethylammonium chloride, tetrabutylammonium bromide, trioctylammonium chloride, dioctylmethylammonium chloride, triethylamine or dimethylaniline.

The compound (1-4) contained in the reaction mixture is refined by a refining method carried out by the reprecipitation operation and/or the column chromatographic method each described above. The reaction of dithiocarbamate with the compound (1-3) and refining of the compound (1-4) have to be carried out under a fluorescent lump in which a UV ray is cut and in a draft in which a UV-cut film is applied. The compound (1-4) has dithiocarbamate which is a photosensitive group, and therefore it has to be stored in a light-shielded vessel charged with inert gas such as nitrogen and argon in a cold and dark place under non-aqueous environment.

The compound (1-4) can be obtained as well by a process in which a reacting step of a dithiocarbamic acid metal salt with a halogenated alkyl group is carried out in advance. This production process is a process in which the compound (2-3-2) is first reacted with the compound (9) to prepare a compound represented by Formula (2-4-2):

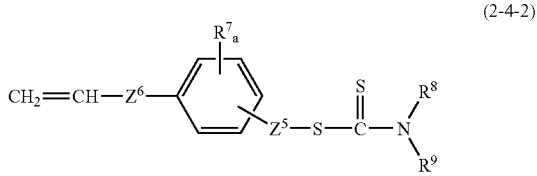

(2-4-2)

In Formula (2-4-2), $Z^6$ is a single bond or alkylene which has a carbon atom number of 1 to 8 and in which optional —$CH_2$— may be substituted with —O—, —COO— or —OCO—; the other codes have the same meanings as those of the codes in Formula (2-4); and a bonding position of $Z^5$ on the benzene ring is a meta position or a para position to a bonding position of $Z^6$, and a bonding position of $R^7$ is an optional position excluding the respective bonding positions of $Z^5$ and $Z^6$.

This reaction itself is fundamentally the same as the reaction of the compound (1-3) with the compound (9) each described above, and it can be carried out in the same manner as in the case of the above reaction. However, the same caution as in the reaction of the compound (5) with the compound (2-3-2) in the production process described above is required in terms of handling the compound having a polymerizable group. That is, the reaction temperature has to be controlled to a considerably low temperature of 20 to 80° C., and a polymerization inhibitor has to be used. Further, a UV ray has to be cut off as much as possible not only in the reaction and the refining step but also in storing the product. The compound (1-4) can be obtained by the hydrosilylation reaction of the compound (5) with the compound (2-4-2) each described above. This hydrosilylation reaction can be carried out in the same manner as that of the reaction of the compound (5) with the compound (2-3-2).

The compound (1-3) can be produced as well by a production process in which reaction using the compound (3-1) or the compound (3-2) is a final reaction step. First, the compound (4) and the compound (2-3-2) are subjected to hydrosilylation reaction to produce a compound represented by Formula (2-3-3):

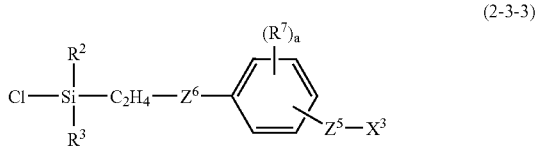

(2-3-3)

In Formula (2-3-3), $R^2$ and $R^3$ have the same meanings as those of these codes in Formula (4), and the other codes have the same meanings as those of these codes in Formula (2-3-2). The bonding positions of $Z^5$ and $R^7$ on the benzene ring are the same as the bond positions thereof in Formula (2-3-2).

Then, the compound (2-3-3) is reacted with the compound (3-1) or the compound (3-2) to produce the compound (1-3). The hydrosilylation reaction of the compound (4) with the compound (2-3-2) can be carried out in the same manner as that of the hydrosilylation reaction of the compound (5) with the compound (2-3-2). The reaction of the compound (2-3-3) with the compound (3-1) or the compound (3-2) can be carried out in the same manner as that of the reaction of the compound (4) with the compound (3-1) or the compound (3-2).

Next, an addition-polymerizable monomer which can initiate polymerization using the compound (1) shall be explained. This addition-polymerizable monomer is a monomer having at least one addition-polymerizable double bond. One of the examples of a monomer having one addition-polymerizable double bond is a (meth)acrylic acid derivative. The specific examples thereof are (meth)acrylic acid, methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, n-hexyl (meth)acrylate, cyclohexyl (meth)acrylate, n-heptyl (meth)acrylate, n-octyl (meth)acrylate, 2-ethylhexyl (meth)acrylate, nonyl (meth)acrylate, decyl (meth)acrylate, dodecyl (meth)acrylate, phenyl (meth)acrylate, toluyl (meth)acrylate, benzyl (meth)acrylate, 2-methoxyethyl (meth)acrylate, 3-methoxypropyl (meth)acrylate, 3-methoxybutyl (meth)acrylate, 2-hydroxyethyl (meth)acrylate, 2-hydroxypropyl (meth)acrylate, stearyl (meth)acrylate, glycidyl (meth)acrylate, 3-ethyl-3-(meth)acryloyloxymethyloxetane, 2-(meth)acryloyloxyethylisocyanate, 2-aminoethyl (meth)acrylate, 2-(2-bromopropanoyloxy)ethyl (meth)acrylate, 2-(2-bromoisobutyryloxy)ethyl (meth)acrylate, 1-(meth)acryloxy-2-phenyl-2-(2,2,6,6-tetramethyl-1-piperidinyloxy)ethane, (1-(4-((4-(meth)acryloxy)ethoxyethyl)phenylethoxy)piperidine, γ-(methacryloyloxypropyl)trimethoxysilane, 3-(3,5,7,9,11,13,15-heptaethylpentacyclo-[9.5.1.1$^{3,9}$.1$^{5,15}$.1$^{7,13}$]octasiloxane-1-yl)propyl (meth)acrylate, 3-(3,5,7,9,11,13,15-heptaisobutyl-pentacyclo[9.5.1.1$^{3,9}$.1$^{5,15}$.1$^{7,13}$]octasiloxane-1-yl)propyl (meth)acrylate, 3-(3,5,7,9,11,13,15-heptaisooctylpentacyclo[9.5.1.1$^{3,9}$.1$^{5,15}$.1$^{7,13}$]-octasiloxane-1-yl)propyl (meth)acrylate, 3-(3,5,7,9,11,13,15-heptacyclopentylpentacyclo[9.5.1.1$^{3,9}$.1$^{5,15}$.1$^{7,13}$]-octasiloxane-1-yl)propyl (meth)acrylate, 3-(3,5,7,9,11,13,15-heptaphenylpentacyclo[9.5.1.1$^{3,9}$.1$^{5,15}$.1$^{7,13}$]-octasiloxane-1-yl)propyl (meth)acrylate, 3-[(3,5,7,9,11,13,15-heptaethylpentacyclo-[9.5.1.1$^{3,9}$.1$^{5,15}$.1$^{7,13}$]octasiloxane-1-yloxy)dimethylsilyl]propyl (meth)acrylate, 3-[(3,5,7,9,11,13,15-heptaisobutylpentacyclo-[9.5.1.1$^{3,9}$.1$^{5,15}$.1$^{7,13}$]octasiloxane-1-yloxy)dimethylsilyl]propyl (meth)acrylate, 3-[(3,5,7,9,11,13,15-heptaisooctylpentacyclo-[9.5.1.1$^{3,9}$.1$^{5,15}$.1$^{7,13}$]octasiloxane-1-yloxy)dimethylsilyl]propyl (meth)acrylate, 3-[(3,5,7,9,11,13,15-heptacyclopentylpentacyclo-[9.5.1.1$^{3,9}$.1$^{5,15}$.1$^{7,13}$]octasiloxane-1-yloxy)dimethylsilyl]propyl (meth)acrylate, 3-[(3,5,7,9,11,13,15-heptaphenylpentacyclo-[9.5.1.1$^{3,9}$.1$^{5,15}$.1$^{7,13}$]octasiloxane-1-yloxy)dimethylsilyl]propyl (meth)acrylate, ethylene oxide adducts of (meth)acrylic acid, trifluoromethylmethyl (meth)acrylate, 2-trifluoromethylethyl (meth)acrylate, 2-perfluoroethylethyl (meth)acrylate, 2-perfluoroethyl-2-perfluorobutylethyl (meth)acrylate, 2-perfluoroethyl (meth)acrylate, trifluoromethyl (meth)acrylate, diperfluoromethylmethyl (meth)acrylate, 2-perfluoromethyl-2-perfluoroethylethyl (meth)acrylate, 2-perfluorohexylethyl (meth)acrylate, 2-perfluorodecylethyl (meth)acrylate, 2-perfluorohexadecylethyl (meth)acrylate and 2-(meth)acryloyloxyethylphosphorylcholine.

Another example of the monomer having one addition-polymerizable double bond is a styrene base monomer. The specific examples thereof are styrene, vinyltoluene, α-methylstyrene, p-chlorostyrene, p-chloromethylstyrene, m-chloromethylstyrene, o-aminostyrene, p-styrenechlorosulfonic acid, styrenesulfonic acid and salts thereof, vinylphenylmethyl dithiocarbamate, 2-(2-bromopropanonyloxy)styrene, 2-(2-bromo-isobutyryloxy)styrene, 1-(2-((4-vinylphenyl)methoxy)-1-phenylethoxy)-2,2,6,6-tetramethyl-piperidine, 1-(4-vinylphenyl)-3,5,7,9,11,13,15- heptaethylpentacyclo[9.5.1.1$^{3,9}$.1$^{5,15}$.1$^{7,13}$]-octasiloxane, 1-(4-vinylphenyl)-3,5,7,9,11,13,15-heptaisobutylpentacyclo[9.5.1.1$^{3,9}$.1$^{5,15}$.1$^{7,13}$]-octasiloxane, 1-(4-vinylphenyl)-3,5,7,9,11,13,15-heptaisooctylpentacyclo[9.5.1.1$^{3,9}$.1$^{5,15}$.1$^{7,13}$]-octasiloxane, 1-(4-vinylphenyl)-3,5,7,9,11,13,15-heptacyclopentylpentacyclo[9.5.1.1$^{3,9}$.1$^{5,15}$.1$^{7,13}$]-octasiloxane, 1-(4-vinylphenyl)-3,5,7,9,11,13,15-heptaphenylpentacyclo[9.5.1.1$^{3,9}$.1$^{5,15}$.1$^{7,13}$]-octasiloxane, 3-(3,5,7,9,11,13,15-heptaethylpentacyclo[9.5.1.1$^{3,9}$.1$^{5,15}$.1$^{7,13}$]octasiloxane-1-yl)ethylstyrene, 3-(3,5,7,9,11,13,15-heptaisobutylpentacyclo[9.5.1.1$^{3,9}$.1$^{5,15}$.1$^{7,13}$]-octasiloxane-1-yl)ethylstyrene, 3-(3,5,7,9,11,13,15-heptaisooctylpentacyclo[9.5.1.1$^{3,9}$.1$^{5,15}$.1$^{7,13}$]-octasiloxane-1-yl)ethylstyrene, 3-(3,5,7,9,11,13,15-heptacyclopentylpentacyclo[9.5.1.1$^{3,9}$.1$^{5,15}$.1$^{7,13}$]-octasiloxane-1-yl)ethylstyrene, 3-(3,5,7,9,11,13,15-heptaphenylpentacyclo[9.5.1.1$^{3,9}$.1$^{5,15}$.1$^{7,13}$]-octasiloxane-1-yl)ethylstyrene, 3-((3,5,7,9,11,13,15-heptaethylpentacyclo[9.5.1.1$^{3,9}$.1$^{5,15}$.1$^{7,13}$]octasiloxane-1-yloxy)dimethylsilyl]ethylstyrene, 3-((3,5,7,9,11,13,15-heptaisobutylpentacyclo-[9.5.1.1$^{3,9}$.1$^{5,15}$.1$^{7,13}$]octasiloxane-1-yloxy)dimethylsilyl)ethylstyrene, 3-((3,5,7,9,11,13,15-heptaisooctylpentacyclo-[9.5.1.1$^{3,9}$.1$^{5,15}$.1$^{7,13}$]octasiloxane-1-yloxy)dimethylsilyl)ethylstyrene, 3-((3,5,7,9,11,13,15-heptacyclopentylpentacyclo[9.5.1.1$^{3,9}$.1$^{5,15}$.1$^{7,13}$]-octasiloxane-1-yloxy)dimethylsilyl)ethylstyrene and 3-((3,5,7,9,11,13,15-heptaphenylpentacyclo-[9.5.1.1$^{3,9}$.1$^{5,15}$.1$^{7,13}$]octasiloxane-1-yloxy)dimethylsilyl]ethylstyrene.

The other examples of the monomer having one addition-polymerizable double bond are fluorine-containing vinyl monomers (perfluoroethylene, perfluoropropylene, vinylidene fluoride and the like), silicon-containing vinyl base monomers (vinyltrimethoxysilane, vinyltriethoxysilane and the like), maleic anhydride, maleic acid, monoalkyl esters and dialkyl esters of maleic acid, fumaric acid, monoalkyl esters and dialkyl esters of fumaric acid, maleimide base monomers (maleimide, methylmaleimide, ethylmaleimide, propylmaleimide, butylmaleimide, hexylmaleimide, octylmaleimide, dodecylmaleimide, stearylmaleimide, phenylmaleimide and cyclohexylmaleimide), monomers having a nitrile group (acrylonitrile, methacrylonitrile and the like), monomers having an amide group (acrylamide, methacrylamide and the like), vinyl ester base monomers (vinyl acetate, vinyl propionate, vinyl pivalate, vinyl benzoate, vinyl cinnamate and the like), olefins (ethylene, propylene and the like), conjugated diene base monomers (butadiene, isoprene and the like), halogenated vinyls (vinyl chloride and the like), halogenated vinylidenes (vinylidene chloride and the like), halogenated allyls (allyl chloride and the like), allyl alcohol, vinylpyrrolidone, vinylpyridine, N-vinylcarbazole, methyl vinyl ketone and vinylisocyanate. Further, given as well are macromonomers which have one polymerizable double bond in a molecule and in which a principal chain is a macromer of styrene, (meth)acrylic acid ester, diorganosiloxane or alkylene glycol.

The examples of a monomer having two addition-polymerizable double bonds are divinylbenzene and di(meth)acrylate base monomers. The examples of the di(meth)acrylate base monomers are 1,3-butanediol di(meth)acrylate, 1,4-butanediol di(meth)acrylate, 1,6-hexanediol di(meth)acrylate, polyethylene glycol di(meth)acrylate, diethylene glycol di(meth)acrylate, neopentyl glycol di(meth)acrylate, triethylene glycol di(meth)acrylate, tripropylene glycol di(meth)acrylate, hydroxypivalic acid ester neopentyl glycol di(meth)acrylate, trimethylolpropane di(meth)acrylate, bis[(meth)acryloyloxyethoxy]bisphenol A, bis[(meth)acryloyloxyethoxy]tetrabromobisphenol A, bis[(meth)acryloxypolyethoxy]bisphenol A, 1,3-bis(hydroxyethyl) 5,5-dimethylhydantoin, 3-methylpentanediol di(meth)acrylate, di(meth)acrylates of hydroxypivalic acid ester neopentyl glycol derivatives and bis[(meth)acryloyloxypropyl]tetramethyldisiloxane. Further, given as well are macromonomers which have two polymerizable double bonds in a molecule and in which a principal chain is a macromer of styrene, (meth)acrylic acid ester, diorganosiloxane or alkylene glycol.

The examples of a monomer having three or more addition-polymerizable double bonds are trimethylolpropane tri(meth)acrylate, pentaerythritol tri(meth)acrylate, pentaerythritol tetra(meth)acrylate, dipentaerythritol monohydroxypenta(meth)acrylate, tris(2-hydroxyethylisocyanate) tri(meth)acrylate, tris(diethylene glycol)trimelate tri(meth)acrylate, 3,7,14-tris[(((meth)acryloyloxypropyl)dimethylsiloxy)]1,3,5,7,9,11,14-heptaethyltricyclo-[7.3.3.1$^{5,11}$]heptasiloxane, 3,7,14-tris[(((meth)acryloyloxypropyl)dimethylsiloxy)]-1,3,5,7,9,11,14-heptaisobutyltricyclo[7.3.3.1$^{5,11}$]-heptasiloxane, 3,7,14-tris[(((meth)acryloyloxy-propyl)dimethylsiloxy)]-1,3,5,7,9,11,14-heptaisooctyltricyclo[7.3.3.1$^{5,11}$]heptasiloxane, 3,7,14-tris[(((meth)acryloyloxypropyl)dimethylsiloxy)]-1,3,5,7,9,11,14-heptacyclopentyl-tricyclo[7.3.3.1$^{5,11}$]heptasiloxane, 3,7,14-tris[(((meth)acryloyloxypropyl)dimethylsiloxy)]-1,3,5,7,9,11,14-heptaphenyltricyclo[7.3.3.1$^{5,11}$]-heptasiloxane, octakis(3-(meth)acryloyloxypropyldimethylsiloxy)octasilsesquioxane and octakis(3-(meth)acryloyloxypropyl)octasilsesquioxane. Further, given as well are macromonomers which have three or more polymerizable double bonds in a molecule and in which a principal chain is a macromer of styrene, (meth)acrylic acid ester, diorganosiloxane or alkylene glycol.

The monomers described above may be used alone or a plurality thereof may be copolymerized. When copolymerized, they may be random-copolymerized or block-copolymerized. The preferred monomers used in the present invention are the (meth)acrylic acid derivatives and the styrene derivatives. The more preferred monomers are the (meth)acrylic acid derivatives. The plural (meth)acrylic acid derivatives may be copolymerized, and the plural styrene derivatives may be copolymerized. At least one (meth)acrylic acid derivative may be copolymerized with at least one styrene derivative.

Next, a method for subjecting an addition-polymerizable monomer to atom transfer radical polymerization using the compound (1-1) or the compound (1-2) or the compound (1-3) as an initiator and using a transition metal complex as a catalyst shall be explained. An atom transfer radical polymerization method in the present invention is one of living radical polymerization methods. The examples of documents in which the living radical polymerization method is described are J. Am. Chem. Soc., 117 (1995), 5614—, Macromolecules, 28 (1995), 7901- and Science, 272 (1996), 866-.

The preferred examples of a transition metal complex used as a polymerizing catalyst are metal complexes in which a 7th, 8th, 9th, 10th or 11th group element in the periodic table is used as central metal. The more preferred catalysts are a complex of zero-valent copper, a complex of monovalent copper, a complex of divalent ruthenium, a complex of divalent iron and a complex of divalent nickel. Among them, the complexes of copper are preferred. The examples of a monovalent copper compound are cuprous chloride, cuprous bromide, cuprous iodide, cuprous cyanide, cuprous oxide and cuprous perchlorate. When using the copper compounds, 2,2'-bipyridyl or derivatives thereof, 1,10-phenanthroline or derivatives thereof, pyridylmethaneimines (N-(n-propyl)-2-pyridylmethaneimine and the like), polyamines (tetramethylethylenediamine, pentamethyldiethylene-triamine, hexamethyltris(2-aminoethyl)amine and the like) or polycyclic alkaloid such as L-(–)-sparteine are added as a ligand in order to enhance the catalyst activity. A tristriphenylphosphine complex (RuCl$_2$ (PPh$_3$)$_3$) of divalent ruthenium chloride is also suited as the catalyst. When the ruthenium compound is used as the catalyst, aluminum alkoxides are added as an activating agent. The examples of the suited catalysts other than the above compounds are a bistriphenylphosphine complex (FeCl$_2$ (PPh$_3$)$_2$) of divalent iron, a bistriphenylphosphine complex (NiCl$_2$ (PPh$_3$)$_2$) of divalent nickel and a bistributylphosphine complex (NiBr$_2$ (PBu$_3$)$_2$) of divalent nickel.

A solvent may be used for the polymerization reaction. The examples of the solvent used are hydrocarbons (examples: benzene, toluene and the like), ethers (examples: diethyl ether, THF, diphenyl ether, anisole, dimethoxybenzene and the like), halogenated hydrocarbons (examples: methylene chloride, chloroform, chlorobenzene and the like), ketones (examples: acetone, methyl ethyl ketone, methyl isobutyl ketone and the like), alcohols (examples: methanol, ethanol, propanol, isopropanol, n-butyl alcohol, tert-butyl alcohol and the like), nitriles (examples: acetonitrile, propionitrile, benzonitrile and the like), esters (examples: ethyl acetate, butyl acetate and the like), carbonate base solvents (examples: ethylene carbonate, propylene carbonate and the like), amide base solvents (examples: N,N-dimethylformamide, N,N-dimethylacetamide and the like), hydrochlorofluorocarbon base solvents (examples: HCFC-141b, HCFC-225 and the like), hydrofluorocarbon base solvents (examples: HFCs and the like), perfluorocarbon base solvents (examples: perfluoropentane, perfluorohexane and the like), alicyclic hydrofluorocarbon base solvents (examples: fluorocyclopentane, fluorocyclobutane and the like), oxygen-containing fluorine base solvents (examples: fluoroether, fluoropolyether, fluoroketone, fluoroalcohol and the like) and water. The compounds given above in parentheses are the preferred examples of the respective solvents. They may be used alone or in combination of two or more kinds thereof. The polymerization can be carried out as well in an emulsion system or a system in which a supercritical fluid CO$_2$ is used as a medium. The solvent which can be used shall not be restricted to the above examples.

The atom transfer radical polymerization can be carried out under reduced pressure, atmospheric pressure or applied pressure according to the kind of the addition-polymerizable monomer and the kind of the solvent. The polymerizing catalyst or a radical produced is likely to be deactivated when brought into contact with oxygen. In such case, the polymerizing speed is reduced, and the good living polymer is not obtained. Accordingly, it is important to carry out the polymerization under inert gas environment of nitrogen or argon. In this reaction, oxygen dissolved in the polymerization system has to be removed in advance under reduced pressure. Then, it is possible to shift to a polymerization step as it is under reduced pressure after finishing the step of removing dissolved oxygen. A conventional method can be adopted for the atom transfer radical polymerization, and it shall not specifically be restricted by the polymerization method. Capable of being adopted is, for example, a bulk polymerization method, a solution polymerization method, a suspension polymerization method, an emulsion polymerization method or a bulk-suspension polymerization method.

The polymerization temperature falls in a range of 0 to 200° C., and the preferred polymerization temperature falls in a range of room temperature to 150° C.

When using a compound (1-1-2) as an initiator, a polymer obtained by the method described above is represented by Formula (P-1). In the following explanations, the polymer represented by Formula (P-1) is shown as the polymer (P-1):

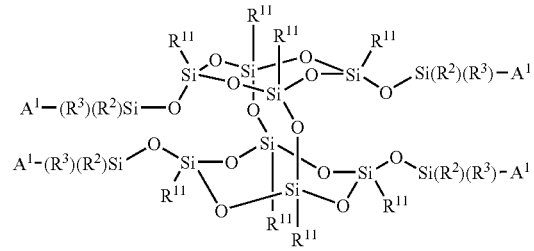

(1-1-2)

In Formula (1-1-2), all R$^{11}$'s are the same group selected from alkyl having a carbon atom number of 1 to 8 in which optional hydrogen may be substituted with fluorine and in which optional —CH$_2$— may be substituted with —O—, —CH═CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —CH$_2$— may be substituted with —O—; when the phenyl or a phenyl group in the phenylalkyl has plural substituents, the substituents may be the same group or different groups; R$^2$ and R$^3$ are groups independently selected from alkyl having a carbon atom number of 1 to 8, phenyl and cyclohexyl; and A$^1$ is a group represented by Formula (2-1):

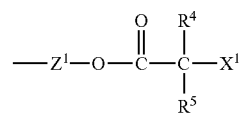

(2-1)

In Formula (2-1), Z$^1$ is alkylene having a carbon atom number of 2 to 20 or alkenylene having a carbon atom number of 3 to 8, and optional —CH$_2$— in these alkylene and alkenylene may be substituted with —O—; R$^4$ is hydrogen, alkyl having a carbon atom number of 1 to 20, aryl having a carbon atom number of 6 to 20 or arylalkyl having a carbon atom number of 7 to 20; R$^5$ is alkyl having a carbon atom number of 1 to 20, aryl having a carbon atom number of 6 to 20 or arylalkyl having a carbon atom number of 7 to 20; and X$^1$ is halogen.

In introducing A$^1$ as a polymerization initiator into a silsesquioxane derivative, a representative method for obtaining the derivative which is not hydrolyzed includes a method in which a Grignard reagent is reacted with Si-halogen and a method in which a compound having an aliphatic unsaturated bond is reacted with Si—H. Usually, the latter is called a hydrosilylation reaction method. In the present invention, the hydrosilylation reaction method is rather liable to be applied in terms of an easiness in obtaining the raw material, but it shall not be restricted thereto.

(P-1)

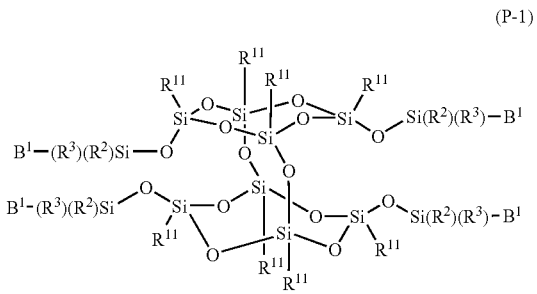

$R^{11}$, $R^2$ and $R^3$ in Formula (P-1) have the same meanings as those of these codes in Formula (1-1-2), and $B^1$ is a group represented by Formula (2-1-P):

(2-1-P)

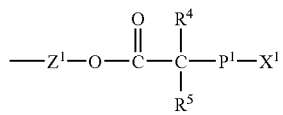

In Formula (2-1-P), $P^1$ is a chain of a structural unit obtained by polymerizing an addition-polymerizable monomer, and the other codes have the same meaning as those of the codes in Formula (2-1).

When using a compound (1-2-2) as an initiator, a polymer obtained by the method described above is represented by Formula (P-2). In the following explanations, the polymer represented by Formula (P-2) is shown as the polymer (P-2):

(1-2-2)

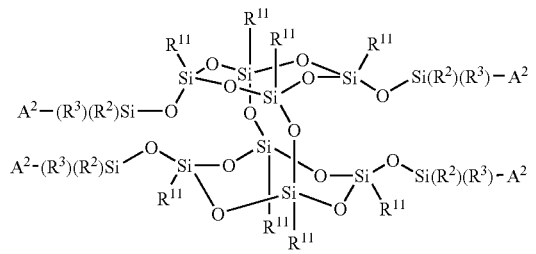

$R^{11}$, $R^2$ and $R^3$ in Formula (1-2-2) have the same meanings as those of these codes in Formula (1-1-2); $A^2$ is a group represented by Formula (2-2); and $B^2$ is a group represented by Formula (2-2-P):

(2-2)

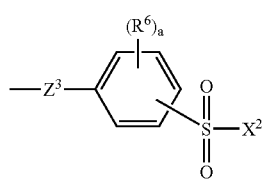

In Formula (2-2), $Z^3$ is alkylene having a carbon atom number of 2 to 10, and optional —$CH_2$— in this alkylene may be substituted with —O— or —COO—; $R^6$ is alkyl having a carbon atom number of 1 to 3; a is an integer of 0 to 2; $X^2$ is halogen; and a bonding position of —$SO_2X^2$ on the benzene ring is an ortho position, a meta position or a para position to a bonding position of $Z^3$, and a bonding position of $R^6$ is an optional position excluding the respective bonding positions of $Z^3$ and —$SO_2X^2$. Also when introducing $A^2$ as a polymerization initiator into a silsesquioxane derivative, a method in which a Grignard reagent is reacted with Si-halogen and a method in which a compound having an aliphatic unsaturated bond is reacted with Si—H can be used similarly to the case of obtaining the compound (1-1-2).

(P-2)

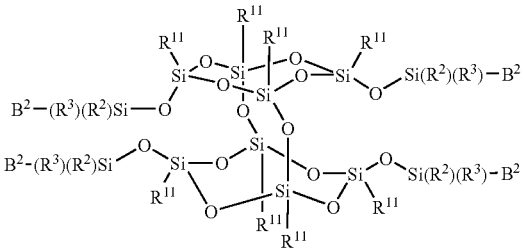

$R^{11}$, $R^2$ and $R^3$ in Formula (P-2) have the same meanings as those of these codes in Formula (1-2-2), and $B^2$ is a group represented by Formula (2-2-P):

(2-2-P)

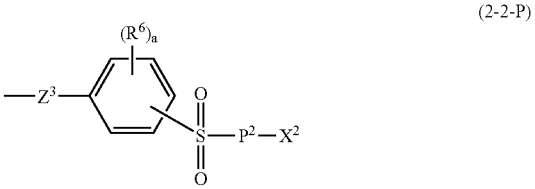

In Formula (2-2-P), $P^2$ is a chain of a structural unit obtained by polymerizing an addition-polymerizable monomer; the other codes have the same meanings as those of the codes in Formula (2-2); and the bonding positions of —$SO_2X^2$ and $R^6$ on the benzene ring are the same as the bonding positions in Formula (2-2).

When using a compound (1-3-2) as an initiator, a polymer obtained by the method described above is represented by Formula (P-3). In the following explanations, the polymer represented by Formula (P-3) is shown as the polymer (P-3):

(1-3-2)

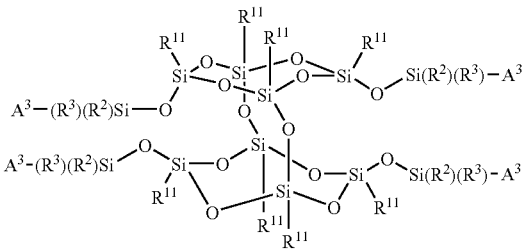

$R^{11}$, $R^2$ and $R^3$ in Formula (1-3-2) have the same meanings as those of these codes in Formula (1-1-2); $A^3$ is a group represented by Formula (2-3):

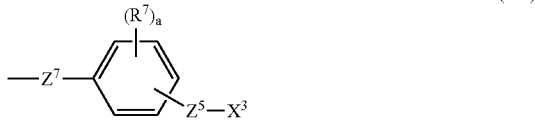

(2-3)

In Formula (2-3), $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; $X^3$ is halogen; and a bonding position of $Z^5$ on the benzene ring is a meta position or a para position to a bonding position of $Z^7$, and a bonding position of $R^7$ is an optional position excluding the respective bonding positions of $Z^5$ and $Z^7$. Also when introducing $A^3$ as a polymerization initiator into a silsesquioxane derivative, a method in which a Grignard reagent is reacted with Si-halogen and a method in which a compound having an aliphatic unsaturated bond is reacted with Si—H can be used similarly to the case of obtaining the compound (1-1-2).

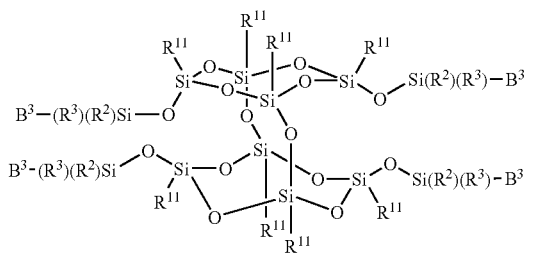

(P-3)

$R^{11}$, $R^2$ and $R^3$ in Formula (P-3) have the same meanings as those of these codes in Formula (1-3-2), and $B^3$ is a group represented by Formula (2-3-P):

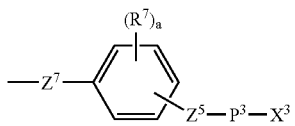

(2-3-P)

In Formula (2-3-P), $P^3$ is a chain of a structural unit obtained by polymerizing an addition-polymerizable monomer; the other codes have the same meaning as those of these codes in Formula (2-3); and the bonding positions of $Z^5$ and $R^7$ on the benzene ring are the same as the respective bonding positions in Formula (2-3).

Suitable selection of the kind of the monomer used makes it possible to control the structure of the polymer (P-1). For example, if the monomer is homopolymerized, silsesquioxane to which the homopolymer is bonded is obtained. If the plural monomers are added at the same time and polymerized, silsesquioxane to which the random copolymer is bonded is obtained. If adopted is a method in which the monomers are successively added, for example, a method in which the second monomer is added after finishing the polymerization of the first monomer to complete the polymerization, silsesquioxane to which the block copolymer is bonded is obtained. Repeating of the above staged polymerization using plural monomers makes it possible to obtain silsesquioxane to which the multiblock copolymer is bonded. Coexistence of, if necessary, a multifunctional monomer makes it possible as well to prepare a cross-linked polymer having a three-dimensional network structure.

When polymerizing a conventional addition-polymerizable monomer, combined use of a compound having a polymerizable functional group together with a function of an initiator makes it possible to obtain silsesquioxane to which the high branched type polymer is bonded. The examples of such compound are 2-(2-bromopropanoyloxy) ethyl (meth)acrylate, 2-(2-bromoisobutyryloxy)ethyl (meth) acrylate, 2-(2-bromopropanoyloxy)styrene and 2-(2-bromoisobutyryloxy)styrene. Combined use of a silicon compound having a (meth)acryl group or a styryl group makes it possible to introduce a structural unit containing a silicon atom into the structure of the polymer. The examples of the above silicon compound are trialkoxysilane, polydimethylsiloxane and silsesquioxane. After copolymerized with an addition-polymerizable monomer having an initiating group which does not take part in atom transfer radical polymerization, the addition-polymerizable monomer is further polymerized in the other polymerization mode (for example, nitroxyl polymerization and photo initiator-transfer agent-terminator polymerization) using the resulting polymer as an initiator, whereby a graft copolymer can be formed. The examples of the addition-polymerizable monomer having an initiating group which does not take part in atom transfer radical polymerization are 1-(2-(4-vinylphenylmethoxy)-1-phenylethoxy-2,2,6,6-tetramethylpyridine, 1-(meth)acryloxy-2-phenyl-2-(2,2,6,6-tetramethyl-1-piperidinyloxy)ethane, (1-(4-(4-(meth)acryloxyethoxyethyl) phenylethoxy)piperidine and vinylphenylmethyldithiocarbamate.

After copolymerized with a monomer having a glycidyl group (example: glycidyl (meth)acrylate), a monomer having an oxetanyl group(example: 3-ethyl-3-(meth)acryloyloxymethyloxetane) or a monomer having dioxolane(example: 4-(meth)acryloyloxymethyl-2-methyl-2-ethyl-1,3-dioxolane), an aliphatic sulfonium salt, an aromatic sulfonium salt or an aromatic iodonium salt is added as a thermally latent or optically latent cationic polymerization initiator to the resulting polymer, whereby a cross-linked polymer having a three-dimensional network structure can be prepared by cationic polymerization. The examples of the aliphatic sulfonium salt which is the thermally latent cationic polymerization initiator are 3-methyl-2-butenyltetramethylenesulfonium hexafluoroantimonate and 2-butenyltetramethylenesulfonium hexafluoroantimonate, and they are marketed from Asahi Denka Co., Ltd. Many products of the aromatic sulfonium salt which is the thermally latent or optically latent cationic polymerization initiator are marketed from Sanshin Chemical Industry Co., Ltd. and Asahi Denka Co., Ltd. Diphenyl-4-thiophenoxyphenylsulfonium hexafluoroantimonate also is the example of the aromatic sulfonium salt. The example of the aromatic iodonium salt is (4-pentadecyloxyphenyl)phenyliodonium hexafluoroantimonate. When carrying out optically latent cationic polymerization, a photosensitizer, for example, Adeka Optomer SP-100 (manufactured by Asahi Denka Co., Ltd.) may be used in combination. Also, when obtaining a cross-linked polymer having a three-dimensional network structure by cationic polymerization, a monofunctional or multifunctional glycidyl base cross-linking agent or a monofunctional or multifunctional oxetane base cross-linking agent may be allowed to coexist.

Next, a refining method for the polymer (P-1) shall be explained. This compound is isolated and refined by efficiently removing the unreacted vinyl base monomer. Various methods are available, and a refining method carried out by reprecipitation operation is preferred. This refining method is carried out in the following manner. First, a solvent which does not dissolve the polymer (P-1) but dissolves the unreacted monomer, a so-called precipitant is added to the polymerization reaction liquid containing the polymer (P-1) and the unreacted monomer to precipitate only the polymer (P-1). A preferred use amount of the precipitant is 20 to 50 times based on the weight of the polymerization reaction liquid described above.

The preferred precipitant is a solvent which is compatible with the polymerization solvent used in polymerization and which does not dissolve the polymer (P-1) at all but dissolves only the unreacted monomer and has a relatively low boiling point. The examples of the preferred precipitant are lower alcohols and aliphatic hydrocarbons. The particularly preferred precipitant is methanol and hexane. A repeating frequency of the reprecipitation operation is advisably increased in order to further raise a removing efficiency of the unreacted monomer. This method makes it possible to deposit only the polymer (P-1) in a poor solvent, and the polymer can readily be separated from the unreacted monomer by filtering operation.

The transition metal complex which is the polymerizing catalyst remains in the compound (P-1) isolated by the method described above, and therefore problems such as coloring of the polymer, influence on the physical properties and environmental safety are brought about in a certain case. Accordingly, this catalyst residue has to be removed in finishing the polymerization reaction. The catalyst residue can be removed by adsorbing treatment using activated carbon. The examples of adsorbents other than activated carbon are ion exchange resins (acid, basic or chelate form) and inorganic adsorbents. The inorganic adsorbents have a character of a solid acid, a solid base or neutrality. They are particles having a porous structure and therefore have a very high adsorbing ability. It is also one of the characteristics of the inorganic adsorbents that they can be used in a wide temperature range extending from a low temperature to a high temperature.

The examples of the inorganic adsorbents are silicon dioxide, magnesium oxide, silica alumina, aluminum silicate, activated alumina, clay base adsorbents such as acid clay and activated clay, zeolite base adsorbents, dawsonites compounds and hydrotalcites compounds. Zeolite includes natural products and synthetic products, and either can be used. Kinds such as a crystal form, an amorphous form, a noncrystal form, a glass form, a synthetic product and a natural product are available for silicon dioxide, and silicon dioxide of a powder form can be used in the present invention regardless of the kind. The examples of natural aluminum silicate are pumice, fly ash, kaoline, bentonite, activated clay and diatomaceous earth. Synthetic aluminum silicate has a large specific surface area and a high adsorbing ability. The hydrotalcites compound is carbonate hydrate of aluminum-magnesium hydroxide.

The acid adsorbents and the basic adsorbents are preferably used in combination with activated carbon. The examples of the acid adsorbents are acid clay, activated clay and aluminum silicate. The examples of the basic adsorbents are activated alumina, the zeolite base adsorbents and the hydrotalcites compounds each described above. These adsorbents may be used alone or in a mixture of two or more kinds thereof. The polymer (P-1) produced by the atom transfer radical polymerization can be refined by bringing into contact with activated alumina. A commercial product available from Aldrich Co., Ltd. can be used as activated alumina. When adsorbing treatment is carried out by using activated alumina in combination with the other adsorbent, the adsorbents can be mixed and brought into contact with the compound, but they may be brought into contact at the separate steps respectively. When brought into contact with the adsorbent, the reaction liquid may be used as it is or may be diluted with a solvent. The diluent may be selected from usual solvents only on the condition that it is not a poor solvent for the polymer. A temperature for treating with the adsorbent shall not specifically be restricted. The treatment may be carried out usually at 0 to 200° C. The preferred temperature range is room temperature to 180° C. A use amount of the absorbent falls in a range of 0.1 to 500% by weight based on the weight of the polymer (P-1). Considering the economical efficiency and the operability, the preferred range is 0.5 to 10% by weight.

A method of a batch system in which stirring-mixing and solid-liquid separation are carried out by batch operation can be used for solid-liquid contact of the absorbent and the polymer liquid. In addition thereto, capable of being used is a method of a continuous system such as a fixed layer system in which the polymer liquid is allowed to pass through a vessel charged with the adsorbent, a moving layer system in which the liquid is allowed to pass through a moving layer of the adsorbent and a fluidized layer system in which the adsorbent is fluidized by a liquid to carry out adsorption. Further, a mixing and dispersing operation carried out by stirring can be combined, if necessary, with operation for elevating the dispersing efficiency, such as shaking of the vessel and use of a supersonic wave. After the polymer liquid is brought into contact with the absorbent, the absorbent is removed by a method such as filtering, centrifugal separation and settling separation, and washing treatment is carried out if necessary to obtain the refined polymer liquid. Treatment by the absorbent may be carried out for the polymer (P-1) which is the final product, and it may be carried out for an intermediate product used for producing this polymer. For example, in the respective polymerizing steps of the block copolymer obtained by the atom transfer radical polymerization, this polymer can be isolated and subjected to adsorbing treatment. The polymer (P-1) subjected to treatment by the adsorbent may be separated by depositing in a poor solvent or distilling off volatile components such as the solvent under reduced pressure.

The catalyst residue can be removed by carrying out refining treatment using a non-water soluble solvent and a complexing agent aqueous solution or using a non-water soluble solvent and a complexing agent aqueous solution further containing an electrolytic component. That is, after the polymer (P-1) is dissolved in a non-water soluble solvent, a complexing agent aqueous solution or a complexing agent aqueous solution further containing an electrolytic component is added to the above solution of the polymer (P-1) and stirred and mixed to convert the transition metal component to a complex with the complexing agent, followed by extracting it in the aqueous layer, whereby a concentration of the catalyst component remaining in the polymer (P-1) can notably be reduced.

The polymerization reaction liquid may be a target for the refining treatment. When the polymerization reaction liquid has a high viscosity, a non-water soluble solvent may be added thereto to control the viscosity to a suited solution viscosity, and then the refining treatment may be carried out. That is, after the polymerization reaction liquid containing the polymer (P-1) is diluted by a prescribed amount of a non-water soluble solvent in finishing the polymerization reaction, a complexing agent aqueous solution or a complexing agent aqueous solution further containing an electrolytic component is added to the above solution and stirred and mixed to convert the transition metal component to a complex salt, which is transferred into the aqueous solution described above, and then the non-water soluble solvent containing the polymer (P-1) is separated from the aqueous solution described above by physical operation such as centrifugal separation and static separation. Such refining treatment makes it possible to notably reduce a concentration of the catalyst component remaining in the polymer (P-1).

The operational procedure of the above refining treatment may not necessarily be carried out in the manner described above. For example, a complexing agent or a complexing and an electrolytic component may be added to the polymer (P-1) or the polymerization reaction liquid containing the polymer (P-1), and then a non-water soluble solvent may be added thereto, followed by further adding water. The refining treatment, even if it is carried out by any operational procedure, leads finally to the same extraction treatment as the case of the operational procedure explained at the beginning, and the same effect is obtained.

In this case, a solution obtained by dissolving the polymer (P-1) in a non-water soluble solvent, the polymerization reaction liquid or a solution obtained by diluting the polymerization reaction liquid by a non-water soluble solvent shall be called a polymer (P-1) solution. The polymer (P-1) solution is preferably mixed and brought into contact with the complexing agent aqueous solution or the complexing agent aqueous solution further containing an electrolytic component by stirring in a bath type treating bath of a batch type equipped with a stirrer. A bath type treating bath of a shaking type may be used. A concentration of the polymer contained in the polymer (P-1) solution makes it a condition that the solution is homogeneous and that it has a viscosity which enables stirring and mixing with the complexing agent aqueous solution, and it is preferably 40% by weight or less. When a concentration of the polymer contained in the polymer (P-1) solution is raised, the problems of the deposition of the polymer and an increase in the viscosity are brought about in a certain case, and in such case, it is advisable to carry out treatment under heating in a treating bath equipped with a heating device such as a steam coil or a steam jacket by which heating can be carried out at 70 to 100° C. If the polymer contained in the polymer (P-1) solution has a low concentration and the solution is homogeneous at room temperature, the solution can be stirred and contacted at room temperature.

Centrifugal separation or static separation in which a difference in a specific gravity is utilized and electrostatic deoiling making use of a difference in electric properties can be utilized for oil-water separation of the polymer (P-1) solution from the complexing agent aqueous solution or the complexing agent aqueous solution further containing an electrolytic component. In the present invention, oil-water separation of two phases is required, and therefore a decanter of a two phase separation type is most suitably used, but it is a matter of course in this case that other centrifugal separators can be used. When an inorganic adsorbent is used in combination, a decanter of a three phase separation type is used since solid matters such as sludge are contained, but also in such case, other centrifugal separators can naturally be used. The polymer treated at the steps described above can be isolated by depositing in a poor solvent and distilling off volatile components such as the solvent and the like under reduced pressure.

The frequency of mixing and contacting of the polymer (P-1) solution with the complexing agent aqueous solution or the complexing agent aqueous solution further containing an electrolytic component and the oil-water separation step shall not specifically be restricted as long as a concentration of the catalyst component remaining in the polymer (P-1) can notably be reduced. That is, assuming that a mixing/contacting and oil-water separation step is one step, the transition metal component contained in the polymer (P-1) is analyzed every one step, whereby the frequency of the steps is determined at the step at which-the transition metal component has been reduced to the targeted content.

In general, an addition proportion of the complexing agent to the transition metal component contained in the polymer (P-1) is preferably 1 to 1000 equivalents in terms of a mole ratio of the complexing agent based on the transition metal component. A content of the transition metal contained in the polymer (P-1) can be forecasted in advance by calculation in charging the polymerization reaction liquid, and therefore an amount of the complexing agent described above can be determined by a content of the transition metal contained in the polymer (P-1) to be treated. A concentration of the complexing agent contained in the complexing agent aqueous solution falls preferably in a range of 0.001 to 20% by weight.

Further, in the complexing agent aqueous solution containing an electrolytic component, a use amount thereof shall not specifically be restricted as long as a rise in the oil-water separation efficiency by increasing a specific gravity of the aqueous solution is a principal object and time required for the separation is shortened. In general, it can be used in a saturated or half-saturated state.

Such step is carried out for the polymer (P-1) which is the final product, but it may be carried out for an intermediate product used for producing the above polymer. It is possible as well, for example, to isolate the above polymer in the respective polymerization stages of the block copolymer obtained by the atom transfer radical polymerization and then carry out the above treatment.

The examples of the non-water soluble solvent used at the above refining step are anisole, benzene, carbon tetrachloride, chlorobenzene, chloroform, 1-chloronaphthalene, dibenzylnaphthalene, o-dichlorobenzene, m-dichlorobenzene, 1,1-dichloroethane, 1,2-dichloroethane, dichloromethane, diisopropyl ether, N,N-dimethylaniline, diphenyl ether, ethyl acetate, mesitylene, methyl acetate, isoamyl acetate, cyclohexanone, cyclopentanone, nitrobenzene, nitromethane, tetrachloroethylene, tetralin, toluene, trichloroethylene and xylene. More preferred examples are chloroform, ethyl acetate and toluene.

The complexing agent aqueous solution used is an aqueous solution of at least one compound selected from aliphatic carboxylic acids, aromatic carboxylic acids, ammonia, amines, aminocarboxylic acids, amino acids, phosphoric acids, phosphonic acids and inorganic sulfur compounds. The compounds other than the inorganic sulfur compounds among the above compounds can be used, if necessary, in the form of salts, for example, the salts of alkaline metals such as sodium, potassium and lithium, the salts of alkaline earth metals such as calcium and barium, the salts of heavy metals such as iron (III) and vanadium, hydrochlorides, ammonium salts, amine salts, salts partially neutralized by equivalent or more or less of metals and basic substances based on carboxyl groups and the mixtures of the above salts.

The examples of the aliphatic carboxylic acids are formic acid, acetic acid, propionic acid, butyric acid, isobutyric acid, valeric acid, isovaleric acid, oxalic acid, malonic acid, succinic acid, glutaric acid, maleic acid, adipic acid, fumaric acid, citraconic acid, itaconic acid, tricarbazylic acid, propane-1,1,2,3-tetracarboxylic acid, butane-1-glycolic acid, lactic acid, β-hydroxypropionic acid, malic acid, tartaric acid, citric acid, alloisocitric acid, gluconic acid, pyruvic acid, oxaric acid, diglycolic acid and thiodiglycolic acid. The examples of the aromatic carboxylic acid are benzoic acid, phthalic acid, isophthalic acid, mandelic acid, salicylic acid, 5-sulfosalicylic acid, α-carboxy-o-anisic acid and o-(carboxymethylthio)benzoic acid.

The examples of the amines are diethylamine, methylamine, ethylamine, propylamine, triethylamine, morpholine, piperidine, ethylenediamine, N-methylethylenediamine, N-ethylethylenediamine, N-n-propylethylenediamine, N-isopropylethylenediamine, N-(2-hydroxyethyl)ethylenediamine, N,N-dimethylethylenediamine, N,N-diethylethylenediamine, N-N'dimethylethylenediamine, N,N'-diethylethylenediamine, N,N'-di-n-propylethylenediamine, N,N-di(2-hydroxyethyl)ethylenediamine, N,N,N',N'-tetramethylethylenediamine, 1,2-diaminopropane, meso-2,3-diaminobutane, rac-2,3-diaminobutane, trimethylenediamine, tetramethylenediamine, pentamethylenediamine, triethylenediamine, diethylenetriamine, 3,3'-diaminodipropylamine, triethylenetetraamine, 2-hydroxyethylamine, 2-methoxyethylamine, 2,2'-dihydroxydiethyleneamine and polyamideamine.

The examples of the aminocarboxylic acids are iminodiacetic acid, iminodipropionic acid, N-methyliminodiacetic acid, N-(3,3'-dimethylbutyl)iminodiacetic acid, phenyliminodiacetic acid, hydroxyethyliminodiacetic acid, hydroxyethyliminopropionic acid, hydroxypropyliminodiacetic acid, 2-hydroxycyclohexyliminodiacetic acid, methoxyethyliminodiacetic acid, 2-hydroxybenzyliminodiacetic acid, N-(o-carboxyphenyl)iminodiacetic acid, N-(m-carboxyphenyl) iminodiacetic acid, N-(p-carboxylphenyl)iminodiacetic acid, N-(carbamoylmethyl)iminodiacetic acid, cyanomethyliminodiacetic acid, aminoethyliminodiacetic acid, 2-ethoxycabonylaminoethyliminodiacetic acid, phosphonomethyliminodiacetic acid, phosphonoethyliminodiacetic acid, sulfoethyliminodiacetic acid, o-sulfophenyliminodiacetic acid, m-sulfophenyliminodiacetic acid, nitrilotriacetic acid, carboxyethyliminodiacetic acid, carboxymethyliminodipropionic acid, nitrilotripropionic acid, N,N'-ethylenediamine, ethylenediamine-N,N'-dipropionic acid, N,N'-di(hydroxyethyl)ethylenediamine diacetic acid, N-n-butylethylenediaminetriacetic acid, N-cyclohexylethylenediaminetriacetic acid, N'-hydroxyethyl-N,N,N'-triacetic acid, benzylethylenediaminetriacetic acid, ethylenediaminetetraacetic acid, ethylenediaminetetraacetic acid-zinc, ethylenediaminetetraacetic acid-disodium, ethylenediaminetetraacetic acid-calcium, ethylenediaminetetraacetic acid-magnesium, ethylenediaminetetraacetic acid-dipotassium, ethylenediamine-N,N'-diacetic acid N,N'-dipropionic acid, ethylenediamine-N,N'-di(2-propionic acid), ethylenediamine-N,N'-disuccinic acid, ethylenediamine-N,N'-diglutaric acid, ethylenediaminetetrapropionic acid, 1,2-propylenediaminetetraacetic acid, trimethylenediaminetetraacetic acid, tetramethylenediaminetetraacetic acid, pentamethylenediaminetetraacetic acid, hexamethylenediaminetetraacetic acid, octamethylenediaminetetraacetic acid, 1,2-cyclopentadiaminetetraacetic acid, trans-cyclohexane-1,2-diaminetetraacetic acid, cyclohexane-1,4-diaminetetraacetic acid, 1,3,5-triaminocyclohexaacetic acid, o-phenylenediaminetetraacetic acid, 2-hydroxytrimethylenediaminetetraacetic acid, ethyletherdiaminetetraacetic acid, hydantoic acid, (S,S)-ethylenediaminedisuccinic acid, (S,S)-ethylenediaminediglutaric acid, (S,S)-asparagic acid-N,N-diacetic acid, (S,S)-iminodisuccinic acid, (S)-glutamic acid-N,N-diacetic acid, (S)-α-alanine-N,N-diacetic acid and taurine-N,N-diacetic acid.

The examples of the amino acids are glycine, sarcosine, glycine methyl ester, valine, alanine, β-alanine, norleucine, leucine, isoleucine, phenylalanine, tyrosine, cysteine, methionine, serine, threonine, asparagine, glutamine, lysine, ε-polylysine, histidine, arginine, glutamic acid, polyglutamic acid, asparagic acid, 1,2-diaminopropionic acid, proline, tryptophan and N-ethylglycine.

The examples of the phosphoric acids are hexametaphosphoric acid, tetrametaphosphoric acid and condensed phosphoric acid. The examples of the phosphoric acids are ethylidenephosphonic acid, diethylenetriaminepenta(methylenephosphonic acid), methyldiphosphonic acid, nitrilotris (methylenephosphonic acid), ethylenediaminetetrakis-(methylenephosphonic acid) and 1,2-propylenediaminetetra (methylenephosphonic acid).

The examples of the inorganic sulfur compounds are thiosulfates (examples: sodium thiosulfate), polythionates (examples: $SO_3$—$(S)_n$—$SO_3$ (n=1 to 4)), dithionites (examples: sodium dithionite), sulfites (examples: sodium sulfite) and dithionates (examples: sodium dithionate).

There are no selecting conditions for water used other than considering to prevent the polymer from being contaminated. Water allowed to pass through a filter of 50 μm or less is preferred, and purified water which is treated with an ion-exchange resin is more preferred.

The examples of the electrolytic component are sodium chloride, ammonium chloride, sodium acetate, sodium phosphate, sodium citrate, sodium tartarate, sodium benzoate, sodium sorbate, sodium phthalate and sodium metabisulfate, and they may be potassium salts. The compounds which can be used as the electrolytic component are included in the compounds which are used for the complexing agent aqueous solution described above. When using the electrolytic component, at least one of them is added to the complexing agent aqueous solution.

Adsorbing treatment using activated carbon may be used in combination with the method described above in order to remove the residual catalyst. When solid-liquid contact of an ion exchange resin and an inorganic adsorbent with the polymer solution is used in combination, a method of a batch type in which stirring/mixing and solid-liquid separation are carried out by batch operation can be utilized. In addition thereto, capable of being utilized as well are a fixed bed system in which the polymer solution is allowed to pass through a vessel filled with an adsorbent, a moving bed system in which the solution is allowed to pass through a moving bed of an adsorbent and a continuous system such as a fluidized bed system in which adsorption is carried out with an adsorbent fluidized by a liquid. Further, mixing and dispersing operation can be combined, if necessary, with operation for elevating a dispersing efficiency such as shaking of a vessel and utilizing of a supersonic wave. After the polymer solution is brought into contact with the adsorbent, the adsorbent is removed by a method such as filtration, centrifugal separation and settling separation, and washing treatment with water is carried out if necessary, whereby the refining degree can further be raised.

The analytical methods of a molecular weight and a molecular weight distribution of the polymer (P-1) shall be explained. Usually, a molecular weight of an addition polymer can be measured by gel permeation chromatography (GPC) using a calibration curve in which a linear polymer such as polystyrene and poly (methyl methacrylate) is used as a standard sample. However, the polymer (P-1) belongs to a polymer of a vinyl base monomer originating in silsesquioxane, that is, a branched type high molecular compound. Accordingly, in determining a molecular weight of the polymer (P-1) having the above structure, it is considered that use of a calibration curve in which a linear polymer such as polystyrene and poly (methyl methacrylate) is used as a standard sample brings about a problem on an accuracy in molecular weight analysis. However, the polymer (P-1) has silsesquioxane at an end part thereof, and therefore it can readily be decomposed under an acid condition or a basic condition. That is, an accuracy in molecular weight analysis of the polymer part can further be enhanced by cutting off the addition polymer from silsesquioxane and then measuring a molecular weight thereof. Hydrofluoric acid is preferably used when decomposing the polymer (P-1) under an acid condition. Potassium hydroxide is preferably used when decomposing the polymer (P-1) under a basic condition. The polymer (P-1) can be decomposed in both of a homogeneous system and a heterogeneous system. For example, the silsesquioxane part of the polymer (P-1) can be cut off in a homogeneous mixed system of an organic solvent (THF, acetonitrile and the like) which can dissolve the polymer (P-1) and hydrofluoric acid. The silsesquioxane part can be decomposed as well in a heterogeneous mixed system of toluene and hydrofluoric acid. In this case, a phase transfer catalyst is preferably used in combination. The examples of the phase transfer catalyst are benzyltrimethylammonium chloride, tetramethylammonium chloride, tetrabutylammonium bromide, trioctylammonium chloride, dioctylmethylammonium chloride, triethylamine and dimethylaniline. When using potassium hydroxide, decomposition can be carried out as well in a mixed solvent of THF, ethanol and water.

The addition polymer cut off by the above methods is measured by GPC, whereby a molecular weight of an addition polymer part in the polymer (P-1), a molecular weight of a so-called graft chain can be determined. It is possible as well to determine a molecular weight of the polymer (P-1) itself by using a universal calibration curve obtained from the viscosity and the GPC data. An absolute molecular weight of the polymer (P-1) can be determined as well by an end group determination method, a membrane osmotic pressure method, a ultracentrifugal method and a light scattering method.

A preferred molecular weight of the graft chain in the polymer (P-1) falls in a range of 500 to 1,000,000 for a number average molecular weight in terms of poly (methyl methacrylate). The more preferred range is 1,000 to 100,000. However, the upper limit value and the lower limit value in this range do not necessarily have a specific meaning. The molecular weight distribution falls preferably in a range of 1.01 to 2.0 in terms of a dispersion degree (Mw/Mn).

The molecular weight of the graft chain can be controlled by a proportion of the vinyl base monomer to an α-haloester group which is an initiating group. That is, a theoretical molecular weight of the graft chain in the polymer (P-1) can be predicted from a mole ratio of the vinyl base monomer/α-haloester group and a consumption rate of the monomer using the following calculation equation:

$$Mn = \text{(consumption rate (mole \%) of monomer}/100) \times MW_M \times \text{(mole ratio of vinyl base monomer to } \alpha\text{-haloester group)} + MW_I$$

In the above calculation equation, Mn is a theoretical number average molecular weight; $MW_M$ is a molecular weight of the vinyl base monomer; and $MW_I$ is a molecular weight of the α-haloester group. When intending to obtain a polymer having the number average molecular weight range described above, a mole ratio of the vinyl base monomer/α-haloester group can be selected from a range of about 2/1 to about 40000/1, preferably about 10/1 to about 5000/1. The above number average molecular weight can be controlled as well by changing the polymerization time.

A theoretical molecular weight of the polymer (P-1) itself can be predicted as well from a mole ratio of the vinyl base monomer/the compound (1-1-2) and a consumption rate of the monomer using the following calculation equation:

$$Mn = \text{(consumption rate (mole \%) of monomer}/100) \times MW_M \times \text{(mole ratio of vinyl base monomer to compound (1-1-2))} + MW_I$$

In the above calculation equation, Mn is a theoretical number average molecular weight; $MW_M$ is a molecular weight of the vinyl base monomer; and $MW_I$ is a molecular weight of the compound (1-1-2).

Any method of GPC, $^1$H-NMR and gas chromatography can be adopted as a method for determining a consumption rate (hereinafter referred to as "a conversion rate") of the monomer.

The explanations described above regarding the polymer (P-1) can be applied to the polymer (P-2) and the polymer (P-3).

Next, a method for photopolymerizing the vinyl base monomer using the compound (1-4) as the initiator, a so-called photo initiator-transfer agent-terminator polymerizing method shall be explained. It is well known that in this photo initiator-transfer agent-terminator polymerization, a dithiocarbamate group is radically dissociated by light and has an excellent polymerization initiating ability and a sensitizing ability. It is well known as well that photopolymerization in this case is radical polymerization and that it is similar to living polymerization. These informations are disclosed in, for example, Polymer Bulletin, 11 (1984), 135- and Macromolecules, 19 (1986), 287-. Accordingly, the silicon compound of the present invention having a dithiocarbamate group can continue to maintain a polymerization initiating ability as long as irradiated with light, and it has a photopolymerization initiating ability for all radically polymerizable monomers.

It is known as well that a dithiocarbamate group has the respective functions of a polymerization initiator, a chain transfer agent and a photopolymerization terminator all together in photopolymerization, and the reaction mechanism thereof has already become clear. The compound (1-4) of the present invention having a dithiocarbamate group is dissociated into a radical on an alkylphenyl group bonded to the silicon compound and a dithiocarbamate radical by irradiating with light. Then, the radical on the alkylphenyl group takes part in the initiation of the reaction, and the dithiocarbamate radical takes part in the termination of the reaction. When irradiation with light is stopped or the monomer is exhausted, the dithiocarbamate radical is added to the growing end as a terminator to form again a dithiocarbamate group. Accordingly, the polymer thus formed can also be used as a polymer photoinitiator having a photopolymerization initiating ability. The silicon compound of the present invention having a dithiocarbamate group can initiate photopolymerization of a vinyl base monomer coexisting therewith by being decomposed by irradiating with a UV ray having a wavelength of 250 to 500 nm, preferably 300 to 400 nm having energy required for radically dissociating the dithiocarbamate group.

The form of carrying out the polymerization reaction can suitably be selected from bulk polymerization, solution polymerization, suspension polymerization, emulsion polymerization and bulk-suspension polymerization. A solvent used when producing by solution polymerization is preferably a solvent which has a small chain transfer constant and which can dissolve a vinyl base monomer and a polymer thereof. The examples of such preferred solvent are benzene, toluene, xylene, ethylbenzene, acetone, methyl ethyl ketone, methyl isobutyl ketone, ethyl acetate, methyl cellosolve, ethyl cellosolve, dimethylformamide, isopropyl alcohol, butanol, hexane and heptane. A solvent having no characteristic absorption in a UV ray area of 250 to 500 nm is rather preferred. The polymerization temperature falls in a range of 0 to 200° C., preferably room temperature to 150° C., but it shall not specifically be restricted.

The photo initiator-transfer agent-terminator polymerization can be carried out under reduced pressure, atmospheric pressure or applied pressure according to the kind of the vinyl base monomer and the kind of the solvent. It is important to carry out the polymerization usually under environment of inert gas such as nitrogen and argon, for example, under flowing of inert gas. Oxygen dissolved in the polymerization system has to be removed in advance under reduced pressure, and therefore it is possible as well to transfer to a polymerization step as it is under reduced pressure after finishing the step of removing dissolved oxygen.

When using a compound (1-4-2) as an initiator, a polymer obtained by the method described above is represented by Formula (P-4). In the following explanations, the polymer represented by Formula (P-4) is shown as the polymer (P-4):

(1-4-2)

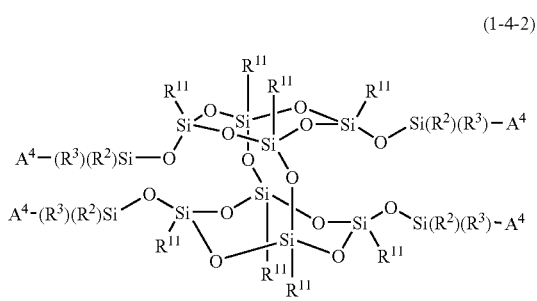

In Formula (1-4-2), $R^{11}$, $R^2$ and $R^3$ have the same meanings as those of these codes in Formula (1-1-2), and $A^4$ is a group represented by Formula (2-4):

(2-4)

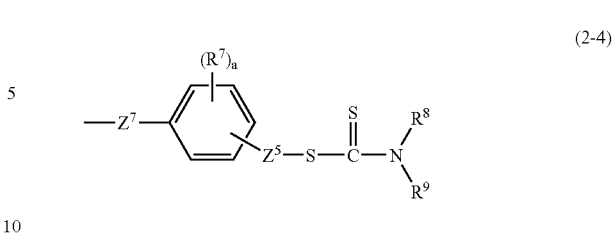

In Formula (2-4), $R^8$ and $R^9$ are independently hydrogen, alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; and a bonding position of $Z^5$ on the benzene ring is a meta position or a para position to a bonding position of $Z^7$, and a bonding position of $R^7$ is an optional position excluding the respective bonding positions of $Z^5$ and $Z^7$. Also when introducing $A^4$ as a polymerization initiator into a silsesquioxane derivative, a method in which a Grignard reagent is reacted with Si-halogen and a method in which a compound having an aliphatic unsaturated bond is reacted with Si—H can be used similarly to the case of obtaining the compound (1-1-2).

(P-4)

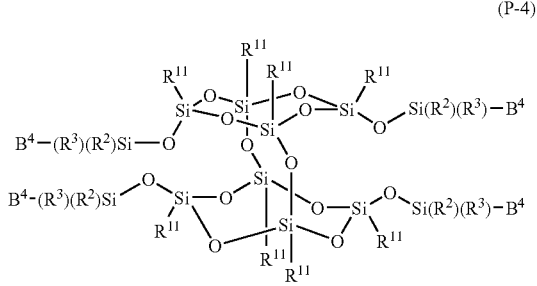

$R^{11}$, $R^2$ and $R^3$ in Formula (P-4) have the same meanings as those of these codes in Formula (1-4-2), and $B^4$ is a group represented by Formula (2-4-P):

(2-4-P)

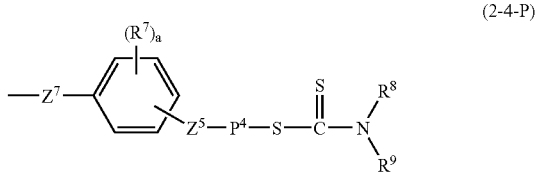

In Formula (2-4-P), $P^4$ is a group comprising the polymer of the vinyl base monomer, and the other codes have the same meanings as those of the codes in Formula (2-4). The bonding positions of $Z^5$ and $R^7$ on the benzene ring are the same as the bond positions thereof in Formula (2-4).

The structure of the polymer (P-4) can be controlled by the same method as in obtaining the polymer (P-1) by the atom transfer radical polymerization method. Silsesquioxane to which a high branched type polymer is bonded can be obtained by using an initiator monomer, for example, N,N-diethyldithiocarbamoylmetylstyrene or N-ethyldithiocarbamoylmetylstyrene in combination in polymerizing a conventional vinyl base monomer. After copolymerized with a vinyl base monomer having an initiating group which does not take part in photo initiator-transfer agent-terminator polymerization, the vinyl base monomer is further polymerized in the other polymerization mode (for example, an atom transfer radical polymerization method) using the resulting polymer as an initiator, whereby a graft copolymer can be formed. The examples of the vinyl base monomer having an initiating group which does not take part in the photo initiator-transfer agent-terminator polymerization are 1-(2-((4-ethenylphenyl)methoxy)-1-phenylethoxy-2,2,6,6-tetramethylpyridine, 1-(meth)acryloxy-2-phenyl-2-(2,2,6,6-tetramethyl-1-piperidinyloxy)ethane, (1-(4-((4-(meth)acryloxy)ethoxyethyl)phenylethoxy)piperidine, 2-(2-bromopropanoyloxy)ethyl (meth)acrylate, 2-(2-bromoisobutyryloxy)ethyl (meth)acrylate, p-chloromethylstyrene, 2-(2-bromopropanoyloxy)styrene and 2-(2-bromoisobutyryloxy)styrene.

After finishing the photo initiator-transfer agent-terminator polymerization, the end dithiocarbamate group thereof is treated, whereby the polymer (P-4) can be deactivated against a UV ray. The examples of a deactivating method are a method in which the polymer (P-4) is treated in an acid solution or a basic solution, a method in which the polymer is treated at a high temperature of 250° C. or higher, a method in which the polymer is irradiated with an electromagnetic beam of high energy having a wavelength of 220 nm or less, a method in which a monomer having a UV ray-absorbing group is added and then photopolymerized and a method in which a UV ray-absorbing agent is merely added. It is possible as well to substitute the end dithiocarbamate group by adding a reagent having a large chain transfer constant (thiol derivatives, thiuram, xanthates and nitroxides) while irradiating the polymer (P-4) obtained with a UV ray.

A method for isolating and refining the polymer (P-4) shall be explained. This compound is isolated and refined by efficiently removing the unreacted vinyl base monomer. Various methods are available, and a refining method carried out by the reprecipitating operation described above is preferred. This method makes it possible to precipitate only the polymer (P-4) in a poor solvent and readily separate the polymer from the unreacted monomer by filtering operation. The polymer may be isolated by distilling off volatile components such as the solvent and the unreacted monomer under a condition of reduced pressure. A preferred solvent for dissolving the polymer (P-4) is a solvent having a large dissolving power and a relatively low boiling point. A preferred precipitant is a solvent which is compatible with the solvent for the polymer (P-4) and does not dissolve at all the polymer (P-4) and which dissolves only the impurities or the unreacted monomer and has a relatively low boiling point. The examples of the preferred precipitant are lower alcohols and aliphatic hydrocarbons. The particularly preferred precipitant is methanol or hexane. It is advisable to increase the repeating frequency of the reprecipitating operation in order to further raise the refining degree.

A molecular weight and a molecular weight distribution of the polymer (P-4) can be analyzed by the same method as explained in the polymer (P-1). The polymer of the vinyl base monomer bonded to silsesquioxane, a so-called graft chain has a number average molecular weight falling in a range of 500 to 1,000,000. The more preferred range is 1,000 to 100,000. However, the upper limit value and the lower limit value in this range do not have a specific meaning. A molecular weight distribution of the graft chain falls preferably in a range of 1.01 to 3.0 in terms of a dispersion degree. It is possible as well to determine a molecular weight of the polymer (P-4) by using a universal calibration curve obtained from the viscosity and the GPC data. An absolute molecular weight of the polymer (P-4) can be determined as well by an end group determination method, a membrane osmotic pressure method, a ultracentrifugal method and a light scattering method. A molecular weight of the graft chain in the polymer (P-4) can be controlled in the same manner as in the case of the polymer (P-1).

EXAMPLES

The present invention shall more specifically be explained with reference to examples, but the present invention shall not be restricted to the following examples.

Codes used in the examples have the following meanings.

Ph: phenyl

TMS: trimethylsilyl

Mn: number average molecular weight

Mw: weight average molecular weight

EDTA.2Na: disodium ethylenediaminetetraacetate-.dihydrate

All the data of molecular weights in the examples were polystyrene-reduced values determined by GPC (gel permeation chromatography). The measuring conditions of GPC are shown below.

Apparatus: JASCO GULLIVER1500 (intelligent differential refractometer RI-1530), manufactured by JASCO Corp.

Solvent: tetrahydrofuran (THF)

Flow velocity: 1 ml/minute

Column temperature: 40° C.

Columns used: the following columns (used connecting in series) manufactured by Tosoh Co., Ltd.

TSKguardcolumn HXL-L (GUARDCOLUMN)

TSKgel G1000HxL (excluded critical molecular weight (polystyrene): 1,000)

TSKgel G2000HxL (excluded critical molecular weight (polystyrene): 10,000)

Standard sample for calibration curve: Polymer Standards (PL), Polystyrene, manufactured by Polymer Laboratories Co., Ltd.

In Examples 6 to 19, Shodex KF-G (GUARDCOLUMN) and 2 columns of Shodex KF-804L (excluded critical molecular weight (polystyrene): 400,000) manufactured by Showa Denko K. K. were used connecting in series, and Shodex STANDARD M-75 (polymethyl methacrylate) manufactured by Showa Denko K. K. was used as a standard sample for a calibration curve. The other conditions are the same as described above.

Example 1

<Synthesis of Compound (3-1-1): Phenylsilsesquioxane to which Sodium is Bonded>

A reactor having a content volume of 50 liter equipped with a reflux condenser, a thermometer and a stirrer was charged with phenyltrimethoxysilane (6.54 kg), 2-propanol (26.3 liter), purified water (0.66 kg) and sodium hydroxide (0.88 kg) and sealed with dry nitrogen. The reactor was heated while heating to react them for 5 hours in a refluxing state. After finishing the reaction, the heater was detached from the reactor, and this vessel was left standing at room temperature for 15 hours to cool the reaction mixture. A supernatant was removed from the reaction mixture thus obtained by decantation.

Then, a white solid matter remaining in the reactor was washed once with 2-propanol (9.87 kg). This was transferred into a stainless bat lined with a polytetrafluoroethylene sheet and dried at an inner temperature of 80° C. and a pressure of $6.7 \times 10^{-4}$ MPa for 24 hours by means of a dryer under reduced pressure to obtain 2.22 kg of a white powder-like compound (A-1).

Example 2

<Introduction of Trimethylsilyl Group into Compound (A-1)>

A four neck flask of 50 ml equipped with a reflux condenser was charged with the compound (A-1) (1.2 g), tetrahydrofuran (10 g) and triethylamine (1.6 g) and sealed with dry nitrogen. Trimethylchlorosilane (2.2 g) was dropwise added thereto in about one minute while maintaining a solution temperature at 15 to 20° C. under stirring by means of a magnetic stirrer. After finishing dropwise adding, stirring was continued at 15° C. for 3.5 hours. After finishing the reaction, the reaction product was washed with purified water and dried under vacuum to obtain a white solid matter (1.2 g). This is designated as a compound (A-T).

The compound (A-T) was subjected to structural analysis by means of gel permeation chromatography (GPC), $^1$H-NMR and $^{29}$Si-NMR. It was confirmed from a GPC chart that the white solid matter showed monodispersibility and that it had a number average molecular weight of 970 and a weight average molecular weight of 990 in terms of polystyrene. It was confirmed from a $^1$H-NMR chart that a phenyl group and a trimethylsilyl group were present in an integral ratio of 2:1. It was confirmed from a $^{29}$Si-NMR chart that two peaks having a phenyl group and originating in a T structure were present in −76.12 ppm and −78.95 ppm in an integral ratio of 1:1 and that one peak (all based on tetramethylsilane) originating in a trimethylsilyl group was present in 10.62 ppm. The above results support that the compound (A-T) has a structure represented by Formula (3-T). Accordingly, the compound (A-1) is a compound having a structure represented by Formula (3-1-1). The T structure is a term showing a partial structure in which three oxygen atoms are bonded to one silicon atom, that is, $-Si(O-)_3$.

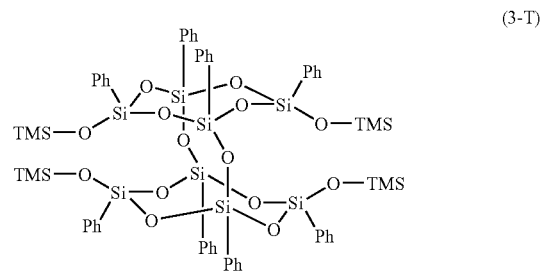

(3-T)

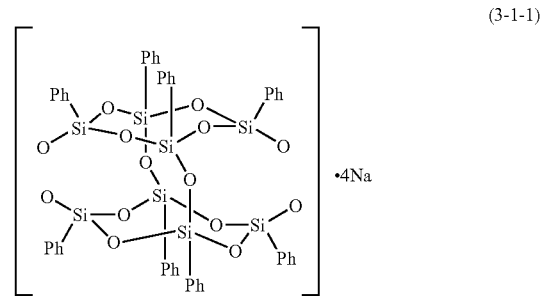

(3-1-1)

Example 3

<Synthesis of Compound (5-1): Organic Silicon Compound having a Hydrosilyl Group>

A four neck flask having a content volume of 1000 ml equipped with a dropping funnel, a thermometer and a reflux condenser was charged with a rotator, the compound (3-1-1) (69 g) obtained by making use of the method in Example 1 and toluene (540 g), and the flask was sealed with dry nitrogen. Dimethylchlorosilane (9.1 g) was dropwise added thereto from the dropping funnel in about 35 minutes while stirring by means of a magnetic stirrer. In this case, the dropping speed was controlled so that the solution temperature was 25 to 35° C. After finishing dropwise adding, the flask was heated while stirring, and stirring was continued in a refluxing state for 3 hours to complete the reaction. After finishing the reaction, the flask was left cooling so that the solution temperature was lowered down to 50° C. or lower. Then, 160 g of purified water was slowly dropwise added thereto from the dropping funnel. After finishing dropwise adding, the solution was stirred for about 10 minutes to hydrolyze unreacted dimethylchlorosilane and dissolve sodium chloride. The reaction mixture thus obtained was transferred into a separating funnel to separate an organic layer from an aqueous layer. The organic layer thus obtained was washed with saturated brine, and then it was repeatedly washed with water so that the washing solution became neutral. The organic layer obtained was dried on anhydrous magnesium sulfate and concentrated under reduced pressure by means of a rotary evaporator to obtain 71 g of a white solid matter. This white solid matter was washed with normal heptane (350 ml) and dried under reduced pressure to obtain 50 g of a white powder-like solid matter.

The structure of the white solid matter thus obtained was analyzed by means of gel permeation chromatography (GPC), $^1$H-NMR, 29 Si-NMR and IR analysis. It was confirmed from a GPC chart that the white solid matter was monodispersed and that it had a number average molecular weight of 900 and a weight average molecular weight of 910 in terms of polystyrene. It was confirmed from a $^1$H-NMR chart that an integral ratio based on a phenyl group, a hydrosilyl group and a methyl group was 40:4:24. A peak indicating a dimethylsilyl group was confirmed in −3.28 ppm (based on tetramethylsilane) from a $^{29}$Si-NMR chart. Further, absorption based on stretching vibration of Si—H was confirmed. in 2142 cm$^{-1}$ from an IR spectrum measured by a KBr tablet method. The above results indicate that the compound obtained by reacting the compound (3-1-1) with dimethylchlorosilane has a structure represented by Formula (5-1):

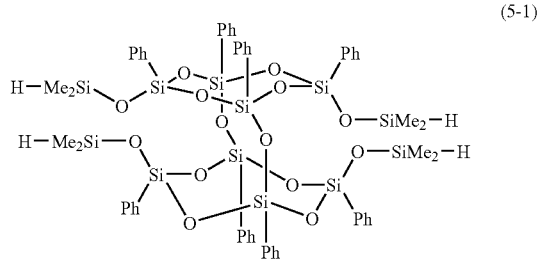

(5-1)

liquid temperature was maintained at 42° C. while stirring by means of a magnetic stirrer. A platinum-divinyltetramethyldisiloxane complex/xylene solution (platinum content: 3.0% by weight, 33 µl) was added thereto by means of a microsyringe, and then the reaction liquid temperature was elevated to 60° C. by heating to continue stirring for 2 hours. Then, the reaction liquid was sampled and subjected to IR analysis to result in confirming that absorption in 2,138 cm$^{-1}$ indicating an Si—H group disappeared. Subsequently, the reaction liquid was concentrated under reduced pressure, and then the residue was diluted to 20% by weight by ethyl acetate (28 g). Then, powder activated carbon (0.4 g) was added thereto, and stirring was continued for 1.5 hour. The activated carbon was removed by filtration, and then the solution was concentrated under reduced pressure to obtain 6.6 g of a viscous transparent liquid.

The viscous liquid thus obtained was subjected to IR analysis by a liquid membrane method to result in confirming absorption based on O—H stretching vibration of a hydroxyl group in 3450 cm$^{-1}$. $^{29}$ Si-NMR analysis thereof was carried out to result in confirming a peak of 11.42 ppm corresponding to a (3-(2-hydroxyethyloxy)propyl)dimethylsilyl group. GPC analysis thereof was carried out to result in finding that it had a number average molecular weight of 1180 and a weight average molecular weight of 1230 in terms of polystyrene. It was indicated from the above data that the viscous liquid was a compound having a structure represented by Formula (7-1):

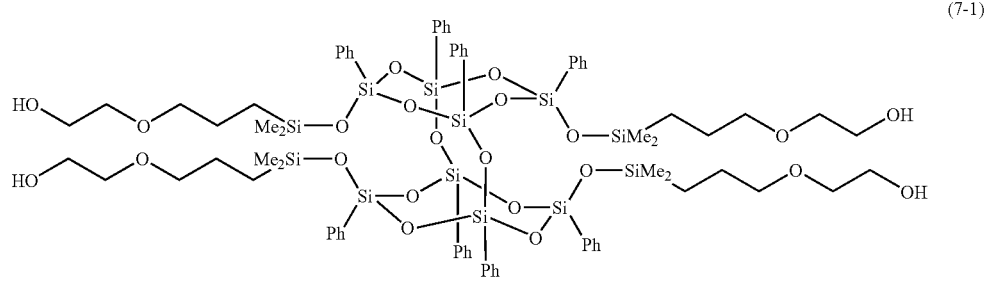

(7-1)

Example 4

<Synthesis of Silicon Compound having a Hydroxyethoxypropyl Group>

A four neck flask of 50 ml equipped with a reflux condenser, a dropping funnel, a thermometer and a rotator was charged with the compound (5-1) (5.2 g) obtained by making use of the method of Example 3, ethylene glycol monoallyl ether (6.6 g) and toluene (5.2 g), and it was sealed with dry nitrogen. The flask was heated so that a reaction Example 5

<Synthesis of Silicon Compound having a 2-bromo-2-methylpropanoyloxyethoxypropyl Group>

A Kjeldahl flask having a volume content of 100 ml was charged with the compound (7-1) (1.0 g) obtained in Example 4, triethylamine (0.35 g) dried on molecular sieves (4A) and dry methylene chloride (10 ml) under argon atmosphere. The compound (7-1) was dissolved therein while stirring at room temperature by means of a magnetic stirrer, and then the solution was cooled on a dry ice-methanol bath to maintain a solution temperature at −78° C.

Then, 2-bromo-2-methylpropanoyl bromide (0.81 g, 6.0 equivalent based on the compound (7-1)) was quickly added to the above solution and stirred at −78° C. for one hour, and then the solution was further stirred at room temperature for 2 hours. After finishing the reaction, a triethylamine-hydrobromic acid salt was removed by filtration. Methylene chloride (50 ml) was added to the reaction liquid obtained, and it was washed in order once with water (100 ml), twice with a sodium hydrogencarbonate aqueous solution (1%, 100 ml) and twice with water (100 ml), followed by drying it on anhydrous magnesium sulfate (5 g). Then, the above solution was concentrated at room temperature by means of a rotary evaporator to reduce a solution amount to about 5 ml. Methanol (50 ml) was added to the above concentrate (5 ml) to carry out phase separation of a viscous liquid component. Thereafter, it was left standing still in a freezing chamber (−35° C.) to sufficiently carry out the phase separation of the viscous liquid component, and then this component was obtained by decantation. The above viscous transparent liquid was refined by a column chromatography and dried under reduced pressure at 40° C. for 6 hours to obtain a transparent viscous liquid (0.86 g, yield: 63.7%).

The above viscous liquid had a GPC purity of 98.3%. It was found from the results of $^1$H-NMR, $^{13}$C-NMR and $^{29}$Si-NMR each shown below that the above compound had a structure represented by Formula (1-1-3).

$^1$H NMR (400 MHz, CDCl$_3$, TMS standard: δ=0.0 ppm): 7.55 to 7.10 (m, 40H, Ph-Si), 4.17 (t, 8H, —[CH$_2$]—O—(C=O)—), 3.39 (t, 8H, —[CH$_2$]—O—C$_2$H$_4$—), 2.98 (t, 8H, —C$_3$H$_6$—O—[CH$_2$]—), 1.89 (s, 24H, —C(Br)[(CH$_3$)$_2$]), 1.29 (tt, 8H, —CH$_2$—[CH$_2$]—CH$_2$—), 0.42 (t, 8H, Si—[CH$_2$]—), 0.27 (s, 24H, —OSi[(CH$_3$)$_2$]—).

$^{13}$C NMR (100 MHz, CDCl$_3$, TMS standard: δ=0.0 ppm): 171.8 (C=O), 134.5 to 127.7 (Ph-Si), 73.9 (—[CH$_2$]—O—C$_2$H$_4$—), 67.9 (—C$_3$H$_6$—O—[CH$_2$]—), 65.1 (—[CH$_2$]—O—(C=O)—), 55.8 (—[C] (Br) (CH$_3$)$_2$), 30.8 (—C(Br)[(CH$_3$)$_2$]), 23.1 (—CH$_2$—[CH$_2$]—CH$_2$—), 14.0 (Si—[CH$_2$]—), −0.30 (—OSi[(CH$_3$)$_2$]—).

$^{29}$Si NMR (79 MHz, CDCl$_3$, TMS standard: δ=0.0 ppm): 11.31 (—O[Si] (CH$_3$)$_2$CH$_2$—), −76.10, −78.85 (Ph-SiO$_{1.5}$).

carried out three times by means of a vacuum device equipped with an oil-sealed rotary pump, and the ampul was quickly sealed by means of a hand burner while maintaining a state of vacuum. In this case, a proportion of the compound (1-1-3), methyl methacrylate, cuprous bromide and L-(−)-sparteine was set to 1:1200:4:8 in terms of a mole ratio in the above order, and a use amount of anisole was set to such an amount that a concentration of methyl methacrylate became 50% by weight.

<Polymerization>

The sealed heat resistant glass-made ampul was set in a constant temperature shaking bath, and polymerization was carried out to obtain a brown viscous solution of a polymer (a) was obtained. In this case, the polymerization temperature was 70° C., and the polymerization time was 0.5 hour. A monomer conversion rate in this polymerization reaction system was determined from the relation of a proton ratio of the substituent in each of the monomer and the polymer by diluting the solution of the polymer (a) with deuterated chloroform and then subjecting the solution to $^1$H-NMR measurement. The polymer (a) obtained was recovered by reprecipitation refining from hexane, and an ethyl acetate solution (5% by weight) of the above polymer (a) was prepared to carry out flushing together with an EDTA.2Na aqueous solution (2% by weight, 100 ml) by means of a 300 ml-separating funnel, whereby the copper complex was removed by adsorption. Further, this solution was dropwise added to hexane to reprecipitate the polymer, and it was dried (80° C., 6 hours) under reduced pressure. Shown in Table 6-1 are the analytical results of a monomer conversion rate in the above polymerization reaction system, a theoretical number average molecular weight of the polymer (a) derived from the monomer conversion rate, the number average molecular weight actually measured by GPC and the molecular weight distribution.

<Analysis of Theoretical Molecular Weight of Graft Chain>

A theoretical molecular weight of the graft chain was calculated from the following equation assuming that an ester bond which was an initiating end in the polymerization

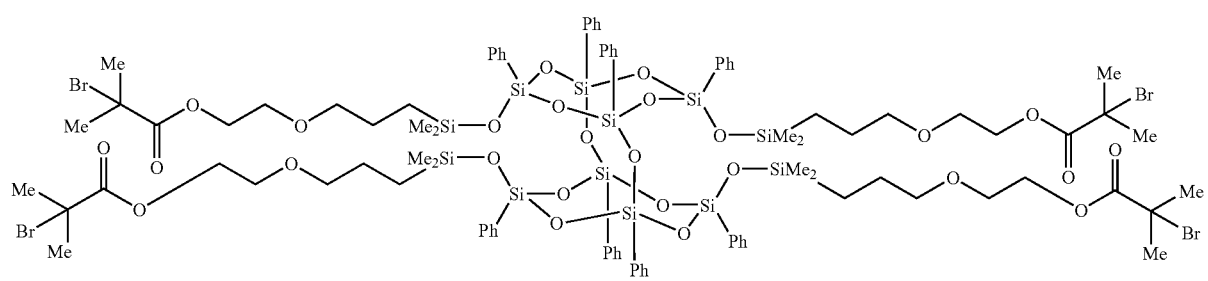

(1-1-3)

Example 6

<Preparation of Solution for Polymerization>

Cuprous bromide was introduced into a heat resistant glass-made ampul in a draft which was cut off from a UV ray, and the compound (1-1-3) obtained in Example 5/methyl methacrylate/L-(−)-sparteine/anisole solution was further added thereto and quickly cooled using liquid nitrogen. Then, frozen vacuum deaeration (pressure: 1.0 Pa) was was cut off by hydrolysis brought about by hydrofluoric acid treatment and that all terminating ends in the polymerization had become Br. The results thereof are shown in Table 6-2.

<Calculating Equation>

Theoretical $Mn$ of graft chain=(monomer consumption rate (mole %)/100)×$MW_M$×(mole ratio of vinyl base monomer to α-bromoester group)+$MW_1$ <Parameters Used for Calculation>
 $MW_M$=100 (methyl methacrylate)
 Mole ratio of vinyl base monomer to α-bromoester group=300 $MW_1$=167.01 (BrC(CH$_3$)$_2$CO$_2$H)

<Molecular Weight Measurement of Graft Chain>
A mixed solution of hydrofluoric acid (0.17 ml) and acetonitrile (0.83 ml) was prepared. The polymer (a) (10 mg) was dissolved in the above mixed solution in a polypropylene-made microtube (1.5 ml) into which a rotator was introduced, and the solution was stirred at 40° C. for 24 hours in an incubator equipped with a magnetic stirrer. Then, drying was carried out at 80° C. for 3 hours in a vacuum dryer to recover the polymer. The above polymer was subjected to GPC measurement, and the results thereof are shown in Table 6-2.

Examples 7 to 12

Polymerization was carried out in the same manner as in Example 6 to obtain the respective brown viscous solutions of a polymer (b) to a polymer (g), except that the polymerization time was changed as shown in Table 6-1. Then, the respective polymers were refined in the same manner as in Example 6 to determine a monomer conversion rate, a theoretical number average molecular weight, a number average molecular weight and a molecular weight distribution, and the results thereof are shown Table 6-1. Calculation of a theoretical number average molecular weight of the graft chain, treatment of the polymer by hydrofluoric acid and analysis of a number average molecular weight and a molecular weight distribution of the graft chain measured by GPC were carried out as well in the same manners as in Example 6, and the results thereof are shown in Table 6-2.

TABLE 6-1

| Example | Polymer | Polymerization time (hr) | Conversion rate (mol-%) | Mn theoretical value | Mn measured value | Mw/Mn measured value |
|---|---|---|---|---|---|---|
| 6 | a | 0.5 | 17.0 | 22,700 | 20,900 | 1.13 |
| 7 | b | 1.0 | 29.6 | 37,800 | 34,200 | 1.13 |
| 8 | c | 1.5 | 42.8 | 53,700 | 47,500 | 1.15 |
| 9 | d | 2.0 | 51.0 | 63,500 | 58,300 | 1.15 |
| 10 | e | 3.0 | 61.1 | 75,600 | 72,200 | 1.16 |
| 11 | f | 4.0 | 63.0 | 78,000 | 76,600 | 1.15 |
| 12 | g | 5.0 | 75.7 | 93,200 | 93,000 | 1.17 |

TABLE 6-2

| Example | Polymer | Mn theoretical value | Mn measured value | Mw/Mn measured value |
|---|---|---|---|---|
| 6 | a | 5,300 | 7,200 | 1.12 |
| 7 | b | 9,000 | 10,400 | 1.11 |
| 8 | c | 13,000 | 14,100 | 1.1 |
| 9 | d | 15,500 | 17,000 | 1.1 |
| 10 | e | 18,500 | 20,500 | 1.12 |
| 11 | f | 19,100 | 22,200 | 1.11 |
| 12 | g | 22,900 | 28,400 | 1.08 |

Example 13

<Preparation of Solution for Polymerization>
Cuprous bromide was introduced into a heat resistant glass-made ampul in a draft which was cut off from a UV ray, and the compound (1-1-3)/methyl methacrylate/L-(−)-sparteine/anisole solution was further added thereto and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of the hand burner while maintaining a state of vacuum. In this case, a proportion of the compound (1-1-3), methyl methacrylate, cuprous bromide and L-(−)-sparteine was set to 1:600:4:8 in terms of a mole ratio in the above order, and a use amount of anisole was set to such an amount that a concentration of methyl methacrylate became 50% by weight.

<Polymerization>
The sealed heat resistant glass-made ampul was set in a constant temperature shaking bath, and polymerization was carried out to obtain a brown viscous solution of a polymer (2a). In this case, the polymerization temperature was 70° C., and the polymerization time was 0.25 hour. A monomer conversion rate in this polymerization reaction system was determined from the relation of a proton ratio of the substituent in each of the monomer and the polymer by diluting the solution of the polymer (2a) with deuterated chloroform and then subjecting the solution to $^1$H-NMR measurement. The polymer (2a) obtained was recovered by reprecipitation refining from hexane, and an ethyl acetate solution (5% by weight) of the above polymer (2a) was prepared to carry out flushing together with an EDTA.2Na aqueous solution (2% by weight, 100 ml) by means of a 300 ml-separating funnel, whereby the copper complex was removed by adsorption. Further, this solution was dropwise added to hexane to reprecipitate the polymer (2a), and it was dried (80° C., 6 hours) under reduced pressure. Shown in Table 7-1 are the analytical results of a monomer conversion rate in the above polymerization reaction system, a theoretical number average molecular weight of the polymer (2a) derived from the monomer conversion rate, the number average molecular weight actually measured by GPC and the molecular weight distribution.

<Analysis of Theoretical Molecular Weight of Graft Chain>
A theoretical molecular weight of the graft chain was calculated from the following equation assuming that an ester bond which was an initiating end in the polymerization was cut off by hydrolysis brought about by hydrofluoric acid treatment and that all terminating ends in the polymerization had become Br. The results thereof are shown in Table 7-2.

<Calculating Equation>

Theoretical $Mn$ of graft chain=(monomer consumption rate (mole %)/100)×$MW_M$×(mole ratio of vinyl base monomer to α-bromoester group)+$MW_1$ <Parameters Used for Calculation>
 $MW_M$=100 (methyl methacrylate)
 Mole ratio of vinyl base monomer to α-bromoester group=150
 $Mw_1$=167.01 (BrC(CH$_3$)$_2$CO$_2$H)

<Molecular Weight Measurement of Graft Chain>
A mixed solution of hydrofluoric acid (0.17 ml) and acetonitrile (0.83 ml) was prepared. The polymer (2a) (10 mg) was dissolved in the above mixed solution in a polypropylene-made microtube (1.5 ml) into which a rotator was introduced, and the solution was stirred at 40° C. for 24 hours in an incubator equipped with a magnetic stirrer. Then, drying was carried out at 80° C. for 3 hours in a vacuum dryer to recover the polymer. The polymer recovered was subjected to GPC measurement, and the results thereof are shown in Table 7-2.

Examples 14 to 19

Polymerization was carried out in the same manner as in Example 13 to obtain the respective brown viscous solutions of a polymer (2b) to a polymer (2 g), except that the polymerization time was changed as shown in Table 7-1. Then, the respective polymers were refined in the same manner as in Example 13 to determine a monomer conversion rate, a theoretical number average molecular weight, a number average molecular weight and a molecular weight distribution, and the results thereof are shown Table 7-1. Calculation of a theoretical number average molecular weight of the graft chain, treatment of the polymer by hydrofluoric acid and analysis of a number average molecular weight and a molecular weight distribution of the graft chain measured by GPC were carried out as well in the same manners as in Example 13, and the results thereof are shown Table 7-2.

TABLE 7-1

| Example | Polymer | Polymerization time (hr) | Conversion rate (mol-%) | Mn theoretical value | Mn measured value | Mw/Mn measured value |
|---|---|---|---|---|---|---|
| 13 | 2a | 0.25 | 14.2 | 10,800 | 9,200 | 1.13 |
| 14 | 2b | 0.5 | 23.6 | 16,500 | 15,800 | 1.16 |
| 15 | 2c | 1.0 | 40.5 | 26,600 | 24,600 | 1.14 |
| 16 | 2d | 1.5 | 51.7 | 33,300 | 31,100 | 1.16 |
| 17 | 2e | 2.0 | 69.3 | 43,900 | 43,800 | 1.19 |
| 18 | 2f | 2.5 | 74.1 | 46,800 | 49,000 | 1.18 |
| 19 | 2g | 3.0 | 78.1 | 49,200 | 50,900 | 1.20 |

TABLE 7-2

(data of graft chain)

| Example | Polymer | Mn theoretical value | Mn measured value | Mw/Mn measured value |
|---|---|---|---|---|
| 13 | 2a | 2,300 | 3,800 | 1.12 |
| 14 | 2b | 3,700 | 5,700 | 1.13 |
| 15 | 2c | 6,200 | 8,100 | 1.1 |
| 16 | 2d | 7,900 | 9,900 | 1.11 |
| 17 | 2e | 10,600 | 13,100 | 1.11 |
| 18 | 2f | 11,300 | 14,500 | 1.1 |
| 19 | 2g | 11,900 | 14,800 | 1.12 |

Example 20

Synthesis of a Compound (3-2-1): Phenylsilsesquioxane having Silanol Obtained by using the Compound (3-1-1) as a Raw Material>

A reactor having a volume content of 100 ml equipped with a dropping funnel and a thermometer was charged with the compound (3-1-1) (6 g) obtained in Example 1 and tetrahydrofuran (50 ml), and it was sealed with dry nitrogen. Then, glacial acetic acid (2.4 g) was dropwise added thereto in about 10 seconds while stirring to maintain a solution temperature at 22 to 27° C. After finishing dropwise adding, stirring was continued at room temperature for one hour, and then ion-exchanged water (20 g) was dropwise added thereto. After finishing dropwise adding, stirring was continued for 10 minutes, and then the solution was transferred into a separating funnel to separate an organic layer from an aqueous layer. The organic layer thus obtained was washed once with a saturated sodium hydrogencarbonate aqueous solution, and then washing with ion-exchanged water was repeated to neutrality. Next, the organic layer was dried on anhydrous magnesium sulfate and then concentrated under reduced pressure to obtain 5.3 g of a white powder-like solid matter.

The white powder-like solid matter thus obtained was subjected to IR analysis to confirm absorption based on stretching of Si—OH in 3300 cm$^{-1}$. Measurement of $^{29}$Si-NMR resulted in confirming each one signal originating in a structure represented by PhSi(OH)O$_{2/2}$ in −69.32 ppm and originating in a structure represented by PhSiO$_{3/2}$ in −79.45 ppm. Measurement of $^1$H-NMR resulted in finding that signals other than that of a phenyl group were not confirmed. Measurement of an average molecular weight by GPC resulted in finding that the solid matter had a number average molecular weight of 760 and a weight average molecular weight of 780 in terms of polystyrene. The above data indicate that the white powder-like solid matter obtained has a structure of Formula (3-2-1):

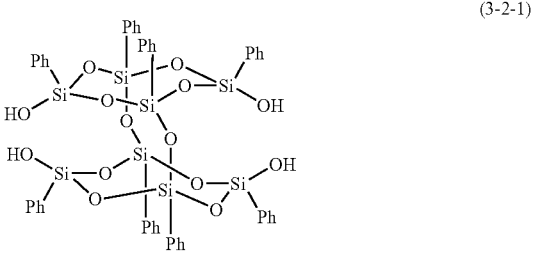

(3-2-1)

Example 21

<Synthesis of a Compound (5-1): Organic Silicon Compound having a Hydrosilyl Group>

The same operation as in Example 3 is carried out, except that the compound (3-2-1) obtained in Example 20 is substituted for the compound (3-1-1) obtained in Example 1, whereby a compound (5-1) can be synthesized:

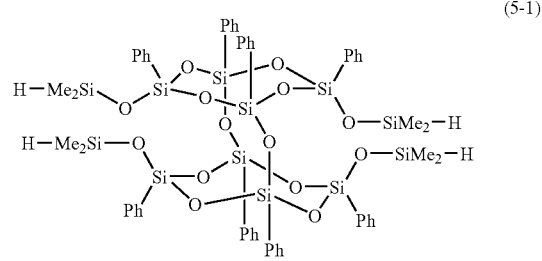

(5-1)

Example 22

<Synthesis of a Silicon Compound having a Hydroxypropyl Group>

The same operation as in Example 4 is carried out, except that allyl alcohol (4.0 equivalent or more based on the compound (5)) is substituted for ethylene glycol monoallyl ether, whereby a compound represented by Formula (7-2) can be synthesized:

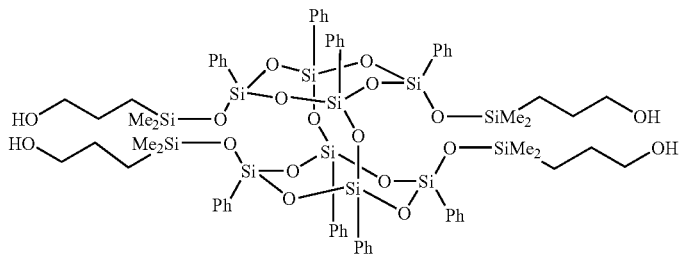

(7-2)

Example 23

<Synthesis of a Silicon Compound having a 2-bromo-2-methylpropanoyloxypropyl Group>

The same operation as in Example 5 is carried out, except that the compound (7-2) obtained in Example 22 is substituted for the compound (7-1) obtained in Example 4, whereby a silicon compound represented by Formula (1-1-4) can be synthesized:

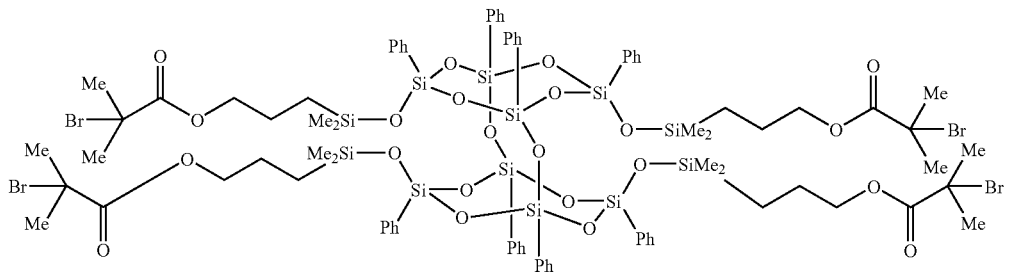

(1-1-4)

Example 24

<Synthesis of a Silicon Compound having a Chloromethylphenylethyl Group>

The same operation as in Example 4 is carried out, except that chloromethylstyrene (4.0 equivalent or more based on the compound (5)) is substituted for ethylene glycol monoallyl ether, whereby a compound represented by Formula (1-3-3) can be synthesized:

(1-3-3)

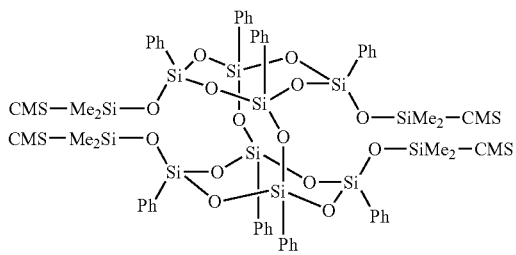

CMS in the above formula is a group represented by any of the following formulas:

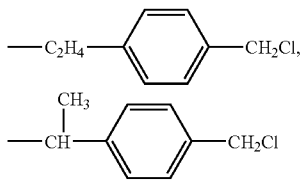

Example 25

<Synthesis of a Silicon Compound having a Dithiocarbamoyl Group>

The compound (1-3-3) obtained in Example 24 which is used as a raw material is reacted with sodium N,N-diethylthiocarbamate.trihydrate (1.0 equivalent or more based on a chloromethylphenylethyl group) in tetrahydrofuran, whereby a silicon compound having a dithiocarbamoyl group represented by Formula (1-4-3) can be synthesized:

(1-4-3)

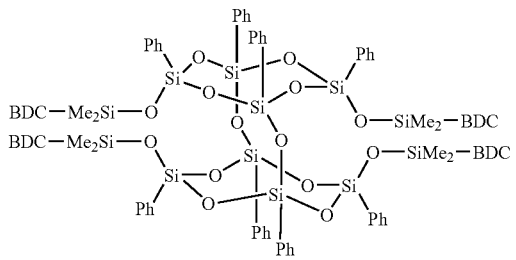

BDC in the above formula is a group represented by any of the following formulas:

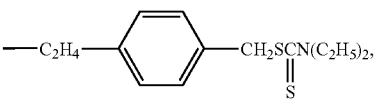

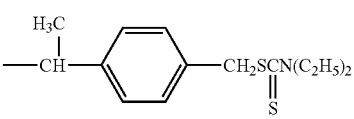

Example 26

<Synthesis of 2-bromo-2-methylpropanoyloxypropyldimethylchlorosilane>

Allyl alcohol used as a raw material is reacted with 2-bromo-2-methylpropanoyl bromide (1.0 equivalent or more based on a hydroxyl group) in methylene chloride in the presence of triethylamine (1.0 equivalent or more based on a hydroxyl group), whereby a compound represented by Formula (10) is synthesized. Further, the compound (10) and dimethylchlorosilane (1.0 equivalent or more based on an allyl group) are subjected to hydrosilylation reaction with a platinum-divinyltetramethyldisiloxane complex/xylene solution ($1\times10^{-6}$ to $1\times10^{-2}$ mole per mole of an Si—H group in terms of a transition metal atom) used as a catalyst, whereby 2-bromo-2-methylpropanoyloxypropyldimethylchlorosilane represented by Formula (11-1) can be synthesized:

(10)

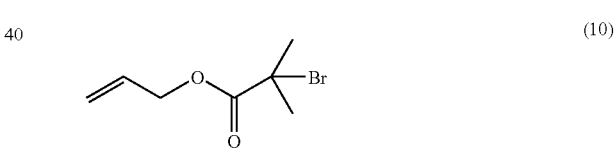

(11-1)

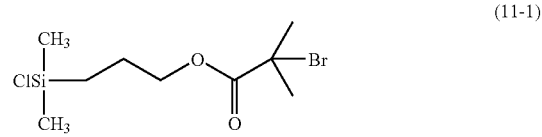

Example 27

<Synthesis of a Silicon Compound having a 2-bromo-2-methylpropanoyloxypropyl Group>

The same operation as in Example 3 is carried out, except that 2-bromo-2-methylpropanoyloxypropyldimethylchlorosilane (4.0 equivalent or more based on the compound (3-1-1)) obtained in Example 26 is substituted for dimethylchlorosilane, whereby a silicon compound represented by Formula (1-1-4) can be synthesized:

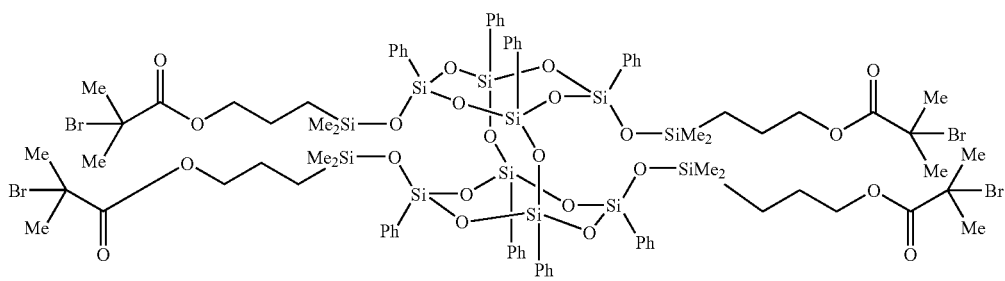

(1-1-4)

Example 28

<Synthesis of a Silicon Compound having a 2-bromo-2-methylpropanoyloxypropyl Group>

The same operation as in Example 27 is carried out, except that the compound (3-2-1) is substituted for the compound (3-1-1), whereby the silicon compound represented by Formula (1-1-4) can be synthesized.

Example 29

Example 30

<Synthesis of a Silicon Compound having a 2-bromo-2-methylpropanoyloxyethoxypropyl Group>

The same operation as in Example 27 is carried out, except that 2-bromo-2-methylpropanoyloxyethoxypropyldimethylchlorosilane (4.0 equivalent or more based on the compound (3-1-1)) obtained in Example 29 is substituted for 2-bromo-2-methylpropanoyloxypropyldimethylchlorosilane obtained in Example 26, whereby a silicon compound represented by Formula (1-1-3) can be synthesized:

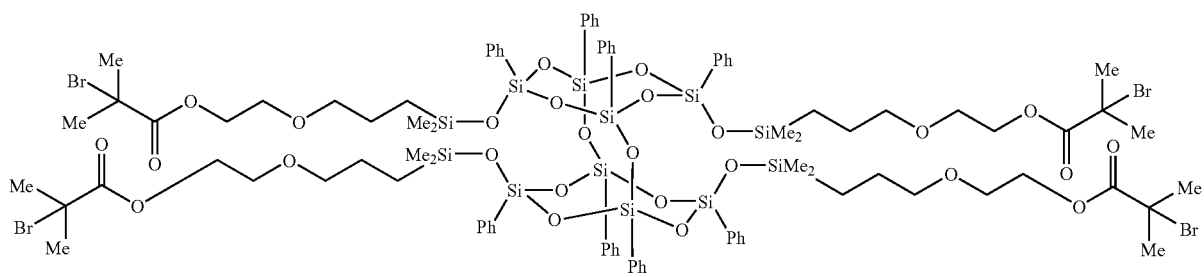

(1-1-3)

<Synthesis of 2-bromo-2-methylpropanoyloxyethoxypropyldimethylchlorosilane>

The same operation as in Example 26 is carried out, except that ethylene glycol monoallyl ether is substituted for allyl alcohol, whereby 2-bromo-2-methylpropanoyloxyethoxypropyldimethylchlorosilane represented by Formula (11-2) can be synthesized:

Example 31

<Synthesis of a Silicon Compound having a 2-bromo-2-methylpropanoyloxyethoxypropyl Group>

The same operation as in Example 30 is carried out, except that the compound (3-2-1) is substituted for the compound (3-1-1), whereby the silicon compound represented by Formula (1-1-3) can be synthesized.

Example 32

<Synthesis of chloromethylphenylethyldimethylchlorosilane>

The same operation as in Example 26 is carried out, except that chloromethylstyrene is substituted for allyl alcohol, whereby chloromethylphenylethyldimethylchlorosilane represented by Formula (11-3) can be synthesized:

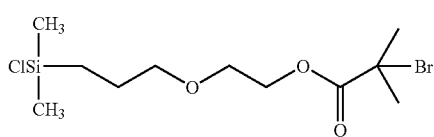

(11-2)

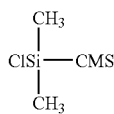
(11-3)

CMS in the above formula is a group represented by any of the following formulas:

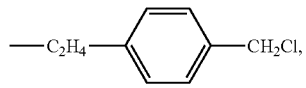

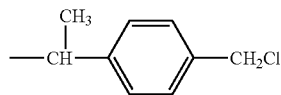

Example 33

<Synthesis of a Silicon Compound having a Chloromethylphenylethyl Group>

The same operation as in Example 27 is carried out, except that chloromethylphenylethyldimethylchlorosilane (4.0 equivalent or more based on the compound (3-1-1)) obtained in Example 32 is substituted for 2-bromo-2-methylpropanoyloxypropyldimethylchlorosilane obtained in Example 26, whereby a silicon compound represented by Formula (1-3-3) can be synthesized:

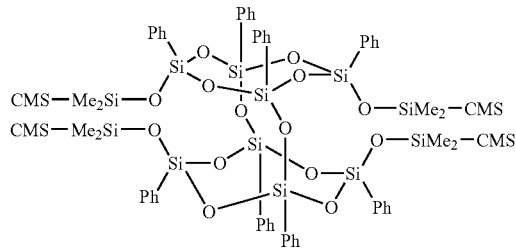
(1-3-3)

CMS in the above formula is the same as CMS in Formula (11-3).

Example 34

<Synthesis of a Silicon Compound having a Chloromethylphenylethyl Group>

The same operation as in Example 33 is carried out, except that the compound (3-2-1) is substituted for the compound (3-1-1), whereby the silicon compound represented by Formula (1-3-3) can be synthesized.

Example 35

<Synthesis of chlorosulfonylethyldimethylchlorosilane>

The same operation as in Example 26 is carried out, except that chlorosulfonylstyrene is substituted for allyl alcohol, whereby chlorosulfonyldimethylchlorosilane represented by Formula (11-4) can be synthesized:

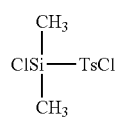
(11-4)

TsCl in the above formula is a group represented by any of the following formulas:

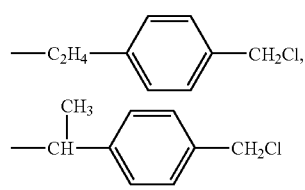

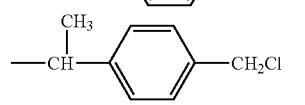

Example 36

<Synthesis of a Silicon Compound having a Chlorosulfonylethyl Group>

The same operation as in Example 27 is carried out, except that chlorosulfonylethyldimethylchlorosilane (4.0 equivalent or more based on the compound (3-1-1)) obtained in Example 35 is substituted for 2-bromo-2-methylpropanoyloxypropyldimethylchlorosilane obtained in Example 26, whereby a silicon compound represented by Formula (1-2-3) can be synthesized:

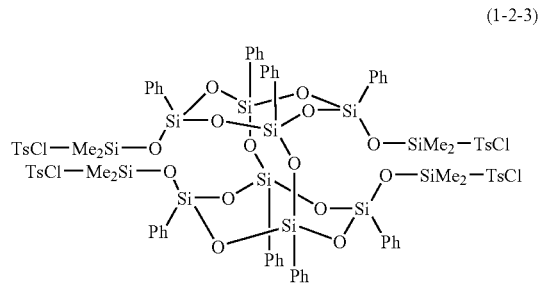
(1-2-3)

TsCl in the above formula is the same as TsCl in Formula (11-4).

Example 37

<Synthesis of a Silicon Compound having a Chlorosulfonylethyl Group>

The same operation as in Example 36 is carried out, except that the compound (3-2-1) is substituted for the compound (3-1-1), whereby the silicon compound represented by Formula (1-2-3) can be synthesized.

What is claimed is:

1. A silicon compound represented by Formula (1):

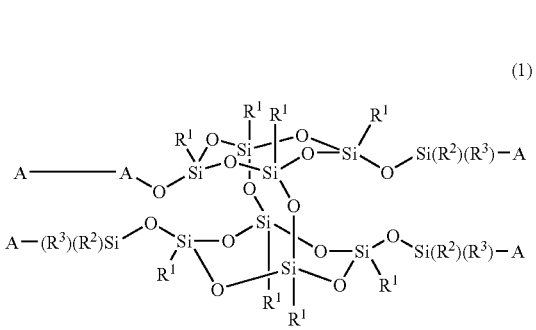

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and A is a group having a polymerization initiating ability for a monomer.

2. The silicon compound as described in claim 1, wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and A is a group having a living radical polymerization initiating ability for a monomer.

3. The silicon compound as described in claim 1, wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and A is a group represented by any of Formula (2-1), Formula (2-2), Formula (2-3) and Formula (2-4);

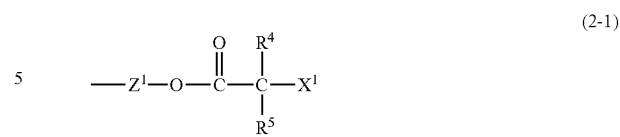

wherein $Z^1$ is alkylene having a carbon atom number of 2 to 20 or alkenylene having a carbon atom number of 3 to 8, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; and $X^1$ is halogen;

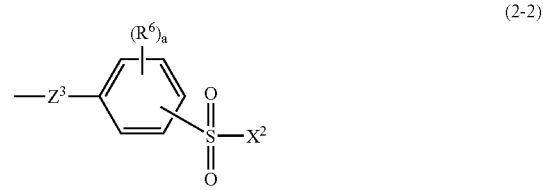

wherein $Z^3$ is alkylene having a carbon atom number of 2 to 10, and optional —$CH_2$— in this alkylene may be substituted with —O— or —COO—; $R^6$ is alkyl having a carbon atom number of 1 to 3; a is an integer of 0 to 2; $X^2$ is halogen; and a bonding position of —$SO_2X^2$ on the benzene ring is an ortho position, a meta position or a para position to a bonding position of $Z^3$, and a bonding position of $R^6$ is an optional position excluding the respective bonding positions of $Z^3$ and —$SO_2X^2$;

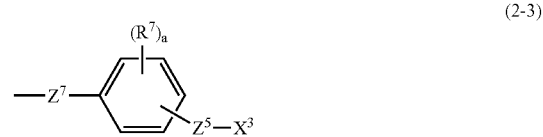

wherein $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; $X^3$ is halogen; and a bonding position of $Z^1$ on the benzene ring is a meta position or a para position to a bonding position of $Z^7$, and a bonding position of $R^7$ is an optional position excluding the respective bonding positions of $Z^5$ and $Z^7$;

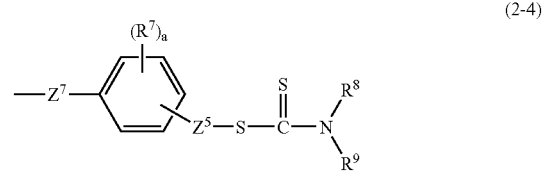

wherein $R^8$ and $R^9$ are independently alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; and a bonding position of $Z^5$ on the benzene ring is a meta position or a para position to a bonding position of $Z^7$, and a bonding position of $R^7$ is an optional position excluding the respective bonding positions of $Z^5$ and $Z^7$.

4. The silicon compound as described in claim 3, wherein respective $R^1$'s are groups independently selected from hydrogen and alkyl having a carbon atom number of 1 to 30 in which optional hydrogen may be substituted with fluorine and in which optional —$CH_2$— may be substituted with —O— or cycloalkylene.

5. The silicon compound as described in claim 3, wherein respective $R^1$'s are groups independently selected from alkenyl having a carbon atom number of 2 to 20 in which optional hydrogen may be substituted with fluorine and in which optional —$CH_2$— may be substituted with —O— or cycloalkylene and alkyl having a carbon atom number of 1 to 20 in which optional hydrogen may be substituted with fluorine and in which at least one —$CH_2$— is substituted with cycloalkenylene.

6. The silicon compound as described in claim 3, wherein respective $R^1$'s are groups independently selected from phenyl in which optional hydrogen may be substituted with halogen or alkyl having a carbon atom number of 1 to 10 and non-substituted naphthyl; in alkyl which is a substituent of the phenyl, optional hydrogen may be substituted with fluorine, and optional —$CH_2$— may be substituted with —O—, —CH=CH—, cycloalkylene or phenylene; and when the phenyl has plural substituents, the substituents may be the same group or different groups.

7. The silicon compound as described in claim 3, wherein respective $R^1$'s are groups independently selected from phenylalkyl constituted from a phenyl group in which optional hydrogen may be substituted with halogen or alkyl having a carbon atom number of 1 to 12 and an alkylene group having a carbon atom number of 1 to 12 in which optional hydrogen may be substituted with fluorine and in which optional —$CH_2$— may be substituted with —O—, —CH=CH— or cycloalkylene; in alkyl which is a substituent of the phenyl group, optional hydrogen may be substituted with fluorine, and optional —$CH_2$— may be substituted with —O—, —CH=CH—, cycloalkylene or phenylene; and when the phenyl group has plural substituents, the substituents may be the same group or different groups.

8. The silicon compound as described in claim 3, wherein respective $R^1$'s are groups independently selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; and when the phenyl or a phenyl group in the phenylalkyl has plural substituents, the substituents may be the same group or different groups.

9. The silicon compound as described in claim 3, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; and when the phenyl or a phenyl group in the phenylalkyl has plural substituents, the substituents may be the same group or different groups.

10. The silicon compound as described in claim 3, wherein all $R^1$'s are phenyl.

11. The silicon compound as described in claim 3, wherein all $R^1$'s are phenyl, and $R^2$ and $R^3$ are methyl.

12. The silicon compound as described in claim 3, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and A is the group represented by Formula (2-1):

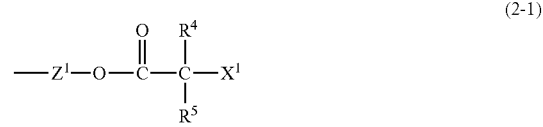

(2-1)

wherein $Z^1$ is alkylene having a carbon atom number of 2 to 20 or alkenylene having a carbon atom number of 3 to 8, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; and $X^1$ is halogen.

13. The silicon compound as described in claim 3, wherein all $R^1$'s are phenyl; A is the group represented by Formula (2-1); and $Z^1$ in Formula (2-1) is alkylene which has a carbon atom number of 2 to 10 and in which optional —$CH_2$— may be substituted with —O—.

14. The silicon compound as described in claim 3, wherein all $R^1$'s are phenyl; $R^2$ and $R^3$ are methyl; A is the group represented by Formula (2-1); in Formula (2-1), $Z^1$ is —$C_2H_4$—, —$C_3H_6$— or —$C_2H_4$—O—$C_3H_6$—; $R^4$ and $R^5$ are methyl; and $X^1$ is bromine.

15. The silicon compound as described in claim 3, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and A is the group represented by Formula (2-2):

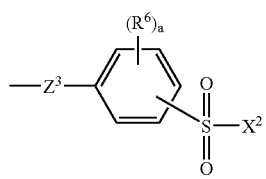

(2-2)

wherein $Z^3$ is alkylene having a carbon atom number of 2 to 10, and optional —$CH_2$— in this alkylene may be substituted with —O— or —COO—; $R^6$ is alkyl having a carbon atom number of 1 to 3; a is an integer of 0 to 2; $X^2$ is halogen; and a bonding position of —$SO_2X^2$ on the benzene ring is an ortho position, a meta position or a para position to a bonding position of $Z^3$, and a bonding position of $R^6$ is an optional position excluding the respective bonding positions of $Z^3$ and —$SO_2X^2$.

16. The silicon compound as described in claim 3, wherein all $R^1$'s are phenyl; A is the group represented by Formula (2-2); $Z^3$ in Formula (2-2) is —$C_2H_4$—$Z^9$; and $Z^9$ is a single bond or alkylene which has a carbon atom number of 1 to 8 and in which optional —$CH_2$— may be substituted with —O— or —COO—.

17. The silicon compound as described in claim 3, wherein all $R^1$'s are phenyl; $R^2$ and $R^3$ are methyl; A is the group represented by Formula (2-2); in Formula (2-2), $Z^3$ is —$C_2H_4$—; $X^2$ is chlorine or bromine; and a is 0.

18. The silicon compound as described in claim 3, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and A is the group represented by Formula (2-3):

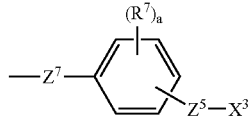

(2-3)

wherein $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; $X^3$ is halogen; and a bonding position of $Z^5$ on the benzene ring is a meta position or a para position to a bonding position of $Z^7$, and a bonding position of $R^7$ is an optional position excluding the respective bonding positions of $Z^5$ and $Z^7$.

19. The silicon compound as described in claim 3, wherein all $R^1$'s are phenyl; A is the group represented by Formula (2-3); $Z^7$ in Formula (2-3) is —$C_2H_4$—$Z^{10}$, and $Z^{10}$ is a single bond or alkylene which has a carbon atom number of 1 to 8 and in which optional —$CH_2$— may be substituted with —O—, —COO— or —OCO—.

20. The silicon compound as described in claim 3, wherein all $R^1$'s are phenyl; $R^2$ and $R^3$ are methyl; A is the group represented by Formula (2-3); in Formula (2-3), $Z^5$ is —$CH_2$—; $Z^7$ is —$C_2H_4$—; $X^3$ is chlorine or bromine; and a is 0.

21. The silicon compound as described in claim 3, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and A is the group represented by Formula (2-4):

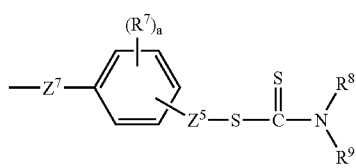

(2-4)

wherein $R^8$ and $R^9$ are independently hydrogen, alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; and a bonding position of $Z^5$ on the benzene ring is a meta position or a para position to a bonding position of $Z^7$, and a bonding position of $R^7$ is an optional position excluding the respective bonding positions of $Z^5$ and $Z^7$.

22. The silicon compound as described in claim 3, wherein all $R^1$'s are phenyl; A is the group represented by Formula (2-4); and in Formula (2-4), $Z^7$ is —$C_2H_4$—$Z^{10}$, and $Z^{10}$ is a single bond or alkylene which has a carbon atom number of 1 to 8 and in which optional —$CH_2$— may be substituted with —O—, —COO— or —OCO—.

23. The silicon compound as described in claim 3, wherein all $R^1$'s are phenyl; $R^2$ and $R^3$ are methyl; A is the group represented by Formula (2-4); in Formula (2-4), $R^8$ and $R^8$ are ethyl; $Z^5$ is —$CH_2$—; $Z^7$ is —$C_2H_4$—; and a is 0.

24. A production process for a silicon compound represented by Formula (1-1) characterized by obtaining a compound represented by Formula (5) by a step (a) and carrying out a step (b) and then a step (c):

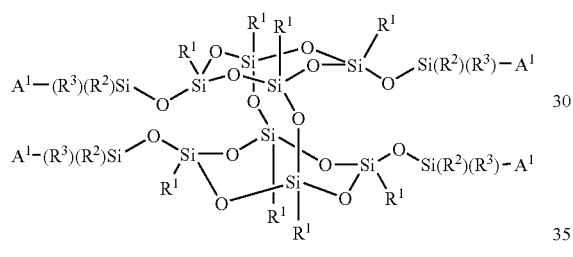

(1-1)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^1$ is a group represented by Formula (2-1-1):

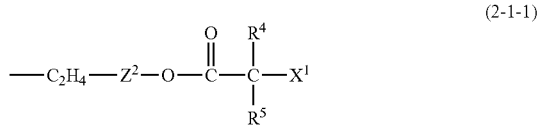

(2-1-1)

wherein $Z^2$ is a single bond or alkylene having a carbon atom number of 1 to 18 or alkenylene having a carbon atom number of 2 to 6, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; and $X^1$ is halogen;

<Step (a)> a step in which a compound represented by Formula (3-1) is reacted with a compound represented by Formula (4) to thereby obtain a compound represented by Formula (5):

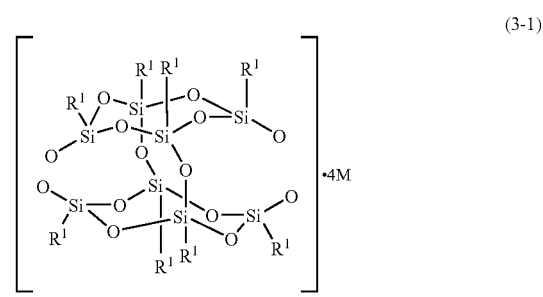

(3-1)

(4)

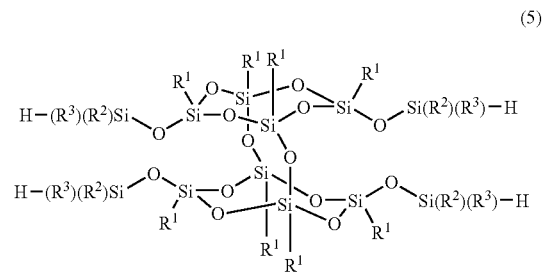

(5)

wherein in the above formulas, $R^1$, $R^2$ and $R^3$ have the same meanings as those of these codes in Formula (1-1), and M is a monovalent alkali metal atom;

<Step (b)> a step in which the compound represented by Formula (5) is reacted with a compound represented by Formula (6) in the presence of a transition metal catalyst to obtain a silicon compound represented by Formula (7):

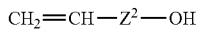 (6)

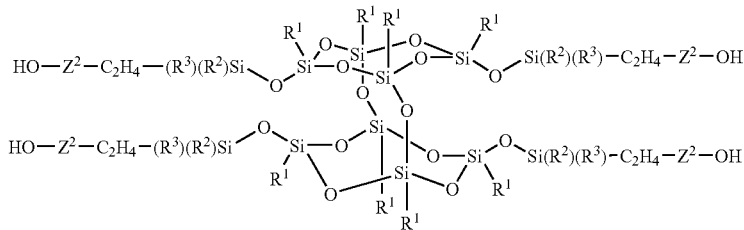 (7)

wherein $Z^2$ in the above formulas has the same meaning as that of $Z^2$ in Formula (2-1-1), and $R^1$, $R^2$ and $R^3$ in Formula (7) have the same meanings as those of these codes in Formula (1-1);

<Step (c)>
a step in which the compound represented by Formula (7) is reacted with a compound represented by Formula (8) to obtain the silicon compound represented by Formula (1-1):

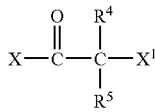 (8)

wherein $R^4$, $R^5$ and $X^1$ have the same meanings as those of these codes in Formula (2-1-1); and X is halogen.

25. The production process as described in claim 24, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

26. The production process as described in claim 24, wherein all $R^1$'s are phenyl, and $R^2$ and $R^3$ are methyl.

27. A production process for a silicon compound represented by Formula (1-1) characterized by obtaining a compound represented by Formula (5) by a step (d) and carrying out a step (b) and then a step (c):

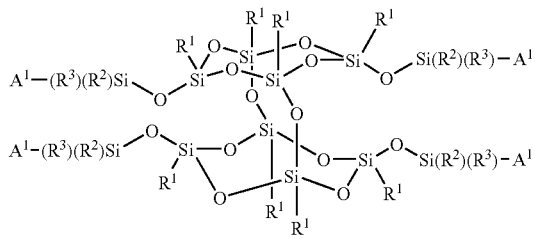 (1-1)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^1$ is a group represented by Formula (2-1-1):

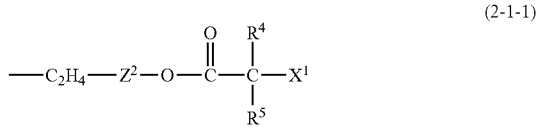 (2-1-1)

wherein $Z^2$ is a single bond or alkylene having a carbon atom number of 1 to 18 or alkenylene having a carbon atom number of 2 to 6, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; and $X^1$ is halogen;

<Step (d)>
a step in which a compound represented by Formula (3-2) is reacted with a compound represented by Formula (4) to thereby obtain a compound represented by Formula (5):

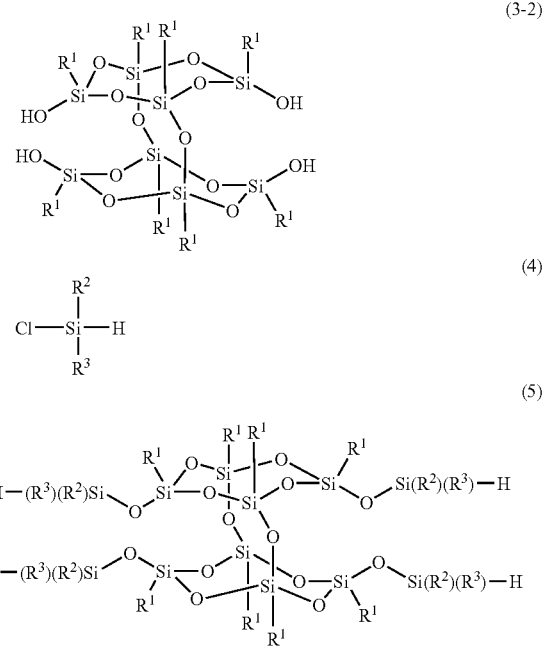

(3-2)

(4)

(5)

wherein $R^1$, $R^2$ and $R^3$ in the above formulas have the same meanings as those of these codes in Formula (1-1);

\<Step (b)\>
a step in which the compound represented by Formula (5) is reacted with a compound represented by Formula (6) in the presence of a transition metal catalyst to obtain a silicon compound represented by Formula (7):

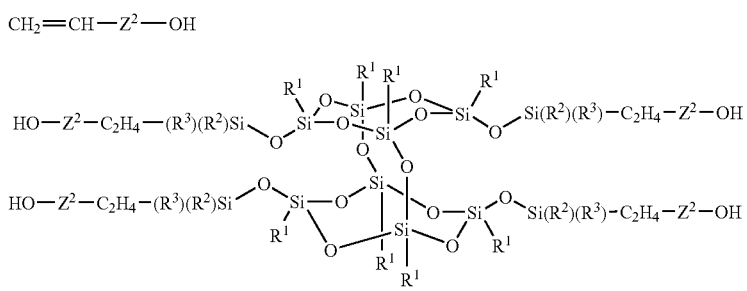

(6)

(7)

wherein $Z^2$ in the above formulas has the same meaning as that of $Z^2$ in Formula (2-1-1), and $R^1$, $R^2$ and $R^3$ in Formula (7) have the same meanings as those of these codes in Formula (1-1);

\<Step (c)\>
a step in which the compound represented by Formula (7) is reacted with a compound represented by Formula (8) to obtain the silicon compound represented by Formula (1-1):

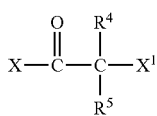

(8)

wherein $R^4$, $R^5$ and $X^1$ have the same meanings as those of these codes in Formula (2-1-1); and X is halogen.

28. The production process as described in claim 27, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

29. The production process as described in claim 27, wherein all $R^1$'s are phenyl, and $R^2$ and $R^3$ are methyl.

30. A production process for a silicon compound represented by Formula (1-3) characterized by carrying out a step (e) and then a step (f):

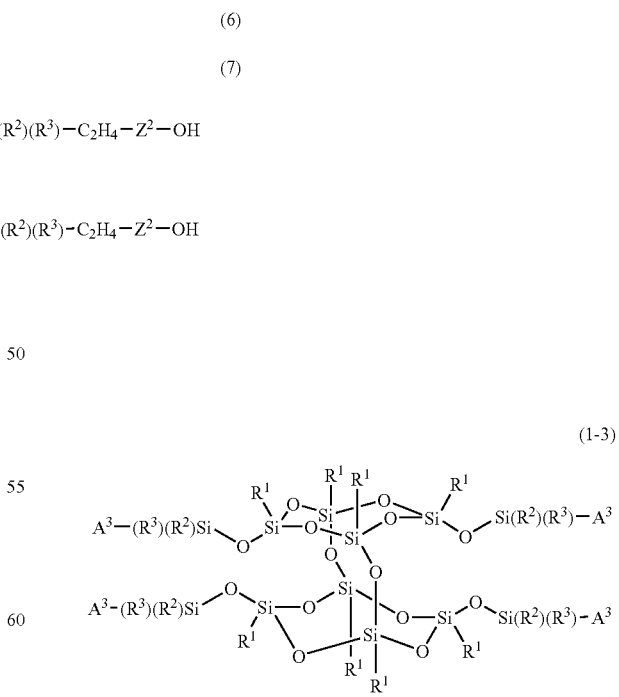

(1-3)

wherein respective $R^1$'s are groups independently selected from hydrogen, alkyl having a carbon atom number of 1 to 45 in which optional hydrogen may be substituted with fluorine and in which optional —CH$_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —CH$_2$— may be substituted with —O—, —CH=CH— or cycloalkylene; R$^2$ and R$^3$ are groups independently selected from alkyl having a carbon atom number of 1 to 8, phenyl and cyclohexyl; and A$^3$ is a group represented by Formula (2-3-1):

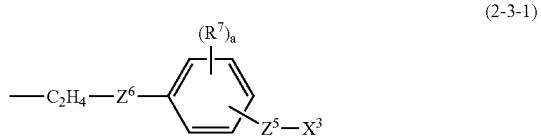

(2-3-1)

wherein Z$^5$ is alkylene which has a carbon atom number of 1 to 3 and in which optional —CH$_2$— may be substituted with —O—; Z$^6$ is a single bond or alkylene which has a carbon atom number of 1 to 8 and in which optional —CH$_2$— may be substituted with —O—, —COO— or —OCO—; R$^7$ is alkyl having a carbon atom number of 1 to 3; a is an integer of 0 to 2; X$^3$ is halogen; and a bonding position of Z$^5$ on the benzene ring is a meta position or a para position to a bonding position of Z$^6$, and a bonding position of R$^7$ is an optional position excluding the respective bonding positions of Z$^5$ and Z$^6$;
<Step (e)>
a step in which a compound represented by Formula (4) is reacted with a compound represented by Formula (3-1) or a compound represented by Formula (3-2) to obtain a silicon compound represented by Formula (5):

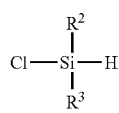

(4)

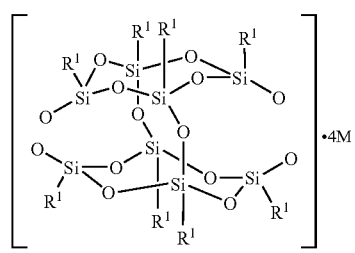

(3-1)

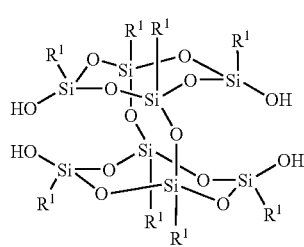

(3-2)

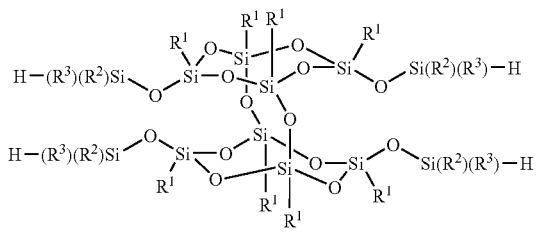

(5)

wherein R$^1$, R$^2$ and R$^3$ in the above formulas have the same meanings as those of these codes in Formula (1-3), and M is a monovalent alkali metal atom;
<Step (f)>
a step in which the compound represented by Formula (5) is reacted with a compound represented by Formula (2-3-2) to obtain the silicon compound represented by Formula (1-3):

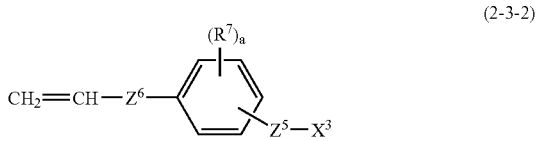

(2-3-2)

wherein Z$^5$, Z$^6$, R$^7$, a and X$^3$ have the same meanings as those of these codes in Formula (2-3-1); and the bonding positions of Z$^5$ and R$^7$ on the benzene ring are the same as the bonding positions thereof in Formula (2-3-1).

31. The production process as described in claim 30, wherein all R$^1$'s are the same group selected from alkyl having a carbon atom number of 1 to 8 in which optional hydrogen may be substituted with fluorine and in which optional —CH$_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —CH$_2$— may be substituted with —O—, —CH=CH— or cycloalkylene; when the phenyl or a phenyl group in the phenylalkyl has plural substituents, the substituents may be the same group or different groups; and R$^2$ and R$^3$ are groups independently selected from alkyl having a carbon atom number of 1 to 8, phenyl and cyclohexyl.

32. The production process as described in claim 30, wherein all R$^1$'s are phenyl, and R$^2$ and R$^3$ are methyl.

33. A production process for a silicon compound represented by Formula (1-4) characterized by reacting a silicon compound represented by Formula (1-3) with a compound represented by Formula (9):

(1-4)

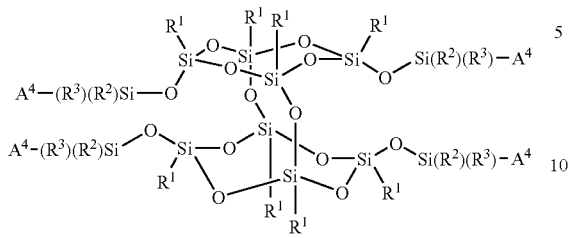

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^4$ is a group represented by Formula (2-4-1):

(2-4-1)

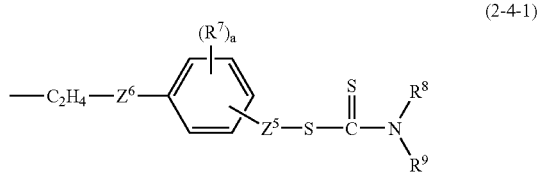

wherein $Z^5$ is alkylene which has a carbon atom number of 1 to 3 and in which optional —$CH_2$— may be substituted with —O—; $Z^6$ is a single bond or alkylene which has a carbon atom number of 1 to 8 and in which optional —$CH_2$— may be substituted with —O—, —COO— or —OCO—; $R^8$ and $R^9$ are independently hydrogen, alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $R^7$ is alkyl having a carbon atom number of 1 to 3; a is an integer of 0 to 2; and a bonding position of $Z^5$ on the benzene ring is a meta position or a para position to a bonding position of $Z^6$, and a bonding position of $R^7$ is an optional position excluding the respective bonding positions of $Z^5$ and $Z^6$;

(1-3)

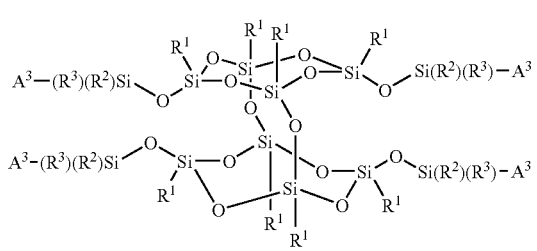

wherein $R^1$, $R^2$ and $R^3$ have the same meanings as those of these codes in Formula (1-4), and $A^3$ is a group represented by Formula (2-3-1):

(2-3-1)

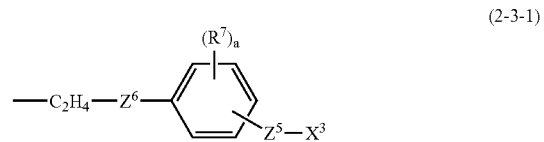

wherein $Z^5$, $Z^6$, $R^7$ and a have the same meanings as those of these codes in Formula (2-4-1); $X^3$ is halogen; and the bonding positions of $Z^5$ and $R^7$ on the benzene ring are the same as the bonding positions thereof in Formula (2-4-1);

(9)

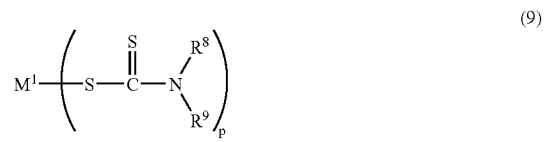

wherein $R^8$ and $R^9$ have the same meanings as those of these codes in Formula (2-4-1); $M^1$ is a metal element of the first group or the second group in the periodic table; and p is the same value as a valence of $M^1$.

34. The production process as described in claim 33, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

35. The production process as described in claim 33, wherein all $R^1$'s are phenyl, and $R^2$ and $R^3$ are methyl.

36. A production process for a silicon compound represented by Formula (1-1) characterized by carrying out a step (g) and then a step (h):

(1-1)

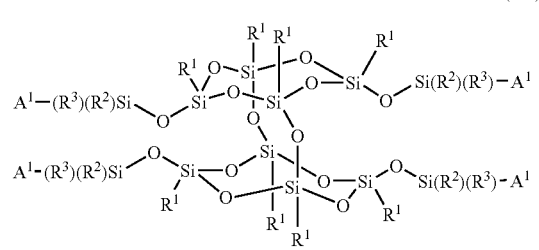

wherein respective R¹'s are groups independently selected from hydrogen, alkyl having a carbon atom number of 1 to 45 in which optional hydrogen may be substituted with fluorine and in which optional —CH$_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —CH$_2$— may be substituted with —O—, —CH=CH— or cycloalkylene; R² and R³ are groups independently selected from alkyl having a carbon atom number of 1 to 8, phenyl and cyclohexyl; and A¹ is a group represented by Formula (2-1-1):

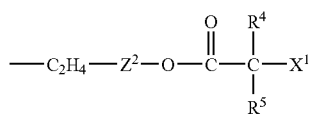

(2-1-1)

wherein Z² is a single bond or alkylene having a carbon atom number of 1 to 18 or alkenylene having a carbon atom number of 2 to 6, and optional —CH$_2$— in these alkylene and alkenylene may be substituted with —O—; R⁴ is hydrogen, alkyl having a carbon atom number of 1 to 20, aryl having a carbon atom number of 6 to 20 or arylalkyl having a carbon atom number of 7 to 20; R⁵ is alkyl having a carbon atom number of 1 to 20, aryl having a carbon atom number of 6 to 20 or arylalkyl having a carbon atom number of 7 to 20; and X¹ is halogen;

<Step (g)> a step in which a compound represented by Formula (4) is reacted with a compound represented by Formula (2-1-2) in the presence of a transition metal catalyst to obtain a silicon compound represented by Formula (2-1-3):

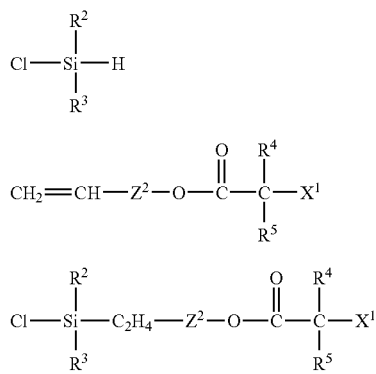

(4)

(2-1-2)

(2-1-3)

wherein R² and R³ in the above formulas have the same meanings as those of these codes in Formula (1-1), and Z², R⁴, R⁵ and X¹ have the same meanings as those of these codes in Formula (2-1-1);

<Step (h)> a step in which the compound represented by Formula (2-1-3) is reacted with a compound represented by Formula (3-1) or a compound represented by Formula (3-2) to thereby obtain the compound represented by Formula (1-1):

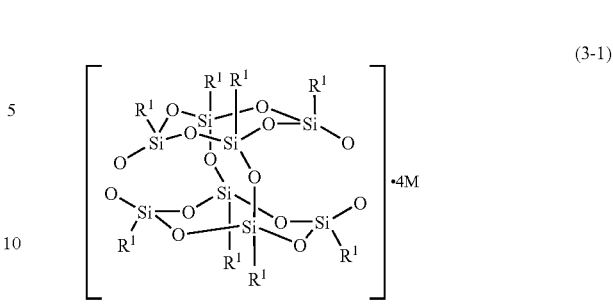

(3-1)

(3-2)

wherein R¹ in the above formulas has the same meaning as that of R¹ in Formula (1-1), and M is a monovalent alkali metal atom.

37. The production process as described in claim 36, wherein all R¹'s are the same group selected from alkyl having a carbon atom number of 1 to 8 in which optional hydrogen may be substituted with fluorine and in which optional —CH$_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —CH$_2$— may be substituted with —O—, —CH=CH— or cycloalkylene; when the phenyl or a phenyl group in the phenylalkyl has plural substituents, the substituents may be the same group or different groups; and R² and R³ are groups independently selected from alkyl having a carbon atom number of 1 to 8, phenyl and cyclohexyl.

38. The production process as described in claim 36, wherein all R¹'s are phenyl, and R² and R³ are methyl.

39. A production process for a silicon compound represented by Formula (1-2) characterized by carrying out a step (i) and then a step (j):

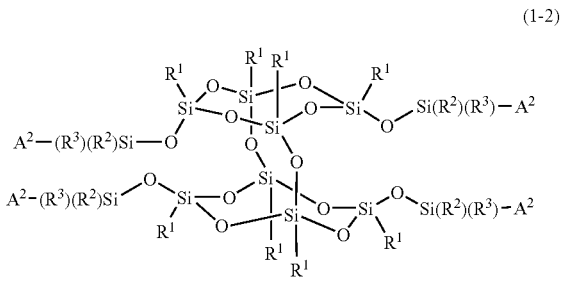

(1-2)

wherein respective R¹'s are groups independently selected from hydrogen, alkyl having a carbon atom number of 1 to 45 in which optional hydrogen may be substituted with fluorine and in which optional —CH$_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —CH$_2$— may be substituted with —O—, —CH=CH— or cycloalkylene; R$^2$ and R$^3$ are groups independently selected from alkyl having a carbon atom number of 1 to 8, phenyl and cyclohexyl; and A$^2$ is a group represented by Formula (2-2-1):

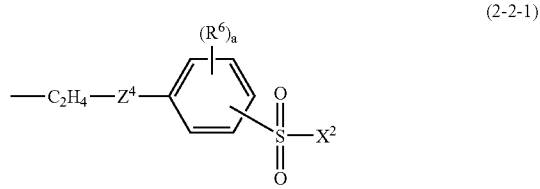

(2-2-1)

wherein Z$^4$ is a single bond or alkylene having a carbon atom number of 1 to 8, and optional —CH$_2$— in the above alkylene may be substituted with —O— or —COO—; R$^6$ is alkyl having a carbon atom number of 1 to 3; a is an integer of 0 to 2; X$^2$ is halogen; and a bonding position of —SO$_2$X$^2$ on the benzene ring is an ortho position, a meta position or a para position to a bonding position of Z$^4$, and a bonding position of R$^6$ is an optional position excluding the respective bonding positions of Z$^4$ and —SO$_2$X$^2$;

<Step (i)> a step in which a compound represented by Formula (4) is reacted with a compound represented by Formula (2-2-2) in the presence of a transition metal catalyst to obtain a compound represented by Formula (2-2-3):

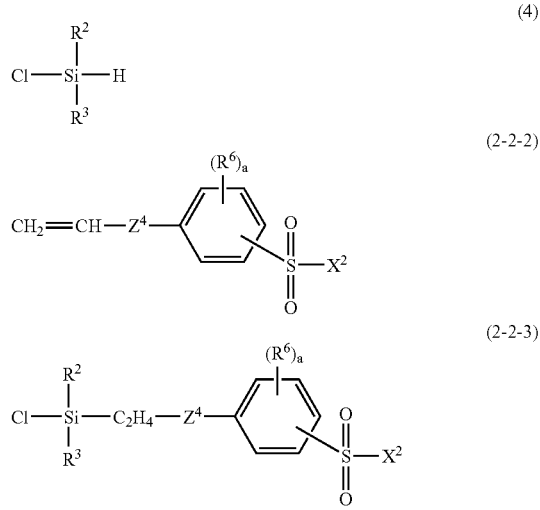

wherein R$^2$ and R$^3$ in the above formulas have the same meanings as those of these codes in Formula (1-2); Z$^4$, R$^6$, a and X$^2$ have the same meanings as those of these codes in Formula (2-2-1); and the bonding positions of —SO$_2$X$^2$ and R$^6$ on the benzene ring are the same as the bonding positions thereof in Formula (2-2-1);

<Step (j)> a step in which the compound represented by Formula (2-2-3) is reacted with a compound represented by Formula (3-1) or a compound represented by Formula (3-2) to obtain the silicon compound represented by Formula (1-2):

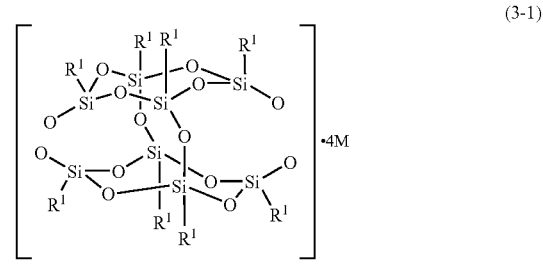

(3-1)

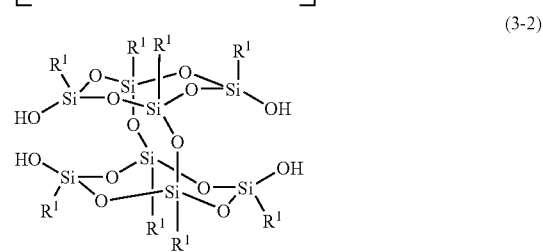

(3-2)

wherein R$^1$ in the above formulas has the same meaning as that of R$^1$ in Formula (1-1); and M is a monovalent alkali metal atom.

40. The production process as described in claim 39, wherein all R$^1$'s are the same group selected from alkyl having a carbon atom number of 1 to 8 in which optional hydrogen may be substituted with fluorine and in which optional —CH$_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —CH$_2$— may be substituted with —O—, —CH=CH— or cycloalkylene; when the phenyl or a phenyl group in the phenylalkyl has plural substituents, the substituents may be the same group or different groups; and R$^2$ and R$^3$ are groups independently selected from alkyl having a carbon atom number of 1 to 8, phenyl and cyclohexyl.

41. The production process as described in claim 39, wherein all R$^1$'s are phenyl, and R$^2$ and R$^3$ are methyl.

42. A production process for a silicon compound represented by Formula (1-3) characterized by carrying out a step (k) and then a step (l):

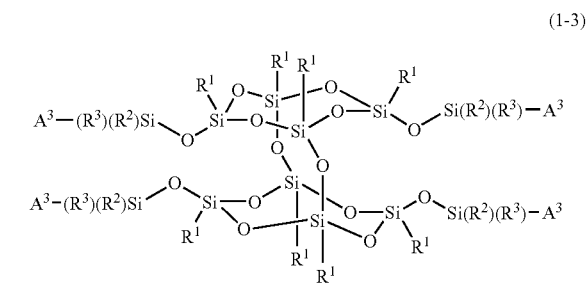

(1-3)

wherein respective $R^1$'s are groups independently selected from hydrogen, alkyl having a carbon atom number of 1 to 45 in which optional hydrogen may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogen may be substituted with fluorine and in which optional —$CH_2$— may be substituted with —O—, —CH=CH— or cycloalkylene; $R^2$ and $R^3$ are groups independently selected from alkyl having a carbon atom number of 1 to 8, phenyl and cyclohexyl; and $A^3$ is a group represented by Formula (2-3-1):

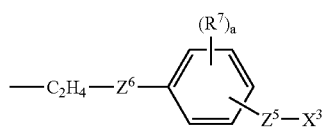

(2-3-1)

wherein $Z^5$ is alkylene which has a carbon atom number of 1 to 3 and in which optional —$CH_2$— may be substituted with —O—; $Z^6$ is a single bond or alkylene which has a carbon atom number of 1 to 8 and in which optional —$CH_2$— may be substituted with —O—, —COO— or —OCO—; $R^7$ is alkyl having a carbon atom number of 1 to 3; a is an integer of 0 to 2; $X^3$ is halogen; and a bonding position of $Z^5$ on the benzene ring is a meta position or a para position to a bonding position of $Z^6$, and a bonding position of $R^7$ is an optional position excluding the respective bonding positions of $Z^5$ and $Z^6$;

<Step (k)>
a step in which a compound represented by Formula (4) is reacted with a compound represented by Formula (2-3-2) in the presence of a transition metal catalyst to obtain a compound represented by Formula (2-3-3):

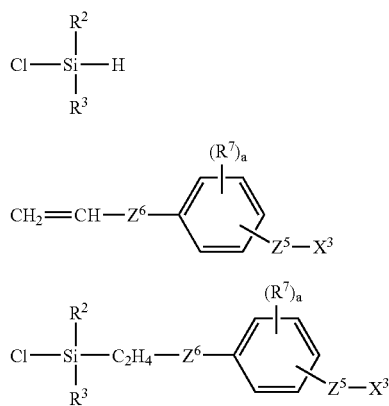

wherein $R^2$ and $R^3$ in the above formulas have the same meanings as those of these codes in Formula (1-3); $Z^5$, $Z^6$, $R^7$, a and $X^3$ have the same meanings as those of these codes in Formula (2-3-1); and the bonding positions of $Z^5$ and $R^7$ on the benzene ring are the same as the bonding positions thereof in Formula (2-3-1);

<Step (l)>
a step in which the compound represented by Formula (2-3-3) is reacted with a compound represented by Formula (3-1) or a compound represented by Formula (3-2) to thereby obtain the silicon compound represented by Formula (1-3):

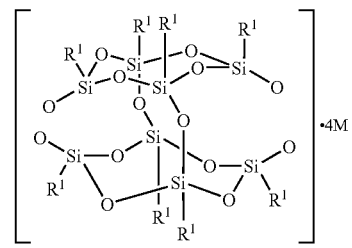

(3-1)

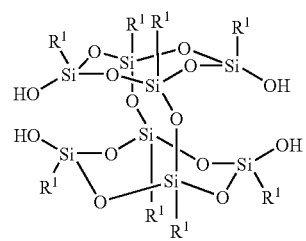

(3-2)

wherein $R^1$ in the above formulas has the same meaning as that of $R^1$ in Formula (1-3); and M is a monovalent alkali metal atom.

43. The production process as described in claim 42, wherein all $R^1$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; and $R^2$ and $R^3$ are groups independently selected from alkyl having a carbon atom number of 1 to 8, phenyl and cyclohexyl.

44. The production process as described in claim 42, wherein all $R^1$'s are phenyl, and $R^2$ and $R^3$ are methyl.

45. A polymer obtained by polymerizing an addition-polymerizable monomer using the silicon compound as described in claim 1 as an initiator and using a transition metal complex as a catalyst.

46. A polymer obtained by polymerizing an addition-polymerizable monomer using the silicon compound as described in claim 3 as an initiator and using a transition metal complex as a catalyst.

47. A polymer represented by Formula (P-1):

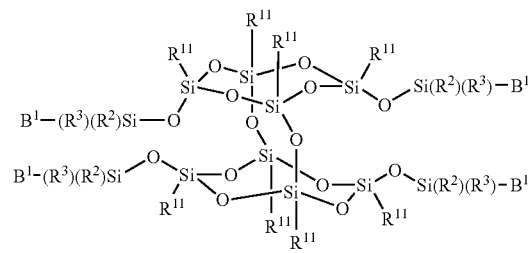

(P-1)

wherein all $R^{11}$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; $R^2$ and $R^3$ are groups independently selected from alkyl having a carbon atom number of 1 to 8, phenyl and cyclohexyl; and $B^1$ is a group represented by Formula (2-1-P):

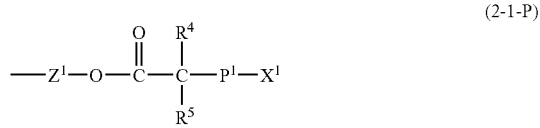

(2-1-P)

wherein $Z^1$ is alkylene having a carbon atom number of 2 to 20 or alkenylene having a carbon atom number of 3 to 8, and optional —$CH_2$— in these alkylene and alkenylene may be substituted with —O—; $R^4$ is hydrogen, alkyl having a carbon atom number of 1 to 20, aryl having a carbon atom number of 6 to 20 or arylalkyl having a carbon atom number of 7 to 20; $R^5$ is alkyl having a carbon atom number of 1 to 20, aryl having a carbon atom number of 6 to 20 or arylalkyl having a carbon atom number of 7 to 20; $X^1$ is halogen; and $P^1$ is a chain of a structural unit obtained by polymerizing an addition-polymerizable monomer.

48. A polymer represented by Formula (P-2):

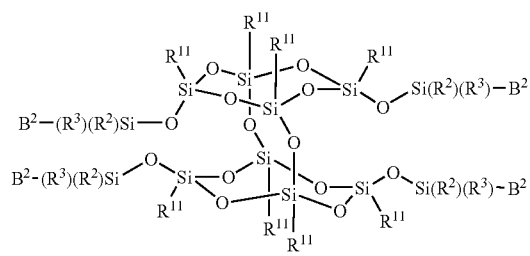

(P-2)

wherein all $R^{11}$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; $R^2$ and $R^3$ are groups independently selected from alkyl having a carbon atom number of 1 to 8, phenyl and cyclohexyl; and $B^2$ is a group represented by Formula (2-2-P):

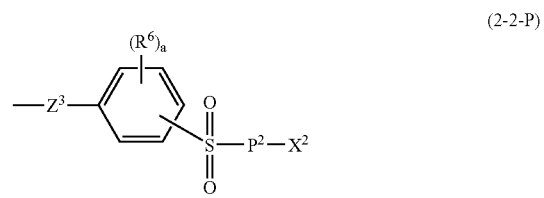

(2-2-P)

wherein $Z^3$ is alkylene having a carbon atom number of 2 to 10, and optional —$CH_2$— in the above alkylene may be substituted with —O— or —COO—; $R^6$ is alkyl having a carbon atom number of 1 to 3; a is an integer of 0 to 2; $X^2$ is halogen; a bonding position of —$SO_2$— on the benzene ring is an ortho position, a meta position or a para position to a bonding position of $Z^3$, and a bonding position of $R^6$ is an optional position excluding the respective bonding positions of $Z^3$ and —$SO_2$—; and $P^2$ is a chain of a structural unit obtained by polymerizing an addition-polymerizable monomer.

49. A polymer represented by Formula (P-3):

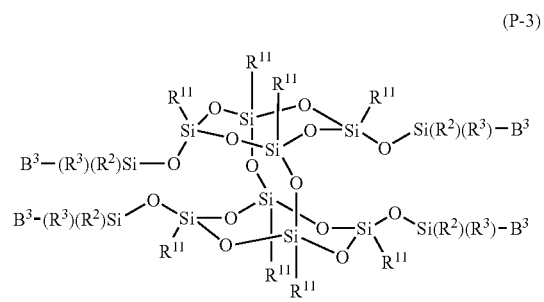

(P-3)

wherein all $R^{11}$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; $R^2$ and $R^3$ are groups independently selected from alkyl having a carbon atom number of 1 to 8, phenyl and cyclohexyl; and $B^3$ is a group represented by Formula (2-3-P):

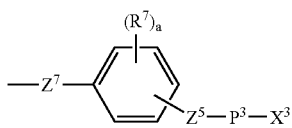

(2-3-P)

wherein $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^7$ is alkyl having a carbon atom number of 1 to 3; a is an integer of 0 to 2; $X^3$ is halogen; a bonding position of $Z^5$ on the benzene ring is a meta position or a para position to a bonding position of $Z^7$, and a bonding position of $R^7$ is an optional position excluding the respective bonding positions of $Z^5$ and $Z^7$; and $P^3$ is a chain of a structural unit obtained by polymerizing an addition-polymerizable monomer.

50. A polymer represented by Formula (P-4):

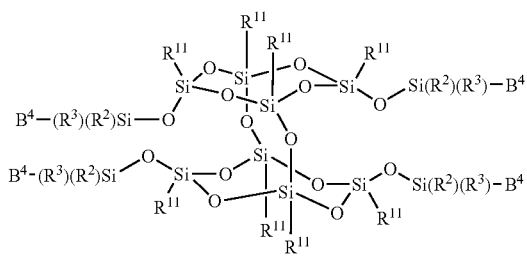

(P-4)

wherein all $R^{11}$'s are the same group selected from alkyl having a carbon atom number of 1 to 8 in which optional hydrogen may be substituted with fluorine and in which optional —$CH_2$— may be substituted with —O—, —CH=CH—, cycloalkylene or cycloalkenylene, phenyl in which optional hydrogen may be substituted with halogen, methyl or methoxy, non-substituted naphthyl and phenylalkyl constituted from a phenyl group in which optional hydrogen may be substituted with fluorine, alkyl having a carbon atom number of 1 to 4, vinyl or methoxy and an alkylene group which has a carbon atom number of 1 to 8 and in which optional —$CH_2$— may be substituted with —O—, —CH=CH— or cycloalkylene; when the phenyl or a phenyl group in the phenylalkyl has plural substituents, the substituents may be the same group or different groups; $R^2$ and $R^3$ are groups independently selected from alkyl having a carbon atom number of 1 to 8, phenyl and cyclohexyl; and $B^4$ is a group represented by Formula (2-4-P):

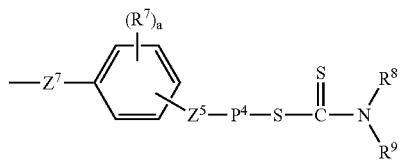

(2-4-P)

wherein $Z^5$ is alkylene which has a carbon atom number of 1 to 3 and in which optional —$CH_2$— may be substituted with —O—; $Z^7$ is alkylene which has a carbon atom number of 2 to 10 and in which optional —$CH_2$— may be substituted with —O—, —COO— or —OCO—; $R^8$ and $R^9$ are independently hydrogen, alkyl having a carbon atom number of 1 to 12, cycloalkyl having a carbon atom number of 5 to 10 or aryl having a carbon atom number of 6 to 10, and $R^8$ and $R^9$ may be combined with each other to form a ring together with N; $R^7$ is alkyl having a carbon atom number of 1 to 3; a is an integer of 0 to 2; a bonding position of $Z^5$ on the benzene ring is a meta position or a para position to a bonding position of $Z^7$, and a bonding position of $R^7$ is an optional position excluding the respective bonding positions of $Z^5$ and $Z^7$; and $P^4$ is a chain of a structural unit obtained by polymerizing an addition-polymerizable monomer.

51. The polymer as described in claim 47, wherein the addition-polymerizable monomer is at least one selected from the group of (meth)acrylic acid derivatives and the group of styrene derivatives.

52. The polymer as described in claim 48, wherein the addition-polymerizable monomer is at least one selected from the group of (meth)acrylic acid derivatives and the group of styrene derivatives.

53. The polymer as described in claim 49, wherein the addition-polymerizable monomer is at least one selected from the group of (meth)acrylic acid derivatives and the group of styrene derivatives.

54. The polymer as described in claim 50, wherein the addition-polymerizable monomer is at least one selected from the group of (meth)acrylic acid derivatives and the group of styrene derivatives.

* * * * *